United States Patent
Mason et al.

(10) Patent No.: US 12,110,331 B2
(45) Date of Patent: Oct. 8, 2024

(54) CANINE MONOCLONAL ANTIBODIES AGAINST CANINE CYTOTOXIC T LYMPHOCYTE ASSOCIATED PROTEIN 4 (CTLA-4)

(71) Applicants: THE TRUSTEES OF THE UNIVERSITY OF PENNSYLVANIA, Philadelphia, PA (US); VETIGENICS, INC., Philadelphia, PA (US)

(72) Inventors: Nicola J. Mason, Philadelphia, PA (US); Donald L. Siegel, Lansdale, PA (US); Nicholas Chester, Philadelphia, PA (US)

(73) Assignees: The Trustees of the University of Pennsylvania, Philadelphia, PA (US); Vetigenics, Inc., Philadelphia, PA (US)

( * ) Notice: Subject to any disclaimer, the term of this patent is extended or adjusted under 35 U.S.C. 154(b) by 0 days.

(21) Appl. No.: 18/491,182

(22) Filed: Oct. 20, 2023

(65) Prior Publication Data
US 2024/0109967 A1    Apr. 4, 2024

Related U.S. Application Data

(63) Continuation of application No. PCT/US2022/025614, filed on Apr. 20, 2022.

(60) Provisional application No. 63/177,692, filed on Apr. 21, 2021.

(51) Int. Cl.
*C07K 16/28* (2006.01)

(52) U.S. Cl.
CPC ...... *C07K 16/2818* (2013.01); *C07K 2317/20* (2013.01); *C07K 2317/622* (2013.01); *C07K 2317/76* (2013.01); *C07K 2317/92* (2013.01)

(58) Field of Classification Search
CPC ............ C07K 16/2818; C07K 2317/20; C07K 2317/74
USPC ....................................................... 424/144.1
See application file for complete search history.

(56) References Cited

U.S. PATENT DOCUMENTS 8,722,587 B2   5/2014  Mason
2004/0181039 A1   9/2004  Krah et al.

FOREIGN PATENT DOCUMENTS

CA          3216131    * 10/2022
WO   WO-2021009187 A1    1/2021

OTHER PUBLICATIONS

Mason et al (MABS 2021, vol. 13, No. 1, e2004638 (11 pages); Published online: Dec. 2, 2021).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
PCT/US2022/0025614 International Search Report and Written Opinion dated Sep. 14, 2022.

* cited by examiner

*Primary Examiner* — Lynn A Bristol
(74) *Attorney, Agent, or Firm* — Saul Ewing LLP; Kathryn Doyle; Justin Crotty

(57) ABSTRACT

The present invention relates to canine antibodies, binding polypeptides, and scFvs specific for canine cytotoxic T lymphocyte associated protein 4 (CTLA-4).

20 Claims, 23 Drawing Sheets
Specification includes a Sequence Listing.

Canine CTLA-4 library panning and results

| Panning Round | Preabsorption with Strept-AviTag™ CD3 | No. Wells Coated | No. of Washes | Phage Input | Phage Output | % Bound (x $10^{-4}$) | Enrichment from Previous Round |
|---|---|---|---|---|---|---|---|
| 1 | yes | 24 | 5 | $9.00 \times 10^{11}$ | $1.41 \times 10^{6}$ | 1.6 | — |
| 2 | yes | 16 | 10 | $2.80 \times 10^{11}$ | $3.60 \times 10^{6}$ | 13 | 8 x |
| 3 | yes | 8 | 10 | $2.44 \times 10^{11}$ | $5.12 \times 10^{8}$ | 2098 | 162 x |
| 4 | yes | 8 | 10 | $2.16 \times 10^{11}$ | $7.88 \times 10^{8}$ | 3648 | 2 x |

FIG. 1

| clone | isotype | HC1 | HC4 ug/10 cm dish |
|---|---|---|---|
| P3-1 A1 | λμ | 6 | 8 |
| P3-1 B10 | λμ | 86 | 78 |
| P4-1 D5 | λμ | 35 | 44 |
| P4-1 G11 | λμ | 0 | 0 |
| P4-9 control | λγ | 46 | 53 |

FIG. 6

| clone | isotype | IgG class | mutant | ug/ul | total yield ug | yield/ plate ug |
|---|---|---|---|---|---|---|
| MERS | γλ | IgG1 HA | wt | 0.29 | 43.5 | 43.5 |
| A1 | μλ | IgG1 HA | wt | 0 | 0 | 0 |
| A1 | μλ | IgG1 HA | mut2 | 0.27 | 35 | 35 |
| B10 | μλ | IgG1 HA | wt | 0.3 | 45 | 45 |
| D5 | μλ | IgG1 HA | wt | 0.07 | 10 | 10 |

FIG. 9

|  | A1mut2 | B10 | D5 |
|---|---|---|---|
| $k_{on}$ | $2.1 \times 10^5$ $M^{-1}s^{-1}$ | $1.6 \times 10^5$ $M^{-1}s^{-1}$ | $1.2 \times 10^5$ $M^{-1}s^{-1}$ |
| $k_{off}$ | $1.8 \times 10^{-4}$ $M^{-1}s^{-1}$ | $2.5 \times 10^{-4}$ $M^{-1}s^{-1}$ | $1.8 \times 10^{-4}$ $M^{-1}s^{-1}$ |
| $t_{1/2}$ | 64 min | 46 min | 64 min |
| $K_D$ | 0.85nM | 1.5nM | 1.5nM |
| $R_{max}$ | 122 RU | 84 RU | 118 RU |

FIG. 21

```
                              SEQUENCE LISTING

Sequence total quantity: 77
SEQ ID NO: 1            moltype = AA  length = 8
FEATURE                 Location/Qualifiers
REGION                  1..8
                        note = A1 HCDR1
source                  1..8
                        mol_type = protein
                        organism = synthetic construct
SEQUENCE: 1
GFSFSSYA                                                                        8

SEQ ID NO: 2            moltype = AA  length = 8
FEATURE                 Location/Qualifiers
REGION                  1..8
                        note = A1 HCDR2
source                  1..8
                        mol_type = protein
                        organism = synthetic construct
SEQUENCE: 2
INSGGSST                                                                        8

SEQ ID NO: 3            moltype = AA  length = 7
FEATURE                 Location/Qualifiers
REGION                  1..7
                        note = A1 HCDR3
source                  1..7
                        mol_type = protein
                        organism = synthetic construct
SEQUENCE: 3
AISNWAY                                                                         7

SEQ ID NO: 4            moltype = AA  length = 8
FEATURE                 Location/Qualifiers
REGION                  1..8
                        note = A1 LCDR1
source                  1..8
                        mol_type = protein
                        organism = synthetic construct
SEQUENCE: 4
SSDIGKSY                                                                        8

SEQ ID NO: 5            moltype = AA  length = 11
FEATURE                 Location/Qualifiers
REGION                  1..11
                        note = A1 LCDR3
```

```
source                  1..11
                        mol_type = protein
                        organism = synthetic construct
SEQUENCE: 5
SSWDWSLHTY V                                                                         11

SEQ ID NO: 6            moltype = AA   length = 114
FEATURE                 Location/Qualifiers
REGION                  1..114
                        note = A1mut2 VH
source                  1..114
                        mol_type = protein
                        organism = synthetic construct
SEQUENCE: 6
EVQLVETGGD LVKPGGSLRL SCVASGFSFS SYAMNWVRQA PEKGLQLVGG INSGGSSTYY                      60
TDAVKGRFTI SRDNAKNTVY LQMNSLRAED TAVYYCAISN WAYWGQGTLV TVSS                           114

SEQ ID NO: 7            moltype = DNA   length = 342
FEATURE                 Location/Qualifiers
misc_feature            1..342
                        note = A1mut2 VH
source                  1..342
                        mol_type = other DNA
                        organism = synthetic construct
SEQUENCE: 7
gaggtgcagc tggtggagac cggggggagac ctggtgaagc ctggcgggtc cctgagattg                     60
tcctgtgtgg cctctggatt ctccttcagc agttatgcca tgaactgggt ccgccaggct                    120
cctgagaagg ggctgcagct ggtgggcggt attaatagcg gtggaagtag tacatattac                    180
accgacgctg tgaagggccg cttcaccatc tccagagaca cgccaagaa cacagtgtat                     240
ttacagatga atagcctgag agccgaggac acggccgtgt attactgtgc gattagtaat                    300
tgggcctact ggggccaggg aaccctggtc accgtctcct ca                                       342

SEQ ID NO: 8            moltype = AA   length = 110
FEATURE                 Location/Qualifiers
REGION                  1..110
                        note = A1 VL
source                  1..110
                        mol_type = protein
                        organism = synthetic construct
SEQUENCE: 8
QAVLNQPASV SGSLGQRVTI SCTGSSSDIG KSYVAWYQQL PGTGPRTLIN VDGNRASGVP                      60
DRFSVSRSGN TATLTISGLQ AEDEADYHCS SWDWSLHTYV FGSGTQLTIL                                110

SEQ ID NO: 9            moltype = DNA   length = 330
FEATURE                 Location/Qualifiers
misc_feature            1..330
                        note = A1 VL
source                  1..330
                        mol_type = other DNA
                        organism = synthetic construct
SEQUENCE: 9
caggctgtgc tgaatcagcc ggcctcagtg tccgggtccc tgggccagag ggtcaccatc                      60
tcctgcactg gaagcagctc cgacatcggt aaaagttatg tggcctggta ccagcagctc                    120
ccgggaacag gccccagaac cctcatcaat gttgatggta accgagcctc aggggtccct                    180
gatcgattct ctgtctccag gtcaggcaac acagccaccc tgaccatctc cgggctccag                    240
gctgaggatg aggctgatta tcactgctca tcctgggact ggagtctcca tacttacgtg                    300
ttcggctcag ggacccagct gaccatcctc                                                     330

SEQ ID NO: 10           moltype = AA   length = 465
FEATURE                 Location/Qualifiers
REGION                  1..465
                        note = A1mut2 heavy chain full-length cIgG1
source                  1..465
                        mol_type = protein
                        organism = synthetic construct
SEQUENCE: 10
MYRMQLLSCI ALSLALVTNS EVQLVETGGD LVKPGGSLRL SCVASGFSFS SYAMNWVRQA                      60
PEKGLQLVGG INSGGSSTYY TDAVKGRFTI SRDNAKNTVY LQMNSLRAED TAVYYCAISN                     120
WAYWGQGTLV TVSSASTTAP SVFPLAPSCG STSGSTVALA CLVSGYFPEP VTVSWNSGSL                     180
TSGVHTFPSV LQSSGLYSLS SMVTVPSSRW PSETFTCNVV HPASNTKVDK PVFNECRCTD                     240
TPPCPVPEPL GGPSVLIFPP KPKDILRITR TPEVTCVVLD LGREDPEVQI SWFVDGKEVH                     300
TAKTQSREQQ FNGTYRVVSV LPIEHQDWLT GKEFKCRVNH IDLPSPIERT ISKARGRAHK                     360
PSVYVLPPSP KELSSSDTVS VTCLIKDFYP PDIDVEWQSN GQQEPERKHR MTPPQLDEDG                     420
SYFLYSKLSV DKSRWQQGDP FTCAVMHETL QNHYTDLSLS HSPGK                                    465

SEQ ID NO: 11           moltype = DNA   length = 1395
FEATURE                 Location/Qualifiers
misc_feature            1..1395
                        note = A1mut2 heavy chain full-length cIgG1
```

```
source                  1..1395
                        mol_type = other DNA
                        organism = synthetic construct
SEQUENCE: 11
atgtacagga tgcaactcct gtcttgcatt gcactaagtc ttgcacttgt cacgaattcg    60
gaggtgcagc tggtggagac cggggggagac ctggtgaagc ctggcgggtc cctgagattg   120
tcctgtgtgg cctctggatt ctccttcagc agttatgcca tgaactgggt ccgccaggct   180
cctgagaagg ggctgcagct ggtgggcggt attaatagcg gtggaagtag tacatattac   240
accgacgctg tgaagggccg cttcaccatc tccagagaca acgccaagaa cacagtgtat   300
ttacagatga atagcctgag agccgaggac acggccgtgt attactgtgc gattagtaat   360
tgggcctact ggggccaggg aaccctggtc accgtctcct cagctagcac cacggccccc   420
tcggttttcc cactggcccc cagctgcggg tccttccg gctccacggt ggccctggcc      480
tgcctggtgt caggctactt ccccgagcct gtaactgtgt cctggaactc cggctccttg   540
accagcggtg tgcacacctt cccgtccgtc ctgcagtcct cagggctcta ctccctcagc   600
agcatggtga cagtgccctc agcagatgg cccagtgaga ccttcacctg caacgtggtc     660
cacccggcca gcaacactaa gtagacaag ccagtgttca tgaatgcag atgcactgat      720
acacccccat gcccagtccc tgaacctctg ggagggcctt cggtcctcat ctttcccccg   780
aaaccaagg acatcctcag gattaccga cacccgagg tcacctgtgt ggtgttagat       840
ctgggccgtg aggaccctga ggtgcagatc agctggttcg tggatggtaa ggaggtgcac   900
acagccaaga cgcagtctcg tgagcagcag ttcaacggca cctaccgtgt ggtcagcgtc   960
ctccccattg agcaccagga ctggctcaca gggaaggagt tcaagtgcag agtcaaccac  1020
atagacctcc catctcccat cgagaggacc atctctaagg caggccataag            1080
cccagtgtgt atgtcctgcc accatcccca aaggagttgt catccagtga cacagtcagc  1140
gtcacctgcc tgataaaaga cttctaccca ctgacattg atgtgagtg gcagagcaat     1200
ggacagcagg agcctgagag gaagcaccgc atgaccccgc ccagctgga cgaggacggg    1260
tcctacttcc tgtacagcaa gctctctgtg gacaagagcc gctggcagca gggagacccc  1320
ttcacatgtg cggtgatgca tgaaactcta cagaaccact acacagatct atccctctcc  1380
cattctccgg gtaaa                                                   1395

SEQ ID NO: 12           moltype = AA  length = 469
FEATURE                 Location/Qualifiers
REGION                  1..469
                        note = A1mut2 heavy chain full-length cIgG2
source                  1..469
                        mol_type = protein
                        organism = synthetic construct
SEQUENCE: 12
MYRMQLLSCI ALSLALVTNS EVQLVETGGD LVKPGGSLRL SCVASGFSFS SYAMNWVRQA    60
PEKGLQLVGG INSGGSSTYY TDAVKGRFTI SRDNAKNTVY LQMNSLRAED TAVYYCAISN   120
WAYWGQGTLV TVSSASTTAP SVFPLAPSCG STSGSTVALA CLVSGYFPEP VTVSWNSGSL   180
TSGVHTFPSV LQSSGLYSLS SMVTVPSSRW PSETFTCNVA HPASKTKVDK PVPKRENGRV   240
PRPPDCPKCP APEMLGGPSV FIFPPKPKDT LLIARTPEVT CVVVDLDPED PEVQISWFVD   300
GKQMQTAKTQ PREEQFNGTY RVVSVLPIGH QDWLKGKQFT CKVNNKALPS PIERTISKAR   360
GQAHQPSVYV LPPSREELSK NTVSLTCLIK DFFPPDIDVE WQSNGQQEPE SKYRTTPPQL   420
DEDGSYFLYS KLSVDKSRWQ RGDTFICAVM HEALHNHYTQ ESLSHSPGK              469

SEQ ID NO: 13           moltype = DNA  length = 1407
FEATURE                 Location/Qualifiers
misc_feature            1..1407
                        note = A1mut2 heavy chain full-length cIgG2
source                  1..1407
                        mol_type = other DNA
                        organism = synthetic construct
SEQUENCE: 13
atgtacagga tgcaactcct gtcttgcatt gcactaagtc ttgcacttgt cacgaattcg    60
gaggtgcagc tggtggagac cggggggagac ctggtgaagc ctggcgggtc cctgagattg   120
tcctgtgtgg cctctggatt ctccttcagc agttatgcca tgaactgggt ccgccaggct   180
cctgagaagg ggctgcagct ggtgggcggt attaatagcg gtggaagtag tacatattac   240
accgacgctg tgaagggccg cttcaccatc tccagagaca acgccaagaa cacagtgtat   300
ttacagatga atagcctgag agccgaggac acggccgtgt attactgtgc gattagtaat   360
tgggcctact ggggccaggg aaccctggtc accgtctcct cagctagcac cacggccccc   420
tcggttttcc cactggcccc cagctgcggg tccttccg gctccacggt ggccctggcc      480
tgcctggtgt caggctactt ccccgagcct gtaactgtgt cctggaactc cggctccttg   540
accagcggtg tgcacacctt cccgtccgtc ctgcagtcct cagggctcta ctccctcagc   600
agcatggtga cagtgccctc agcaggtgg cccagcgaga ccttcacctg caacgtggcc     660
cacccggcca gcaaaactaa gtagacaag ccagtgccca aagagaaaa tggaagagtt     720
cctcgcccac ctgattgtcc caaatgccca gcccctgaaa tgctgggagg ccttcggtc    780
ttcatctttc ccccgaaacc caaggacacc ctcttgattg cccgaacact tgaggtcaca   840
tgtgtggtgg tggatctgga cccagaagac cctgaggtgc agatcagtc gttcgtggat   900
ggtaagcaga tgcaaacagc caagactcag cctcgtgagg agcagttcaa tggcacctac   960
cgtgtggtca gtgtcctccc cattgggcac caggactggc tcaagggaa gcagttcacg   1020
tgcaaagtca caacaaagc cctcccatcc ccgatcgaga ggaccatctc aaggccaga     1080
gggcaggccc atcagcccag tgtgtatgtc ctgccgccat ccgggagga gttgagcaag   1140
aacacagtta cttgacatg cctgatcaaa gacttcttcc cacctgacat tgatgtggag   1200
tggcagagca atggacagca ggagcctgag agcaagtacc gcacgacccc gcccagctgg  1260
gacgaggacg gtcctacttc ctgtacagc aagctctctg tggacaagag ccgctggcag   1320
cggggagaca ccttcatatg tgcggtgatg catgaagctc tacacaacca ctacacacag  1380
gaatccctct cccattctcc gggtaaa                                      1407
```

```
SEQ ID NO: 14              moltype = AA   length = 467
FEATURE                    Location/Qualifiers
REGION                     1..467
                           note = A1mut2 heavy chain full-length cIgG3
source                     1..467
                           mol_type = protein
                           organism = synthetic construct
SEQUENCE: 14
MYRMQLLSCI ALSLALVTNS EVQLVETGGD LVKPGGSLRL SCVASGFSFS SYAMNWVRQA   60
PEKGLQLVGG INSGGSSTYY TDAVKGRFTI SRDNAKNTVY LQMNSLRAED TAVYYCAISN  120
WAYWGQGTLV TVSSASTTAP SVFPLAPSCG SQSGSTVALA CLVSGYIPEP VTVSWNSGSL  180
TSGVHTFPSI LQSSGLYSLS SMVTVPSSRW PSETFTCNVA HPATNTKVDK PVVKECECKC  240
NCNNCPCPGC GLLGGPSVFI FPPKPKDILV TARTPTVTCV VVDLDPENPE VQISWFVDSK  300
QVQTANTQPR EEQSNGTYRV VSVLPIGHQD WLSGKQFKCK VNNKALPSPI EEIISKTPGQ  360
AHQPNVYVLP PSRDEMSKNT VTLTCLVKDF FPPEIDVEWQ SNGQQEPESK YRMTPPQLDE  420
DGSYFLYSKL SVDKSRWQRG DTFICAVMHE ALHNHYTQKS LSHSPGK               467

SEQ ID NO: 15              moltype = DNA   length = 1401
FEATURE                    Location/Qualifiers
misc_feature               1..1401
                           note = A1mut2 heavy chain full-length cIgG3
source                     1..1401
                           mol_type = other DNA
                           organism = synthetic construct
SEQUENCE: 15
atgtacagga tgcaactcct gtcttgcatt gcactaagtc ttgcacttgt cacgaattcg   60
gaggtgcagc tggtggagac cggggggagac ctggtgaagc ctggcgggtc cctgagattg  120
tcctgtgtgg cctctggatt ctccttcagc agttatgcca tgaactgggt ccgccaggct  180
cctgagaagg ggctgcagct ggtgggcggt attaatagcg gtggaagtag tacatattac  240
accgacgctg tgaagggccg cttcaccatc tccagagaca acgccaagaa cacagtgtat  300
ttacagatga atagcctgag agccgaggac acgccgtgt attactgtgc gattagtaat   360
tgggcctact ggggccaggg aaccctggtc accgtctcct cagctagcac cacggccccc  420
tcggttttcc cactggcccc cagctgtggg tcccaatccg gctccacggt ggccctggcc  480
tgcctggtgt caggctacat cccgagcct gtaactgtgt cctggaactc cggctccttg   540
accagcggtg tgcacacctt cccgtccatc ctgcagtcct cagggctcta ctccctcagc  600
agcatggtga cagtgccctc cagcaggtgg cccagcgaga ccttcacctg caatgtggcc  660
cacccggcca ccaacactaa agtagacaag ccagtggtca agaatgcga gtgcaagtgt   720
aactgtaaca actgcccatg cccaggttgt ggcctgctgg gagggccttc ggtcttcatc  780
tttccccca aacccaagga catcctcgtg actgcccgga caccacagt cactttgtg   840
gtggtggatc tggaccccga aaaccctgag gtgcagatca gctggttcgt ggatagtaag  900
caggtgcaaa cagccaacac gcagcctcgt gaggagcagt ccaatggcac ctaccgtgtg  960
gtcagtgtcc tccccattgg caccaggac tggctttcag ggaagcagtt caagtgcaaa 1020
gtcaacacaa aagccctccc atcccccatt gaggagatca tctccaagac ccagggtcag 1080
gcccatcagc ctaatgtgta tgtcctgccc ccatcgcggg atgagatgag caagaatacg 1140
gtcaccctga cctgtctggt caaagacttc ttcccacctg agattgatgt ggagtggcag 1200
agcaatggac agcaggagcc tgagagcaag taccgcatga cccgccca gctggatgag 1260
gatgggtcct acttcctata cagcaagctc tctgtggaca gagccgctg gcagcgggga 1320
gacaccttca tatgtgcggt gatgcatgaa gctctacaca accactacac acagaaatcc 1380
ctctcccatt ctccgggtaa a                                          1401

SEQ ID NO: 16              moltype = AA   length = 465
FEATURE                    Location/Qualifiers
REGION                     1..465
                           note = A1mut2 heavy chain full-length cIgG4
source                     1..465
                           mol_type = protein
                           organism = synthetic construct
SEQUENCE: 16
MYRMQLLSCI ALSLALVTNS EVQLVETGGD LVKPGGSLRL SCVASGFSFS SYAMNWVRQA   60
PEKGLQLVGG INSGGSSTYY TDAVKGRFTI SRDNAKNTVY LQMNSLRAED TAVYYCAISN  120
WAYWGQGTLV TVSSASTTAP SVFPLAPSCG STSGSTVALA CLVSGYFPEP VTVSWNSGSL  180
TSGVHTFPSV LQSSGLYSLS SMVTVPSSRW PSETFTCNVV HPASNTKVDK PVPKESTCKC  240
ISPCPVPESL GGPSVFIFPP KPKDILRITR TPEITCVVLD LGREDPEVQI SWFVDGKEVH  300
TAKTQPREQQ FNSTYRVVSV LPIEHQDWLT GKEFKCRVNH IGLPSPIERT ISKARGQAHQ  360
PSVYVLPPSP KELSSSDTVT LTCLIKDFFP PEIDVEWQSN GQPEPESKYH TTAPQLDEDG  420
SYFLYSKLSV DKSRWQQGDP FTCAVMHEAL QNHYTDLSLS HSPGK                465

SEQ ID NO: 17              moltype = DNA   length = 1395
FEATURE                    Location/Qualifiers
misc_feature               1..1395
                           note = A1mut2 heavy chain full-length cIgG4
source                     1..1395
                           mol_type = other DNA
                           organism = synthetic construct
SEQUENCE: 17
atgtacagga tgcaactcct gtcttgcatt gcactaagtc ttgcacttgt cacgaattcg   60
gaggtgcagc tggtggagac cggggggagac ctggtgaagc ctggcgggtc cctgagattg  120
tcctgtgtgg cctctggatt ctccttcagc agttatgcca tgaactgggt ccgccaggct  180
cctgagaagg ggctgcagct ggtgggcggt attaatagcg gtggaagtag tacatattac  240
```

```
accgacgctg tgaagggccg cttcaccatc tccagagaca acgccaagaa cacagtgtat  300
ttacagatga atagcctgag agccgaggac acgccgtgt attactgtgc gattagtaat  360
tgggcctact ggggccaggg aaccctggtc accgtctcct cagctagcac acggccccc  420
tcggttttcc cactggcccc cagctgcggg tccacttccg gctccacggt ggccctagc  480
tgcctggtgt caggctactt ccccgagcct gtaactgtgt cctggaactc cggctccttg  540
accagcggtg tgcacacctt cccgtccgtc ctgcagtcct cagggctcta ctccctcagc  600
agcatggtga cagtgccctc cagcaggtgg cccagcgaga ccttcacctg caacgtggtc  660
cacccggcca gcaacactaa agtagacaag ccagtgccca agagtccac ctgcaagtgt  720
atatcccccat gcccagtccc tgaatcactg ggagggcctt cggtcttcat ctttcccccg  780
aaacccaagg acatcctcag gattacccga cacccgaga tcacctgtgt ggtgttagat  840
ctgggccgtg aggaccctga ggtgcagatc agctggttcg tggatggtaa ggaggtgcac  900
acagccaaga cgcagcctcg tgagcagcag ttcaacagca cctaccgtgt ggtcagcgtc  960
ctccccattg agcaccagga ctggctcacc ggaaaggagt tcaagtgcag agtcaaccac  1020
ataggcctcc cgtccccat cgagaggacc atctccaag ccagagggca gcccatcag  1080
cccagtgtgt atgtcctgcc accatcccca aaggagttgt catccagtga cacggtcacc  1140
ctgacctgcc tgatcaaaga cttcttccca cctgagattg atgtggagtg gcagagcaat  1200
ggacagccag agcctgagag caagtaccac acgactgcac cccagctgga cgaggacggg  1260
tcctacttcc tgtacagcaa gctctctgtg acaagagcc gctggcagca gggagacccc  1320
ttcacatgtg cggtgatgca tgaagctcta cagaaccact acacagatct atccctctcc  1380
cattctccgg gtaaa                                                   1395

SEQ ID NO: 18          moltype = AA  length = 236
FEATURE                Location/Qualifiers
REGION                 1..236
                       note = A1mut2 lambda light chain full-length
source                 1..236
                       mol_type = protein
                       organism = synthetic construct
SEQUENCE: 18
MYRMQLLSCI ALSLALVTNS QAVLNQPASV SGSLGQRVTI SCTGSSSDIG KSYVAWYQQL  60
PGTGPRTLIN VDGNRASGVP DRFSVSRSGN TATLTISGLQ AEDEADYHCS SWDWSLHTYV  120
FGSGTQLTIL GQPKASPSVT LFPPSSEELG ANKATLVCLI SDFYPSGVTV AWKADGSPIT  180
QGVETTKPSK QSNNKYAASS YLSLTPDKWK SHSSFSCLVT HEGSTVEKKV APAECS     236

SEQ ID NO: 19          moltype = DNA  length = 709
FEATURE                Location/Qualifiers
misc_feature           1..709
                       note = A1mut2 lambda light chain full-length
source                 1..709
                       mol_type = other DNA
                       organism = synthetic construct
SEQUENCE: 19
atgtacagga tgcaactcct gtcttgcatt gcactaagtc ttgcacttgt cacgaattcg  60
caggctgtgc tgaatcagcc ggcctcagtg tccgggtccc tgggccagag ggtcaccatc  120
tcctgcactg gaagcagctc cgacatcggt aaaagttatg tggcctggta ccagcagctc  180
ccgggaacag gccccagaac cctcatcaat gttgatggta accgagcctc aggggtcccc  240
gatcgattct ctgtctccag gtcaggcaac acagcctcc tgaccatctc ggggctccag  300
gctgaggatg aggctgatta tcactgctca tcctgggact ggagtctcca tacttacgtg  360
ttcggctcag ggacccagct gaccatccta ggtcagccca aggcctcccc ctcggtcaca  420
ctcttcccgc cctcctctga ggagctcggc gccaacaagg ccaccctggt gtgcctcatc  480
agcgacttct accccagcgg cgtgacggtg gcctggaagg cagacggcag ccccatcacc  540
cagggcgtgg agaccaccaa gccctccaag cagagcaaca acaagtacgc ggccagcagc  600
tacctgagcc tgacgcctga caagtggaaa tctcacagca gcttcagctg cctggtcacg  660
cacgagggga gcaccgtgga agaagaaggtg ccccccgcag agtgctctt              709

SEQ ID NO: 20          moltype = AA  length = 8
FEATURE                Location/Qualifiers
REGION                 1..8
                       note = D5 HCDR1
source                 1..8
                       mol_type = protein
                       organism = synthetic construct
SEQUENCE: 20
GFTFSSYS                                                           8

SEQ ID NO: 21          moltype = AA  length = 8
FEATURE                Location/Qualifiers
REGION                 1..8
                       note = D5 HCDR2
source                 1..8
                       mol_type = protein
                       organism = synthetic construct
SEQUENCE: 21
INSGGSST                                                           8

SEQ ID NO: 22          moltype = AA  length = 7
FEATURE                Location/Qualifiers
REGION                 1..7
                       note = D5 HCDR3
```

```
source                         1..7
                               mol_type = protein
                               organism = synthetic construct
SEQUENCE: 22
VISNWSY                                                                          7

SEQ ID NO: 23                  moltype = AA  length = 9
FEATURE                        Location/Qualifiers
REGION                         1..9
                               note = D5 LCDR1
source                         1..9
                               mol_type = protein
                               organism = synthetic construct
SEQUENCE: 23
ATNVGGGYD                                                                        9

SEQ ID NO: 24                  moltype = AA  length = 11
FEATURE                        Location/Qualifiers
REGION                         1..11
                               note = D5 LCDR3
source                         1..11
                               mol_type = protein
                               organism = synthetic construct
SEQUENCE: 24
SSWDNSLTAY V                                                                    11

SEQ ID NO: 25                  moltype = AA  length = 114
FEATURE                        Location/Qualifiers
REGION                         1..114
                               note = D5 VH
source                         1..114
                               mol_type = protein
                               organism = synthetic construct
SEQUENCE: 25
EVQLVETGGD LMKPGGSLRL SCVASGFTFS SYSMSWVRQA PEKGLQLVAG INSGGSSTYY                60
TDAVKGRFTI SRDNAKNTLY LQMNSLRDED TAVYYCVISN WSYWGQGTLV TVSS                     114

SEQ ID NO: 26                  moltype = DNA  length = 342
FEATURE                        Location/Qualifiers
misc_feature                   1..342
                               note = D5 VH
source                         1..342
                               mol_type = other DNA
                               organism = synthetic construct
SEQUENCE: 26
gaggtgcagc tggtggagac tggggggagac ctgatgaagc tggggggtc cctgagactg               60
tcctgtgtgg cctctggatt caccttcagt agctacagta tgagttgggt ccgccaggct              120
cctgagaagg ggctgcagtt ggtcgcaggt attaacagcg gtggaagtag cacatactac              180
acagacgctg tgaagggccg attcaccatc tccagagaca cgccaagaa cacgctgtat              240
ctgcagatga acagtctgag agatgaagac acggcagtct attattgtgt gatcagtaat              300
tggtcctact ggggccaggg aaccctggtc accgtctcct ca                                 342

SEQ ID NO: 27                  moltype = AA  length = 111
FEATURE                        Location/Qualifiers
REGION                         1..111
                               note = D5 VL
source                         1..111
                               mol_type = protein
                               organism = synthetic construct
SEQUENCE: 27
QPVLTQPPSV SAALGQRVTI SCTGTATNVG GGYDVQWYQQ FPGRPPKTII YGNYNRPSGV                60
PDRFSASTSG TTATLTISGL QAEDEANYYC SSWDNSLTAY VFGSGTQLTI L                       111

SEQ ID NO: 28                  moltype = DNA  length = 333
FEATURE                        Location/Qualifiers
misc_feature                   1..333
                               note = D5 VL
source                         1..333
                               mol_type = other DNA
                               organism = synthetic construct
SEQUENCE: 28
cagcctgtgc tcactcagcc gccctctgtg tctgcggccc tgggacagag ggtcaccatc               60
tcctgcactg gaactgcgac caacgtcggc ggcggttatg atgtacaatg gtaccagcag              120
tttccaggaa gacccccccta aaactatcatt tacggtaatay acaatcgccc ctcggggggtc          180
ccagatcgat tctctgcctc cacgtcaggc accacagcca ccctgaccat ctctgggctc              240
caggctgagg atgaggctaa ttattactgc tcatcgtggg acaacagtct cactgcttac              300
gttttcggct cagggaccca gctgaccatc ctc                                           333

SEQ ID NO: 29                  moltype = AA  length = 277
```

```
FEATURE                 Location/Qualifiers
REGION                  1..277
                        note = D5 scFv
source                  1..277
                        mol_type = protein
                        organism = synthetic construct
SEQUENCE: 29
QPVLTQPPSV SAALGQRVTI SCTGTATNVG GGYDVQWYQQ FPGRPPKTII YGNYNRPSGV    60
PDRFSASTSG TTATLTISGL QAEDEANYYC SSWDNSLTAY VFGSGTQLTI LGGGSSRSSS   120
SGGGGSGGGG EVQLVETGGD LMKPGGSLRL SCVASGFTFS SYSMSWVRQA PEKGLQLVAG   180
INSGGSSTYY TDAVKGRFTI SRDNAKNTLY LQMNSLRDED TAVYYCVISN WSYWGQGTLV   240
TVSSESPSPP NLTSGQAGQH HHHHHGAYPY DVPDYAS                            277

SEQ ID NO: 30           moltype = DNA  length = 831
FEATURE                 Location/Qualifiers
misc_feature            1..831
                        note = D5 scFv
source                  1..831
                        mol_type = other DNA
                        organism = synthetic construct
SEQUENCE: 30
cagcctgtgc tcactcagcc gccctctgtg tctgcggccc tgggacagag ggtcaccatc    60
tcctgcactg gaactgcgac caacgtcggg ggcggttatg atgtacaatg gtaccagcag   120
tttccaggaa gacccctaa  aactatcatt tacggtaatt acaatcgccc tcgggggtc    180
ccagatcgat tctctgcctc cacgtcaggc accacagcca cctgaccat  ctctgggctc   240
caggctgagg atgaggctaa ttattactgc tcatcgtgac acaacagtct cactgcttac   300
gttttcggct cagggaccca gctgaccatc ctcggcggtg ttcctctag  atcttcctcc   360
tctggtggcg gtggctcggg cggtggtggg gaggtgcagc tggtggagac tggggggagac  420
ctgatgaagc tggggggtc  cctgagactg tcctgtgtgg cctctggatt caccttcagt   480
agctacagta tgagttgggt ccgccaggct cctgagaagg gctcagttt  ggtcgcaggt   540
attaacagcg gtgaagtag  cacatactac acagacgctg tgaagggccg attcaccatc   600
tccagagaca cgccaagaa  cacgctgtat ctgcagatga cagtctgag  agatgaagac   660
acggcagtct attattgtgt gatcagtaat tggtcctact ggggccaggg aaccctggtc   720
accgtctcct cagagagtcc atcccctcca aacctcacta gtggccaggc cggccagcac   780
catcaccatc accatggcgc ataccgtac  gacgttccgg actacgcttc t            831

SEQ ID NO: 31           moltype = AA  length = 465
FEATURE                 Location/Qualifiers
REGION                  1..465
                        note = D5 heavy chain full-length cIgG1
source                  1..465
                        mol_type = protein
                        organism = synthetic construct
SEQUENCE: 31
MYRMQLLSCI ALSLALVTNS EVQLVETGGD LMKPGGSLRL SCVASGFTFS SYSMSWVRQA    60
PEKGLQLVAG INSGGSSTYY TDAVKGRFTI SRDNAKNTLY LQMNSLRDED TAVYYCVISN   120
WSYWGQGTLV TVSSASTTAP SVFPLAPSCG STSGSTVALA CLVSGYFPEP VTVSWNSGSL   180
TSGVHTFPSV LQSSGLYSLS SMVTVPSSRW PSETFTCNVV HPASNTKVDK PVFNECRCTD   240
TPPCPVPEPL GGPSVLIFPP KPKDILRITR TPEVTCVVLD LGREDPEVQI SWFVDGKEVH   300
TAKTQSREQQ FNGTYRVVSV LPIEHQDWLT GKEFKCRVNH IDLPSPIERT ISKARGRAHK   360
PSVYVLPPSP KELSSSDTVS VTCLIKDFYP PDIDVEWQSN GQQEPERKHR MTPPQLDEDG   420
SYFLYSKLSV DKSRWQQGDP FTCAVMHETL QNHYTDLSLS HSPGK                   465

SEQ ID NO: 32           moltype = DNA  length = 1395
FEATURE                 Location/Qualifiers
misc_feature            1..1395
                        note = D5 heavy chain full-length cIgG1
source                  1..1395
                        mol_type = other DNA
                        organism = synthetic construct
SEQUENCE: 32
atgtacagga tgcaactcct gtcttgcatt gcactaagtc ttgcacttgt cacgaattcg    60
gaggtgcagc tggtggagac tggggggagac ctgatgaagc tggggggtc  cctgagactg   120
tcctgtgtgg cctctggatt caccttcagt agctacagta tgagttgggt ccgccaggct   180
cctgagaagg gctcagttt  ggtcgcaggt attaacagcg gtgaagtag  cacatactac   240
acagacgctg tgaagggccg attcaccatc tccagagaca cgccaagaa  cacgctgtat   300
ctgcagatga cagtctgag  agatgaagac acggcagtct attattgtgt gatcagtaat   360
tggtcctact ggggccaggg aaccctggtc accgtctcct cagctagcac cacgccccc   420
tcggttttcc cactggcccc ctccacttgg gctccacgtg cctccacgag ggccatcctg   480
tgcctggtgt caggctactt ccccgagcct gtaactgtgt cctgaactc  cggctccttg   540
accagcggtg tgcacacctt cccgtccgtc ctgcagtcct cagggctcta ctcccctcag   600
agcatggtga cagtgccctc cagcagatgg cccagtgaga ccttcacctg aacgtggtc    660
caccccggcca gcaacactaa agtagacaag ccagtgttca tgaatgcag  atgcactgat   720
acaccccat  gcccctgtcc tgaacctctg ggaggcccct cgtcctcat  ctttccccca   780
aaacccaagg acatcctcag gattacccga acacccgagg tcacctgtgt ggttgtagat   840
ctgggccgtg aggaccctga ggtgcagatc agctggttcg tggatggtaa ggaggtgcac   900
acagccaaga cgcagtctcg tgagcagcag ttcaacggca cctaccgtgt ggtcagcgtc   960
ctccccattg agcaccagga ctggctcaca ggaaaggagt tcaagtgcag agtcaaccac  1020
atagacctcc catctcccat cgagaggacc atctctaagg ccagagggag ggcccataag  1080
```

```
cccagtgtgt atgtcctgcc accatcccca aaggagttgt catccagtga cacagtcagc   1140
gtcacctgcc tgataaaaga cttctaccca cctgacattg atgtggagtg cagagcaat    1200
ggacagcagg agcctgagag gaagcaccgc atgaccccgc cccagctgga cgaggacggg   1260
tcctacttcc tgtacagcaa gctctctgtg acaagagcc gctggcagca gggagacccc    1320
ttcacatgtg cggtgatgca tgaaactcta cagaaccact acacagatct atccctctcc   1380
cattctccgg gtaaa                                                    1395
```

| | | |
|---|---|---|
| SEQ ID NO: 33 | moltype = AA length = 237 | |
| FEATURE | Location/Qualifiers | |
| REGION | 1..237 | |
| | note = D5 lambda light chain full-length | |
| source | 1..237 | |
| | mol_type = protein | |
| | organism = synthetic construct | |

```
SEQUENCE: 33
MYRMQLLSCI ALSLALVTNS QPVLTQPPSV SAALGQRVTI SCTGTATNVG GGYDVQWYQQ    60
FPGRPPKTII YGNYNRPSGV PDRFSASTSG TTATLTISGL QAEDEANYYC SSWDNSLTAY   120
VFGSGTQLTI LGQPKASPSV TLFPPSSEEL GANKATLVCL ISDFYPSGVT VAWKADGSPI   180
TQGVETTKPS KQSNNKYAAS SYLSLTPDKW KSHSSFSCLV THEGSTVEKK VAPAECS      237
```

| | | |
|---|---|---|
| SEQ ID NO: 34 | moltype = DNA length = 712 | |
| FEATURE | Location/Qualifiers | |
| misc_feature | 1..712 | |
| | note = D5 lambda light chain full-length | |
| source | 1..712 | |
| | mol_type = other DNA | |
| | organism = synthetic construct | |

```
SEQUENCE: 34
atgtacagga tgcaactcct gtcttgcatt gcactaagtc ttgcacttgt cacgaattcg    60
cagcctgtgc tcactcagcc gccctctgtg tctgcgggcc tgggacagag ggtcaccatc   120
tcctgcactg gaactgcgac caacgtcggg ggcggttatg atgtacaatg gtaccagcag   180
tttccaggaa gaccccctaa aactatcatt tacggtaatt acaatcgccc ctcgggggtc   240
ccagatcgat tctctgcctc cacgtcaggc accacagcca cctgaccat ctctgggctc    300
caggctgagg atgaggctaa ttattactgc tcatcgtggg acaacagtct cactgcttac   360
gttttcggct cagggaccca gctgaccatc ctcggtcagc ccaaggcctc ccctctcggtc   420
acactcttcc cgccctcctc tgaggagctc ggcgccaaca aggccaccct ggtgtgcctc   480
atcagcgact tctaccccag cggcgtgacg gtggcctgga aggcagacgg cagcccatc    540
acccagggcg tggagaccac caagccctcc aagcagagca caacaagta cgcggccagc    600
agctacctga gcctgacgcc tgacaagtgg aaatctcaca gcagcttcag ctgcctggtc    660
acgcacgagg ggagcaccgt ggagaagaag gtggcccccg cagagtgctc tt            712
```

| | | |
|---|---|---|
| SEQ ID NO: 35 | moltype = AA length = 8 | |
| FEATURE | Location/Qualifiers | |
| REGION | 1..8 | |
| | note = B10 HCDR1 | |
| source | 1..8 | |
| | mol_type = protein | |
| | organism = synthetic construct | |

```
SEQUENCE: 35
GFTFSDYP                                                              8
```

| | | |
|---|---|---|
| SEQ ID NO: 36 | moltype = AA length = 8 | |
| FEATURE | Location/Qualifiers | |
| REGION | 1..8 | |
| | note = B10 HCDR2 | |
| source | 1..8 | |
| | mol_type = protein | |
| | organism = synthetic construct | |

```
SEQUENCE: 36
INSGGSAT                                                              8
```

| | | |
|---|---|---|
| SEQ ID NO: 37 | moltype = AA length = 7 | |
| FEATURE | Location/Qualifiers | |
| REGION | 1..7 | |
| | note = B10 HCDR3 | |
| source | 1..7 | |
| | mol_type = protein | |
| | organism = synthetic construct | |

```
SEQUENCE: 37
ATSNFQY                                                               7
```

| | | |
|---|---|---|
| SEQ ID NO: 38 | moltype = AA length = 9 | |
| FEATURE | Location/Qualifiers | |
| REGION | 1..9 | |
| | note = B10 LCDR1 | |
| source | 1..9 | |
| | mol_type = protein | |
| | organism = synthetic construct | |

```
SEQUENCE: 38
```

```
NTNIGSPYD                                                                        9

SEQ ID NO: 39             moltype = AA  length = 11
FEATURE                   Location/Qualifiers
REGION                    1..11
                          note = B10 LCDR3
source                    1..11
                          mol_type = protein
                          organism = synthetic construct
SEQUENCE: 39
QSYDDNVDGY V                                                                    11

SEQ ID NO: 40             moltype = AA  length = 114
FEATURE                   Location/Qualifiers
REGION                    1..114
                          note = B10 VH
source                    1..114
                          mol_type = protein
                          organism = synthetic construct
SEQUENCE: 40
EVQLVETGGD LVKPGGSLRL SCVASGFTFS DYPMNWVRQA PEKGLQLVGG INSGGSATYY               60
TDAVKGRFTI SRDNAKNTVY LQMNSLRAED TAMYYCATSN FQYWGQGTLV TVSS                    114

SEQ ID NO: 41             moltype = DNA  length = 342
FEATURE                   Location/Qualifiers
misc_feature              1..342
                          note = B10 VH
source                    1..342
                          mol_type = other DNA
                          organism = synthetic construct
SEQUENCE: 41
gaggtgcagc tggtggagac tgggggagat ctggtgaagc ctgggggatc cctgagactc               60
tcttgtgtgg cctctggatt caccttcagt gactacccca tgaactgggt ccgccaggct              120
cctgagaagg ggctgcagtt ggtcggtggt attaacagcg gtggaagtgc tacatactac              180
acagacgctg tgaagggccg attcaccatc tccagagaca acgccaagaa cacagtgtat              240
ctgcagatga acagcctgag agccgaggac acggccatgt attactgtgc aacgtctaat              300
tttcagtact ggggccaggg aaccctggtc accgtctcct ca                                 342

SEQ ID NO: 42             moltype = AA  length = 108
FEATURE                   Location/Qualifiers
REGION                    1..108
                          note = B10 VL
source                    1..108
                          mol_type = protein
                          organism = synthetic construct
SEQUENCE: 42
QAVLNQPASV SAALGQRVTI SCNTNIGSPY DVQWYQQLPG KSPKTIIYGN SNRPSGVPVR               60
FSGSKSGSTA TLTIAGIQAE DEADYYCQSY DDNVDGYVFG SGTQLTVL                          108

SEQ ID NO: 43             moltype = DNA  length = 324
FEATURE                   Location/Qualifiers
misc_feature              1..324
                          note = B10 VL
source                    1..324
                          mol_type = other DNA
                          organism = synthetic construct
SEQUENCE: 43
caggctgtgc tgaatcagcc ggcctctgtg tctgcagccc tggggcagag ggtcaccatc               60
tcctgtaaca ccaacatcgg cagtccttat gatgtacaat ggtaccagca gctcccagga              120
aagtccccta aaactatcat ttatggtaat agcaatcgac cctcgggggt cccggttcga              180
ttctctggct ccaagtcagg cagcacagcc accctgacca tcgctgggat ccaggctgag              240
gatgaggctg attattactg ccagtcctat gatgacaacg tcgatggtta cgtgttcggc              300
tcagggaccc aactgaccgt cctt                                                     324

SEQ ID NO: 44             moltype = AA  length = 274
FEATURE                   Location/Qualifiers
REGION                    1..274
                          note = B10 scFv
source                    1..274
                          mol_type = protein
                          organism = synthetic construct
SEQUENCE: 44
QAVLNQPASV SAALGQRVTI SCNTNIGSPY DVQWYQQLPG KSPKTIIYGN SNRPSGVPVR               60
FSGSKSGSTA TLTIAGIQAE DEADYYCQSY DDNVDGYVFG SGTQLTVLGG GSSRSSSSGG              120
GGSGGGGEVQ LVETGDDLVK PGGSLRLSCV ASGFTFSDYP MNWVRQAPEK GLQLVGGINS              180
GGSATYYTDA VKGRFTISRD NAKNTVYLQM NSLRAEDTAM YYCATSNFQY WGQGTLVTVS              240
SESPSPPNLT SGQAGQHHHH HHGAYPYDVP DYAS                                         274

SEQ ID NO: 45             moltype = DNA  length = 822
```

```
FEATURE                 Location/Qualifiers
misc_feature            1..822
                        note = B10 scFv
source                  1..822
                        mol_type = other DNA
                        organism = synthetic construct
SEQUENCE: 45
caggctgtgc tgaatcagcc ggcctctgtg tctgcagccc tggggcagag ggtcaccatc    60
tcctgtaaca ccaacatcgg cagtccttat gatgtacaat ggtaccagca gctcccagga   120
aagtccccta aaactatcat ttatggtaat agcaatcgac cctcgggggt cccggttcga   180
ttctctggct ccaagtcagg cagcacagcc accctgacca tcgctgggat ccaggctgag   240
gatgaggctg attattactg ccagtcctat gatgacaacg tcgatggtta cgtgttcggc   300
tcagggaccc aactgaccgt ccttggcggt ggttcctcta gatcttcctc ctctggtggc   360
ggtggctcgg gcggtggtgg ggaggtgcag ctggtggaga ctggtggagg tctggtgaag   420
cctgggggat ccctgagact ctcttgtgtg gcctctggat tcaccttcag tgactacccc   480
atgaactggg tccgccaggc tcctgagaag gggctgcagt tggtcggtgg tattaacagc   540
ggtggaagtg ctacatacta cacagacgct gtgaagggcc gattcaccat ctccagagac   600
aacgccaaga acacagtgta tctgcagatg aacagcctga gagccgagga cacggccatg   660
tattactgtg caacgtctaa ttttcagtac tggggccagg gaaccctggt caccgtctcc   720
tcagagagtc catcccctcc aaacctcact agtggccagg ccggccagca ccatcaccat   780
caccatggcg cataccccgta cgacgttccg gactacgctt ct                     822

SEQ ID NO: 46           moltype = AA  length = 465
FEATURE                 Location/Qualifiers
REGION                  1..465
                        note = B10 heavy chain full-length cIgG1
source                  1..465
                        mol_type = protein
                        organism = synthetic construct
SEQUENCE: 46
MYRMQLLSCI ALSLALVTNS EVQLVETGGD LVKPGGSLRL SCVASGFTFS DYPMNWVRQA    60
PEKGLQLVGG INSGGSATYY TDAVKGRFTI SRDNAKNTVY LQMNSLRAED TAMYYCATSN   120
FQYWGQGTLV TVSSASTTAP SVFPLAPSCG STSGSTVALA CLVSGYFPEP VTVSWNSGSL   180
TSGVHTFPSV LQSSGLYSLS SMVTVPSSRW PSETFTCNVV HPASNTKVDK PVFNECRCTD   240
TPPCPVPEPL GGPSVLIFPP KPKDILRITR TPEVTCVVLD LGREDPEVQI SWFVDGKEVH   300
TAKTQSREQQ FNGTYRVVSV LPIEHQDWLT GKEFKCRVNH IDLPSPIERT ISKARGRAHK   360
PSVYVLPPSP KELSSSDTVS VTCLIKDFYP PDIDVEWQSN GQQEPERKHR MTPPQLDEDG   420
SYFLYSKLSV DKSRWQQGDP FTCAVMHETL QNHYTDLSLS HSPGK                   465

SEQ ID NO: 47           moltype = DNA  length = 1395
FEATURE                 Location/Qualifiers
misc_feature            1..1395
                        note = B10 heavy chain full-length cIgG1
source                  1..1395
                        mol_type = other DNA
                        organism = synthetic construct
SEQUENCE: 47
atgtacagga tgcaactcct gtcttgcatt gcactaagtc ttgcacttgt cacgaattcg    60
gaggtgcagc tggtggagac tgggggagat ctggtgaagc ctgggggatc cctgagactc   120
tcttgtgtgg cctctggatt caccttcagt gactacccca tgaactgggt ccgccaggct   180
cctgagaagg ggctgcagtt ggtcggtggt attaacagcg gtggaagtgc tacatactac   240
acagacgctg tgaagggccg attcaccatc tccagagaca acgccaagaa cacagtgtat   300
ctgcagatga acagcctgag agccgaggac acggccatgt attactgtgc aacgtctaat   360
tttcagtact ggggccaggg aaccctggtc accgtctcct cagctagcac cacggccccc   420
tcggttttcc cactggcccc cagctgcggg tccacttccg gctccacggt ggccctgagc   480
tgcctggtgt caggctactt ccccgagcct gtaactgtgt cctggaactc cggctccttg   540
accagcggtg tgcacacctt cccgtccgtc ctgcagtcct cagggctcta ctcccctcagc   600
agcatggtga gtgcccctc agcagatggg cccagtgaga ccttcacctg caacgtggtc   660
caccggcca gcaacactaa agtagacaag ccagtgttca tgaatgagtg cactgat       720
acacccccat gcccagtccc tgaacctctg gagggccttc ggtcctcat cttttcccccg   780
aaacccaagg acatcctcag gattaccga cacccgagg tcacctgtgt ggtgttagat   840
ctgggccgtg aggaccctga ggtgcagatc agctggttcg tggatggtaa ggaggtgcac   900
acagccaaga cgcagtctcg tgagcagcag ttcaacggca cctaccgtgt ggtcagcgtc   960
ctccccattg agcaccagga ctggctcaca gggaaggatt caaggtgaag gtcaaccac  1020
atagacctcc catctcccat cgagaggacc atctctaagg ccagaggagg gcccataag  1080
cccagtgtgt atgtcctgcc accatcccca aaggagttgt catccagtga cacagtcagc  1140
gtcacctgcc tgataaaaga cttctaccca cctgacattg atgtggagtg gcagagcaat  1200
ggacagcagg agcctgagag gaagcaccgc atgaccccgc ccagctggag cgaggacggg  1260
tcctacttcc tgtacagcaa gctctctgtg gacaagagcg gctggcagca gggagacccc  1320
ttcacatgtg cggtgatgca tgaaactcta cagaaccact acacagatct atccctctcc  1380
cattctccgg gtaaa                                                   1395

SEQ ID NO: 48           moltype = AA  length = 234
FEATURE                 Location/Qualifiers
REGION                  1..234
                        note = B10 lambda light chain full-length
source                  1..234
                        mol_type = protein
                        organism = synthetic construct
```

```
SEQUENCE: 48
MYRMQLLSCI ALSLALVTNS QAVLNQPASV SAALGQRVTI SCNTNIGSPY DVQWYQQLPG    60
KSPKTIIYGN SNRPSGVPVR FSGSKSGSTA TLTIAGIQAE DEADYCQSY DDNVDGYVFG    120
SGTQLTVLGQ PKASPSVTLF PPSSEELGAN KATLVCLISD FYPSGVTVAW KADGSPITQG   180
VETTKPSKQS NNKYAASSYL SLTPDKWKSH SSFSCLVTHE GSTVEKKVAP AECS         234

SEQ ID NO: 49               moltype = DNA   length = 703
FEATURE                     Location/Qualifiers
misc_feature                1..703
                            note = B10 lambda light chain full-length
source                      1..703
                            mol_type = other DNA
                            organism = synthetic construct
SEQUENCE: 49
atgtacagga tgcaactcct gtcttgcatt gcactaagtc ttgcacttgt cacgaattcg    60
caggctgtgc tgaatcagcc ggcctctgtg tctgcagccc tggggcagag ggtcaccatc   120
tcctgtaaca ccaacatcgg cagtccttat gatgtacaat ggtaccagca gctcccagga   180
aagtcccccta aaactatcat ttatggtaat agcaatcgac cctcggggtt cccgttcga   240
ttctctggct ccaagtcagg cagcacagcc accctgacca tcgctgggat ccaggctgag   300
gatgaggctg attattactg ccagtcctat gatgacaacg tcgatggtta cgtgttcggc   360
tcagggaccc aactgaccgt ccttggtcag cccaaggcct cccctcggt cacactcttc     420
ccgccctcct ctgaggagct cggcgccaac aaggccacgc tcgtgtgcct catcagcgac   480
ttctacccca gcggcgtgac ggtggcctgg aaggcagacg gcagcccat cacccagggc    540
gtggagacca ccaagccctc caagcagagc aacaacaagt acgcggccag cagctacctg   600
agcctgacgc tgacaagtg gaaatctcac agcagcttca gctgcctggt cacgcacgag    660
gggagcaccg tggagaagaa ggtggccccc gcagagtgct ctt                     703

SEQ ID NO: 50               moltype = AA   length = 223
FEATURE                     Location/Qualifiers
REGION                      1..223
                            note = Full Length Canine CTLA-4
source                      1..223
                            mol_type = protein
                            organism = synthetic construct
SEQUENCE: 50
MAGFGFRRHG AQPDLASRTW PCTALFSLLF IPVFSKGMHV AQPAVVLASS RGVASFVCEY    60
GSSGNAAEVR VTVLRQAGSQ MTEVCAATYT VEDELAFLDD STCTGTSSGN KVNLTIQGLR   120
AMDTGLYICK VELMYPPPYY VGMGNGTQIY VIDPEPCPDS DFLLWILAAV SSGLFFYSFL   180
ITAVSLSKML KKRSPLTTGV YVKMPPTEPE CEKQFQPYFI PIN                     223

SEQ ID NO: 51               moltype = AA   length = 20
FEATURE                     Location/Qualifiers
REGION                      1..20
                            note = IL2 signal sequence
source                      1..20
                            mol_type = protein
                            organism = synthetic construct
SEQUENCE: 51
MYRMQLLSCI ALSLALVTNS                                                20

SEQ ID NO: 52               moltype = AA   length = 106
FEATURE                     Location/Qualifiers
REGION                      1..106
                            note = Canine lambda-1 light chain
source                      1..106
                            mol_type = protein
                            organism = synthetic construct
SEQUENCE: 52
GQPKASPSVT LFPPSSEELG ANKATLVCLI SDFYPSGVTV AWKADGSPIT QGVETTKPSK    60
QSNNKYAASS YLSLTPDKWK SHSSFSCLVT HEGSTVEKKV APAECS                  106

SEQ ID NO: 53               moltype = AA   length = 331
FEATURE                     Location/Qualifiers
REGION                      1..331
                            note = Canine cIgG1 heavy chain
source                      1..331
                            mol_type = protein
                            organism = synthetic construct
SEQUENCE: 53
ASTTAPSVFP LAPSCGSTSG STVALACLVS GYFPEPVTVS WNSGSLTSGV HTFPSVLQSS    60
GLYSLSSMVT VPSSRWPSET FTCNVVHPAS NTKVDKPVFN ECRCTDTPPC PVPEPLGGPS   120
VLIFPPKPKD ILRITRTPEV TCVVLDLGRE DPEVQISWFV DGKEVHTAKT QSREQQFNGT   180
YRVVSVLPIE HQDWLTGKEF KCRVNHIDLP SPIERTISKA RGRAHKPSVY VLPPSPKELS   240
SSDTVSVTCL IKDFYPPDID VEWQSNGQQE PERKHRMTPP QLDEDGSYFL YSKLSVDKSR   300
WQQGDPFTCA VMHETLQNHY TDLSLSHSPG K                                  331

SEQ ID NO: 54               moltype = DNA   length = 39
FEATURE                     Location/Qualifiers
misc_feature                1..39
```

```
                        note = cCTLA-4 For
source                  1..39
                        mol_type = other DNA
                        organism = synthetic construct
SEQUENCE: 54
cacgaactcg agaccatggc tggctttgga ttccggagg                         39

SEQ ID NO: 55           moltype = DNA   length = 103
FEATURE                 Location/Qualifiers
misc_feature            1..103
                        note = cCTLA-4 Rev
source                  1..103
                        mol_type = other DNA
                        organism = synthetic construct
SEQUENCE: 55
atgcattcac tcgtgccact cgatcttctg ggcctcgaag atgtcgttca ggccgtgatg   60
gtgatggtga tggcttccgc cgcttccgcc gaagtcagaa tct                   103

SEQ ID NO: 56           moltype = DNA   length = 38
FEATURE                 Location/Qualifiers
misc_feature            1..38
                        note = cCTLA-4 For
source                  1..38
                        mol_type = other DNA
                        organism = synthetic construct
SEQUENCE: 56
acgctgaatt catggctggc tttggattcc ggaggcat                          38

SEQ ID NO: 57           moltype = DNA   length = 33
FEATURE                 Location/Qualifiers
misc_feature            1..33
                        note = cCTLA-4 Rev
source                  1..33
                        mol_type = other DNA
                        organism = synthetic construct
SEQUENCE: 57
acagtgtcga ctcaattgat gggaataaaa taa                               33

SEQ ID NO: 58           moltype = AA   length = 5
FEATURE                 Location/Qualifiers
REGION                  1..5
                        note = Linker
REPEAT                  1..5
                        note = Repeat n times, where n is an integer of at least
                         one.
source                  1..5
                        mol_type = protein
                        organism = synthetic construct
SEQUENCE: 58
GSGGS                                                               5

SEQ ID NO: 59           moltype = AA   length = 4
FEATURE                 Location/Qualifiers
REGION                  1..4
                        note = Linker
REPEAT                  1..4
                        note = Repeat n times, where n is an integer of at least
                         one.
source                  1..4
                        mol_type = protein
                        organism = synthetic construct
SEQUENCE: 59
GGGS                                                                4

SEQ ID NO: 60           moltype = AA   length = 5
FEATURE                 Location/Qualifiers
REGION                  1..5
                        note = Linker
REPEAT                  1..5
                        note = Repeat n times, where n is an integer of at least
                         one.
source                  1..5
                        mol_type = protein
                        organism = synthetic construct
SEQUENCE: 60
GGGGS                                                               5

SEQ ID NO: 61           moltype = AA   length = 4
FEATURE                 Location/Qualifiers
```

```
REGION                  1..4
                        note = Linker
source                  1..4
                        mol_type = protein
                        organism = synthetic construct
SEQUENCE: 61
GGSG                                                                    4

SEQ ID NO: 62           moltype = AA  length = 5
FEATURE                 Location/Qualifiers
REGION                  1..5
                        note = Linker
source                  1..5
                        mol_type = protein
                        organism = synthetic construct
SEQUENCE: 62
GGSGG                                                                   5

SEQ ID NO: 63           moltype = AA  length = 5
FEATURE                 Location/Qualifiers
REGION                  1..5
                        note = Linker
source                  1..5
                        mol_type = protein
                        organism = synthetic construct
SEQUENCE: 63
GSGSG                                                                   5

SEQ ID NO: 64           moltype = AA  length = 5
FEATURE                 Location/Qualifiers
REGION                  1..5
                        note = Linker
source                  1..5
                        mol_type = protein
                        organism = synthetic construct
SEQUENCE: 64
GSGGG                                                                   5

SEQ ID NO: 65           moltype = AA  length = 5
FEATURE                 Location/Qualifiers
REGION                  1..5
                        note = Linker
source                  1..5
                        mol_type = protein
                        organism = synthetic construct
SEQUENCE: 65
GGGSG                                                                   5

SEQ ID NO: 66           moltype = AA  length = 5
FEATURE                 Location/Qualifiers
REGION                  1..5
                        note = Linker
source                  1..5
                        mol_type = protein
                        organism = synthetic construct
SEQUENCE: 66
GSSSG                                                                   5

SEQ ID NO: 67           moltype = AA  length = 5
FEATURE                 Location/Qualifiers
REGION                  1..5
                        note = Linker
source                  1..5
                        mol_type = protein
                        organism = synthetic construct
SEQUENCE: 67
GGGGS                                                                   5

SEQ ID NO: 68           moltype = AA  length = 15
FEATURE                 Location/Qualifiers
REGION                  1..15
                        note = Linker
source                  1..15
                        mol_type = protein
                        organism = synthetic construct
SEQUENCE: 68
GGGGSGGGGS GGGGS                                                       15

SEQ ID NO: 69           moltype = AA  length = 19
```

```
FEATURE                 Location/Qualifiers
REGION                  1..19
                        note = Linker
source                  1..19
                        mol_type = protein
                        organism = synthetic construct
SEQUENCE: 69
GGGSSRSSSS GGGGSGGGG                                                       19

SEQ ID NO: 70           moltype = AA   length = 57
FEATURE                 Location/Qualifiers
REGION                  1..57
                        note = Linker
source                  1..57
                        mol_type = protein
                        organism = synthetic construct
SEQUENCE: 70
GGCGGTGGTT CCTCTAGATC TTCCTCCTCT GGTGGCGGTG GCTCGGGCGG TGGTGGG             57

SEQ ID NO: 71           moltype = AA   length = 335
FEATURE                 Location/Qualifiers
REGION                  1..335
                        note = Canine cIgG2 heavy chain
source                  1..335
                        mol_type = protein
                        organism = synthetic construct
SEQUENCE: 71
ASTTAPSVFP LAPSCGSTSG STVALACLVS GYFPEPVTVS WNSGSLTSGV HTFPSVLQSS           60
GLYSLSSMVT VPSSRWPSET FTCNVAHPAS KTKVDKPVPK RENGRVPRPP DCPKCPAPEM          120
LGGPSVFIFP PKPKDTLLIA RTPEVTCVVV DLDPEDPEVQ ISWFVDGKQM QTAKTQPREE          180
QFNGTYRVVS VLPIGHQDWL KGKQFTCKVN NKALPSPIER TISKARGQAH QPSVYVLPPS          240
REELSKNTVS LTCLIKDFFP PDIDVEWQSN GQQEPESKYR TTPPQLDEDG SYFLYSKLSV          300
DKSRWQRGDT FICAVMHEAL HNHYTQESLS HSPGK                                    335

SEQ ID NO: 72           moltype = AA   length = 333
FEATURE                 Location/Qualifiers
REGION                  1..333
                        note = Canine cIgG3 heavy chain
source                  1..333
                        mol_type = protein
                        organism = synthetic construct
SEQUENCE: 72
ASTTAPSVFP LAPSCGSQSG STVALACLVS GYIPEPVTVS WNSGSLTSGV HTFPSILQSS           60
GLYSLSSMVT VPSSRWPSET FTCNVAHPAT NTKVDKPVVK ECECKCNCNN CPCPGCGLLG          120
GPSVFIFPPK PKDILVTART PTVTCVVVDL DPENPEVQIS WFVDSKQVQT ANTQPREEQS          180
NGTYRVVSVL PIGHQDWLSG KQFKCKVNNK ALPSPIEEII SKTPGQAHQP NVYVLPPSRD          240
EMSKNTVTLT CLVKDFFPPE IDVEWQSNGQ QEPESKYRMT PPQLDEDGSY FLYSKLSVDK          300
SRWQRGDTFI CAVMHEALHN HYTQKSLSHS PGK                                      333

SEQ ID NO: 73           moltype = AA   length = 331
FEATURE                 Location/Qualifiers
REGION                  1..331
                        note = Canine cIgG4 heavy chain
source                  1..331
                        mol_type = protein
                        organism = synthetic construct
SEQUENCE: 73
ASTTAPSVFP LAPSCGSTSG STVALACLVS GYFPEPVTVS WNSGSLTSGV HTFPSVLQSS           60
GLYSLSSMVT VPSSRWPSET FTCNVVHPAS NTKVDKPVPK ESTCKCISPC PVPESLGGPS          120
VFIFPPKPKD ILRITRTPEI TCVVLDLGRE DPEVQISWFV DGKEVHTAKT QPREQQFNST          180
YRVVSVLPIE HQDWLTGKEF KCRVNHIGLP SPIERTISKA RGQAHQPSVY VLPPSPKELS          240
SSDTVTLTCL IKDFFPPEID VEWQSNGQPE PESKYHTTAP QLDEDGSYFL YSKLSVDKSR          300
WQQGDPFTCA VMHEALQNHY TDLSLSHSPG K                                        331

SEQ ID NO: 74           moltype = AA   length = 114
FEATURE                 Location/Qualifiers
REGION                  1..114
                        note = A1 VH PRT
source                  1..114
                        mol_type = protein
                        organism = synthetic construct
SEQUENCE: 74
EVQLVESGGD LVKPAGSLRL SCVASGFSFS SYAMNWVRQA PGKGLQWIAG INSGGSSTSH           60
IDAIKGRFTI SRDNAKNTLY LQMNSLRAED TAVYYCAISN WAYWGQGTLV TVSS                114

SEQ ID NO: 75           moltype = DNA  length = 342
FEATURE                 Location/Qualifiers
misc_feature            1..342
                        note = A1 VH DNA
```

```
source                  1..342
                        mol_type = other DNA
                        organism = synthetic construct
SEQUENCE: 75
gaggtgcagc tggtggagtc tgggggagac ctggtgaagc ctgcaggtc cctgagattg    60
tcctgtgtgg cctctggatt ctccttcagc agttatgcca tgaactgggt ccgccaggct  120
cctgggaagg ggctgcagtg gatcgcaggt attaatagcg gtggaagtag tacaagtcat  180
atagacgcta taaagggccg cttcaccatc tccagagaca cgccaagaa cacactgtat   240
ttacagatga atagcctgag agccgaggac acggccgtgt attactgtgc gattagtaat  300
tgggcctact ggggccaggg aaccctggtc accgtctcct ca                      342

SEQ ID NO: 76           moltype = AA  length = 276
FEATURE                 Location/Qualifiers
REGION                  1..276
                        note = A1 scFv PRT
source                  1..276
                        mol_type = protein
                        organism = synthetic construct
SEQUENCE: 76
QAVLNQPASV SGSLGQRVTI SCTGSSSDIG KSYVAWYQQL PGTGPRTLIN VDGNRASGVP    60
DRFSVSRSGN TATLTISGLQ AEDEADYHCS SWDWSLHTYV FGSGTQLTIL GGGSSRSSSS   120
GGGGSGGGGE VQLVESGGDL VKPAGSLRLS CVASGFSFSS YAMNWVRQAP GKGLQWIAGI   180
NSGGSSTSHI DAIKGRFTIS RDNAKNTLYL QMNSLRAEDT AVYYCAISNW AYWGQGTLVT   240
VSSESPSPPN LTSGQAGQHH HHHHGAYPYD VPDYAS                             276

SEQ ID NO: 77           moltype = DNA  length = 994
FEATURE                 Location/Qualifiers
misc_feature            1..994
                        note = A1 scFv DNA
source                  1..994
                        mol_type = other DNA
                        organism = synthetic construct
SEQUENCE: 77
caggctgtgc tgaatcagcc ggcctcagtg tccgggtccc tgggccagag ggtcaccatc    60
tcctgcactg gaagcagctc cgacatcggt aaaagttatg tggcctggta ccagcagctc   120
ccgggaacag gccccagaac cctcatcaat gttgatggta accgagcctc aggggtcccc   180
gatcgattct ctgtctccag gtcaggcaac acagccaccc tgaccatctc cgggctccag   240
gctgaggatg aggctgatta tcactgctca tcctgggact ggagtctcca tacttacgtg   300
ttcggctcag ggacccagct gaccatcctc ggtggtggtt cctctagatc ttcctcctct   360
ggtggcggtg gctcgggcgg tggtggggag gtgcagctgg tggagtctgg gggagacctg   420
gtgaagcctg cagggtccct gagattgtcc tgtgtggcct ctggattctc cttcagcagt   480
tatgccatga ctgggtccg ccaggctcct gggaagggc tgcagtggat cgcaggtatt   540
aatagcggtg gaagtagtac aagtcatata gacgctataa agggccgctt caccatctcc   600
agagacaacg ccaagaacac actgtattta cagatgaata gcctgagagc cgaggacacg   660
gccgtgtatt actgtgcgat tagtaattgg gcctactggg gccagggaac cctggtcacc   720
gtctcctcag agagtccatc ccctcccaac ctcactagtg gccaggccgg ccagcaccat   780
caccatcacc atggcgcata cccgtacgac gttccgact acgcttctta ggagggtggt   840
ggctctgagg gtggcggttc tgagggtggc ggctctgagg gaggcggttc cggtggtggc   900
tctggttccg gtgatttga ttatgaaaag atggcaaacg ctaataaggg gctatgaccg   960
aaaatgccga tgaaacgtg ctacagtctg acgc                                994
```

CANINE MONOCLONAL ANTIBODIES AGAINST CANINE CYTOTOXIC T LYMPHOCYTE ASSOCIATED PROTEIN 4 (CTLA-4)

CROSS-REFERENCE TO RELATED APPLICATION

The present application is a continuation of International Patent Application No. PCT/US22/25614, filed on Apr. 20, 2022, which is entitled to priority under 35 U.S.C. § 119(e) to U.S. Provisional Patent Application No. 63/177,692, filed on Apr. 21, 2021, all of which are hereby incorporated by reference in their entireties.

STATEMENT REGARDING FEDERALLY SPONSORED RESEARCH OR DEVELOPMENT

This invention was made with government support under HHSN261201800042C awarded by the National Institutes of Health. The government has certain rights in the invention.

REFERENCE TO SEQUENCE LISTING

The Sequence Listing concurrently submitted herewith as an XML file named "046483-7312US1 Sequence Listing ST26.xml", created on Oct. 20, 2023 and having a size of 122,880 bytes is herein incorporated by reference in its entirety.

BACKGROUND OF THE INVENTION

Advances in understanding the interplay between the immune system and cancer have led to the successful development of immunotherapies against tumors in human patients. These new immune-based treatments have had considerable success in the clinic and are increasingly becoming frontline therapies. Indeed, human cancer immunotherapy is now recognized as one of the pillars of treatment alongside surgery, radiation, and chemotherapy. The field of veterinary cancer immunotherapy has also rapidly advanced in the last decade, though the availability of animal-specific therapies and a complete understanding of their particular effects remains an on-going challenge.

Checkpoint inhibition therapy is a promising immunotherapy strategy that works by inhibiting receptors that negatively regulate T cells. In effect, these therapies remove natural "brakes", called immune checkpoints, that restrain T cell function. While these negative receptors normally play a key role in preventing immune responses from becoming toxic, many cancers take advantage of this negative signaling to blunt T-cell based immune responses directed against them. One of the key immune checkpoint receptors that regulates T cells is Cytotoxic T Lymphocyte Protein 4 or CTLA-4. Normally expressed on activated T cells, CTLA-4 delivers a negative signal to the T cell upon binding its ligands B7-1(CD80) and B7-2 (CD86), which are normally expressed on antigen-presenting cells. In this way, CTLA-4 functions much like a governor on an engine, preventing over activation of the immune system. Antibodies blocking CTLA-4, such as ipilimumab, were the first checkpoint inhibitor therapies to gain FDA approval for use in human patients and has proved useful in the treatment of immunogenic cancers such as melanoma.

Thus, there is a need in the art for the development of canine antibodies that can be used to treat veterinary cancers in canine subjects through the blockade of CTLA-4 on tumor-specific T cells. The present invention addresses and satisfies this need.

SUMMARY OF THE INVENTION

As described herein, the present invention relates to canine antibodies, binding polypeptides, and scFvs specific for canine cytotoxic T lymphocyte associated protein 4 (CTLA-4). Also included are methods and compositions for treating diseases, especially cancer, in canine patients comprising the anti-CTLA-4 antibodies, binding polypeptides, and scFvs of the invention.

In one aspect, the invention provides a an antibody or antigen-binding fragment thereof comprising an antigen-binding domain that specifically binds to an epitope of canine cytotoxic T lymphocyte-associated protein 4 (CTLA-4), wherein the antigen-binding domain comprises:
  i. a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NOs: 6, 25, 40, or 74; and
  ii. a light chain variable region comprising an amino acid sequence having at least 80%, 85%, 90%, 95%, 96%, 97%, 98%, 99% identity to the amino acid sequence set forth in SEQ ID NOs: 8, 27, or 42;
  wherein the heavy chain variable region comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  wherein the light chain variable region comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

In certain embodiment, the antibody or antigen-binding fragment thereof is selected from the group consisting of a full-length antibody, a Fab, and a single-chain variable fragment (scFv).

In certain embodiments, the antibody or antigen-binding fragment thereof is a full-length antibody.

In certain embodiments, the antibody is a canine antibody.

In certain embodiments, the antibody or antigen-binding fragment thereof of any one of claim 1, wherein the antigen binding domain comprises a heavy chain variable region comprising an amino acid sequence set forth in SEQ ID NOs: 6, 25, 40, or 74.

In certain embodiments, the antigen binding domain consists of a heavy chain variable region consisting of an amino acid sequence set forth in SEQ ID NOs: 6, 25, 40, or 74.

In certain embodiments, the antibody or antigen-binding fragment thereof of any one of claims 1-4, wherein the antigen binding domain comprises a light chain variable region comprising an amino acid sequence set forth in SEQ ID NO: 8, 27, or 42.

In certain embodiments, the antibody or antigen-binding fragment thereof of any one of claims 1-4, wherein the antigen binding domain consists of a light chain variable region comprising an amino acid sequence set forth in SEQ ID NO: 8, 27, or 42.

In another aspect, the invention includes an isolated antibody or antigen-binding fragment thereof comprising:
  i. a heavy chain variable region comprising the amino acid sequence set forth in SEQ ID NO: 6; and
  ii. a light chain variable region comprising the amino acid sequence set forth in SEQ ID NO: 8.

In another aspect, the invention includes a single-chain variable fragment (scFv) comprising an antigen-binding domain that specifically binds to an epitope of canine cytotoxic T lymphocyte associated protein 4 (CTLA-4) comprising:
  i. a heavy chain variable region that comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  ii. a light chain variable region that comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39),
  wherein the heavy chain variable region and the light chain variable region are separated by a linker.

In another aspect, the invention includes a single-chain variable fragment (scFv) comprising:
  i. a heavy chain variable region comprising the amino acid sequence set forth in SEQ ID NOs: 6, 25, 40, or 74; and
  ii. a light chain variable region comprising the amino acid sequence set forth in SEQ ID NO: 8, 27, or 42,
  wherein the heavy chain variable region and the light chain variable region are separated by a linker.

In another aspect, the invention includes a single chain variable fragment (scFv) comprising an amino acid sequence set forth in SEQ ID NOs: 29, 44, or 76.

In another aspect, the invention includes a single chain variable fragment (scFv) consisting of an amino acid sequence set forth in SEQ ID NOs: 29, 44, or 76.

In another aspect, the invention includes a full-length antibody comprising an antigen-binding domain that specifically binds to an epitope of canine cytotoxic T lymphocyte associated protein 4 (CTLA-4), wherein the antigen-binding domain comprises:
  i. a heavy chain variable region that comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  ii. a light chain variable region that comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

In another aspect, the invention includes a full-length antibody comprising:
  i. a heavy chain variable region comprising the amino acid sequence set forth in SEQ ID NOs: 6, 25, 40, or 74; and
  ii. a light chain variable region comprising the amino acid sequence set forth in SEQ ID NO: 8, 27, or 42.

In another aspect, the invention includes a full-length antibody comprising a heavy chain amino acid sequence set forth in SEQ ID NOs: 10, 12, 14, 16, 31, 46, 71, 72, or 73 and a light chain amino acid sequence set forth in SEQ ID NOs: 18, 33, or 48.

In another aspect, the invention includes a full-length antibody consisting of a heavy chain amino acid sequence set forth in SEQ ID NOs: 10, 12, 14, 16, 31, 46, 71, 72, or 73 and a light chain amino acid sequence set forth in SEQ ID NOs: 18, 33, or 48.

In another aspect, the invention includes an isolated nucleic acid encoding the scFv or full-length antibody of any preceding claim.

In another aspect, the invention includes an isolated nucleic acid encoding an antibody or antigen-binding fragment thereof comprising an antigen-binding domain that specifically binds an epitope of canine cytotoxic T lymphocyte associated protein 4 (CTLA-4), wherein the antigen-binding domain comprises:
  i. a heavy chain variable region encoded by a nucleic acid comprising a polynucleotide sequence having at least 80%, 85%, 90%, 95%, 96%, 96%, 97%, 98%, 99% identity to SEQ ID NOs: 7, 26, 41, or 75; and
  ii. a light chain variable region encoded by a nucleic acid comprising a polynucleotide sequence having at least 80%, 85%, 90%, 95%, 96%, 96%, 97%, 98%, 99% identity to the amino acid sequence of the light chain variable region set forth in SEQ ID NOs: 9, 28, or 43;
  wherein, the heavy chain variable region comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  wherein, the light chain variable region comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

In certain embodiments, the antibody or antigen-binding fragment thereof is selected from the group consisting of a full-length antibody, a Fab, and a single-chain variable fragment (scFv).

In certain embodiments, the antibody is a full-length antibody.

In certain embodiments, the antibody is a canine antibody.

In certain embodiments, the heavy chain variable region is encoded by a nucleic acid comprising the polynucleotide sequence set forth in SEQ ID NO: 7, 26, 41, or 75.

In certain embodiments, the heavy chain variable region is encoded by a nucleic acid consisting of the polynucleotide sequence set forth in SEQ ID NO: 7, 26, 41, or 75.

In certain embodiments, the light chain variable region is encoded by a nucleic acid comprising the polynucleotide sequence set forth in SEQ ID NOs: 9, 28, or 43.

In certain embodiments, the light chain variable region is encoded by a nucleic acid consisting of a polynucleotide sequence set forth in SEQ ID NOs: 9, 28, or 43.

In another aspect, the invention includes an isolated nucleic acid encoding an antibody or antigen binding fragment thereof comprising:
  i. a heavy chain variable region encoded by a nucleic acid sequence comprising the polynucleotide sequence set forth in SEQ ID NOs: 7, 26, 41, or 75; and
  ii. a light chain variable region encoded by a nucleic acid sequence comprising the polynucleotide sequence set forth in SEQ ID NOs: 9, 28, or 43.

In another aspect, the invention includes an isolated nucleic acid encoding a single-chain variable fragment (scFv) comprising:
  i. a heavy chain variable region that comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  ii. a light chain variable region that comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

In another aspect, the invention includes an isolated nucleic acid encoding a single-chain variable fragment (scFv) comprising:
  i. a heavy chain variable region comprising a nucleotide sequence set forth in SEQ ID NOs: 7, 26, 41, or 75; and
  ii. a light chain variable region comprising a nucleotide sequence set forth in SEQ ID NOs: 9, 28, or 43,
  wherein the heavy chain variable region and the light chain variable region are separated by a linker.

In another aspect, the invention includes an isolated nucleic acid encoding a single-chain variable fragment (scFv) comprising a polynucleotide sequence set forth in SEQ ID NOs: 30, 45, or 77.

In another aspect, the invention includes an isolated nucleic acid encoding a single-chain variable fragment (scFv) consisting of a polynucleotide sequence set forth in SEQ ID NOs: 30, 45, or 77.

In another aspect, the invention includes a vector comprising the isolated nucleic acid of any one of claims 19-32.

In certain embodiments, the vector is an expression vector.

In certain embodiments, the vector is selected from the group consisting of a DNA vector, an RNA vector, a plasmid, a lentiviral vector, an adenoviral vector, an adeno-associated viral vector, and a retroviral vector.

In another aspect, the invention includes a host cell comprising the vector of any one of above aspects or any aspect or embodiment disclosed herein.

In certain embodiments, the host cell is of eukaryotic or prokaryotic origin.

In certain embodiments, the host cell is of mammalian origin.

In certain embodiments, the host cell is of bacterial origin.

In another aspect, the invention includes a method of producing an antibody or antigen-binding fragment thereof that binds to canine cytotoxic T lymphocyte associated protein 4 (CTLA-4), the method comprising culturing the host cell of any one of the above aspects or any aspect or embodiment disclosed herein.

In another aspect, the invention includes a pharmaceutical composition comprising the full-length antibody or scFv of any one of the above aspects or any aspect or embodiment disclosed herein and a pharmaceutically acceptable carrier.

In another aspect, the invention includes a method for treating a cancer in a subject in need thereof, comprising administering to the subject the antibody or antigen-binding fragment thereof of any one of the above aspects or any aspect or embodiment disclosed herein.

In certain embodiments, the cancer is associated with cytotoxic T lymphocyte associated protein 4 (CTLA-4).

In certain embodiments, the CTLA-4 is expressed on a cancer-associated cell.

In certain embodiments, the cancer-associated cell is a T lymphocyte.

In certain embodiments, the antibody or antigen-binding fragment thereof specifically binds to canine CTLA-4.

In certain embodiments, the antibody or antigen-binding fragment thereof is selected from the group consisting of a full-length antibody, a Fab, and a single-chain variable fragment (scFv).

In certain embodiments, the antibody or antigen-binding fragment thereof is a full-length antibody.

In certain embodiments, the antibody is a caninized antibody.

In certain embodiments, the subject is canine.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1. is a table displaying phage input and output results from library panning against canine CTLA-4 (cCTLA-4). A comprehensive canine IgM/IgG/λ/κ scFv phage display library containing an estimated 40 billion canine scFv transformants underwent four rounds of solid phase selection ("panning") against biotinylated AviTag™-cCTLA-4. Numbers of phage in the input and output (eluate) are reported together with % phage bound to target and enrichment of antigen-specific binders following each panning round.

Figure 3:
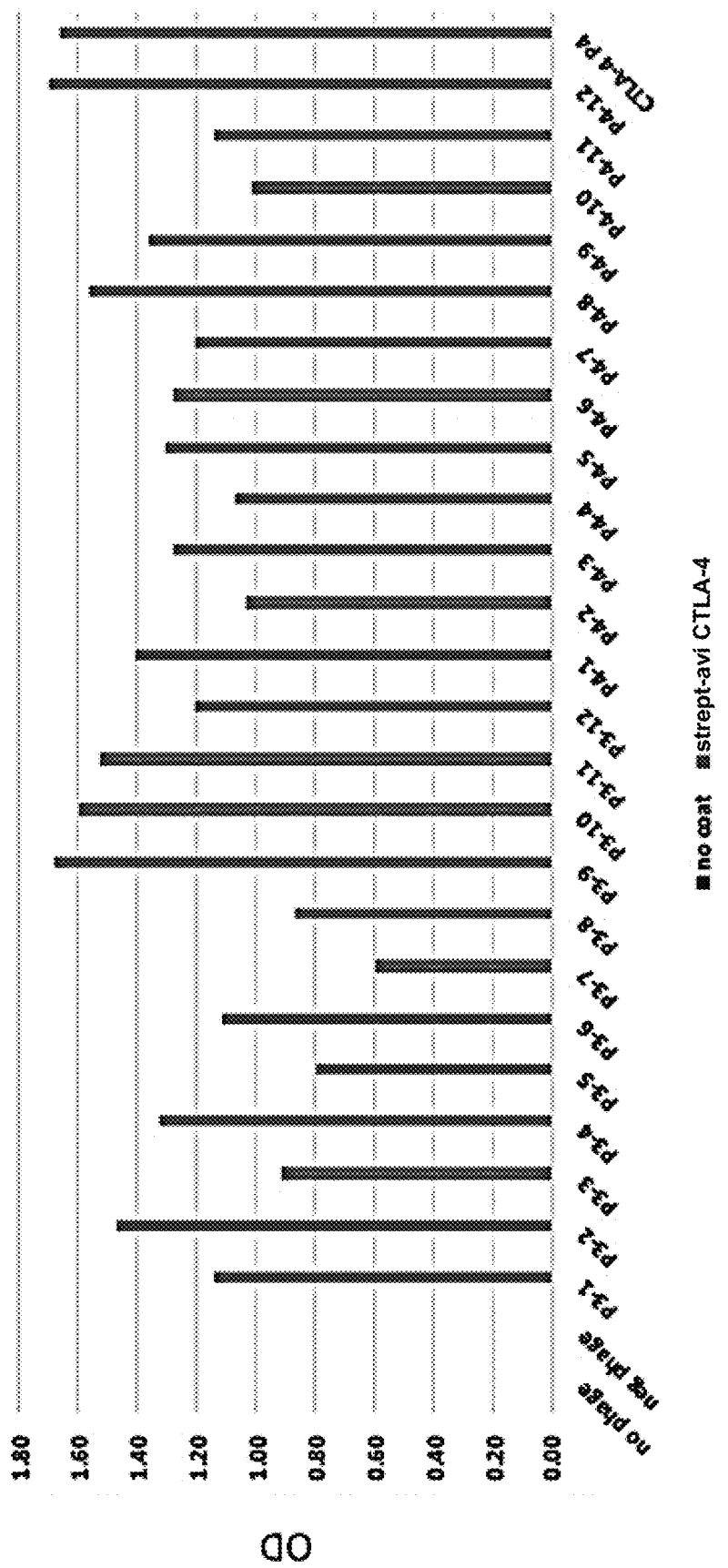

FIG. 3 illustrates screening of canine scFv antibodies from panning rounds 3 and 4 for binding to recombinant canine CLTA-4. Twelve clones from panning round 3 and 12 clones from panning round 4 against canine CTLA-4 were randomly selected and tested for their ability to bind to cCTLA-4 by scFv phage ELISA. All 24 clones bound to cCTLA-4. Nucleotide sequencing of these 24 scFv revealed 20 unique antibodies, the majority (17) of which contained a lambda light chain. No phage and an irrelevant MERS (Middle East Respiratory Syndrome virus) specific phage were used as negative controls. Polyclonal phage from the fourth round of panning against canine CTLA-4 was used as the positive control.

Figure 4:
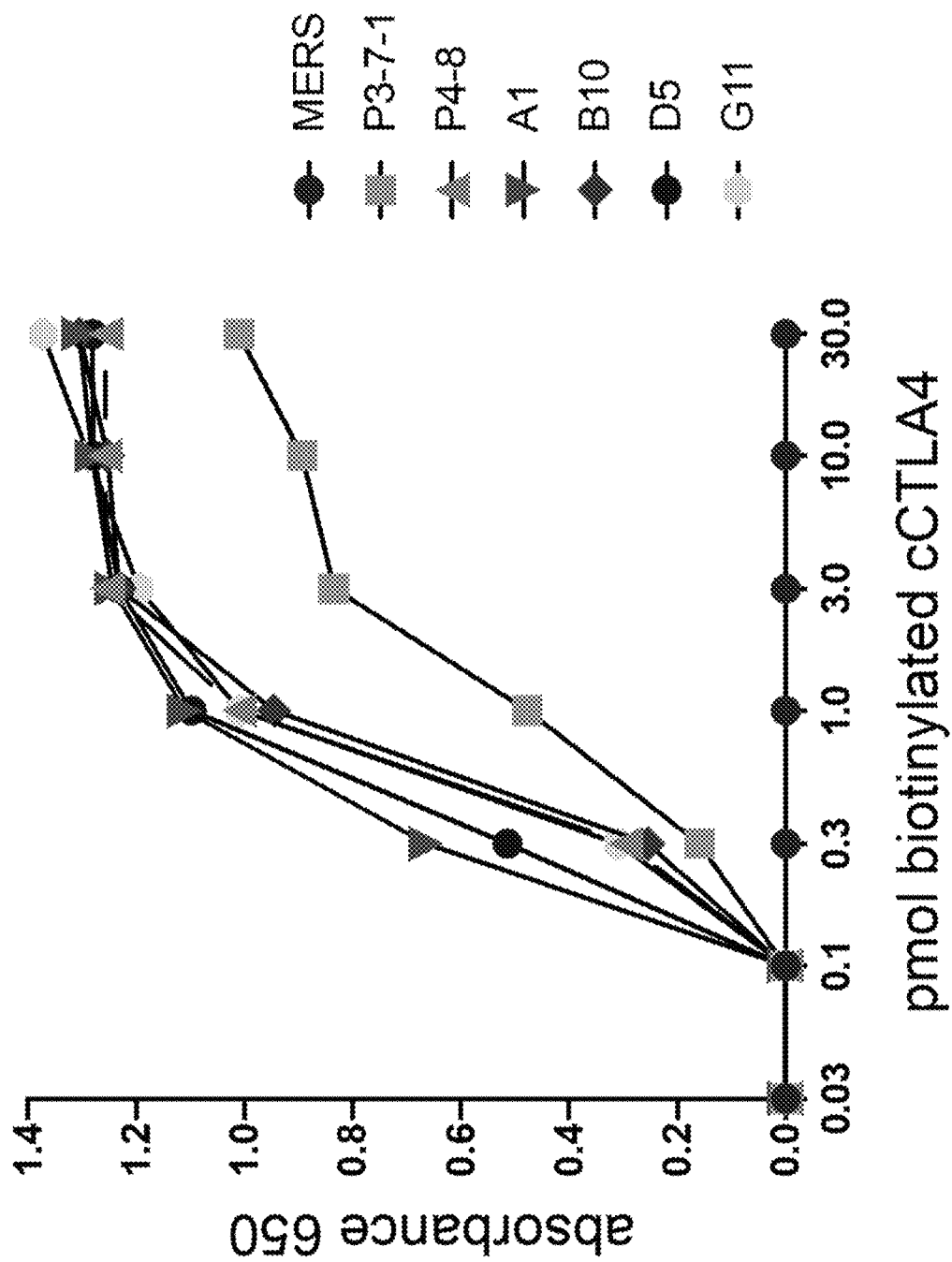

FIG. 4. Illustrates the binding of clone P4-8 and additional soluble CTLA-4 scFv (identified via high throughput screening (HTS) expression assays) to cCTLA-4 using ELISA. Unique scFv clones that bind cCTLA-4 in additional to clone P4-8 (FIG. 3) were identified via an HTS assay (A1, B10, D5 and G11). Unique, soluble, HA tagged and purified scFv were tested for their ability to bind to increasing concentrations of cCTLA-4 by ELISA. 0.25 ug/ml of soluble scFvs were added to each well and bound scFvs were detected using an AP-conjugated anti-HA antibody. All clones bound to cCTLA-4 with a range of affinities. A soluble single chain directed against the irrelevant MERS protein was used as a negative control.

Figures 5A, 5B:
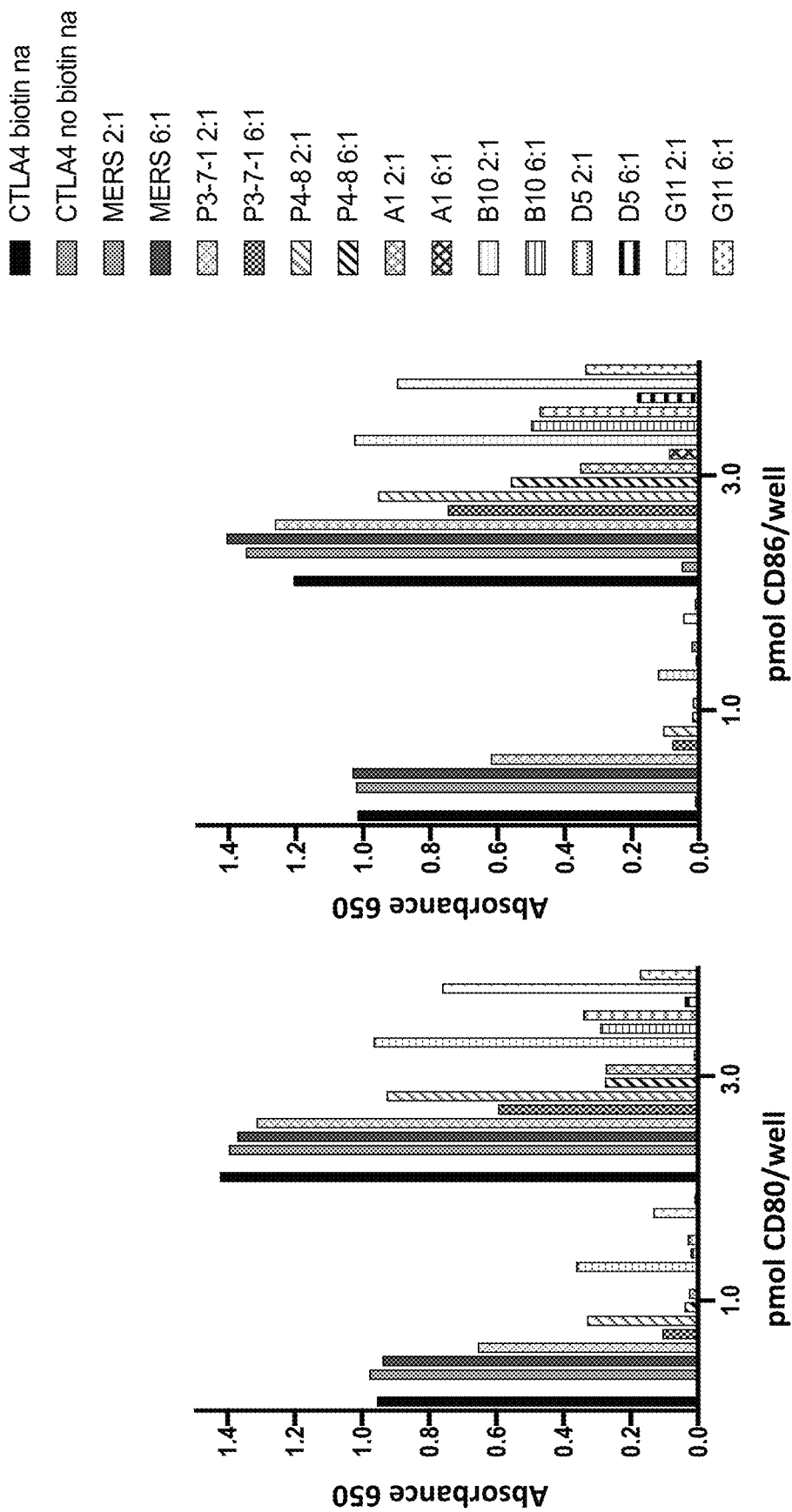

FIGS. 5A-5B illustrates CTLA-4 specific soluble scFv inhibit the binding of cCTLA-4 to its cognate ligands CD80 and CD86. 1.0 and 3.0 pmol of recombinant human CD86-Fc chimera (FIG. 5A) or human CD80-Fc chimera (FIG. 5B) were bound to ELISA plates overnight. Wells were blocked with 5% milk/PBS 0.05% Tween® 20. Biotinylated cCTLA-4 extracellular domain (ECD) was pre-incubated with each soluble scFv at the indicated molar ratios for 1 hr at RT prior to being added to the plate and incubated for 2 hr. After washing, a streptavidin-AP conjugate and subsequent AP colorimetric substrate were used to detect cCTLA-4 bound to CD80 or CD86. Biotinylated and unbiotinylated cCTLA-4 in the absence of any antibody were used as positive and negative controls. "na"=no antibody.

FIG. 6 is a table illustrating the expression levels of anti-canine-IgG.

Figure 7:
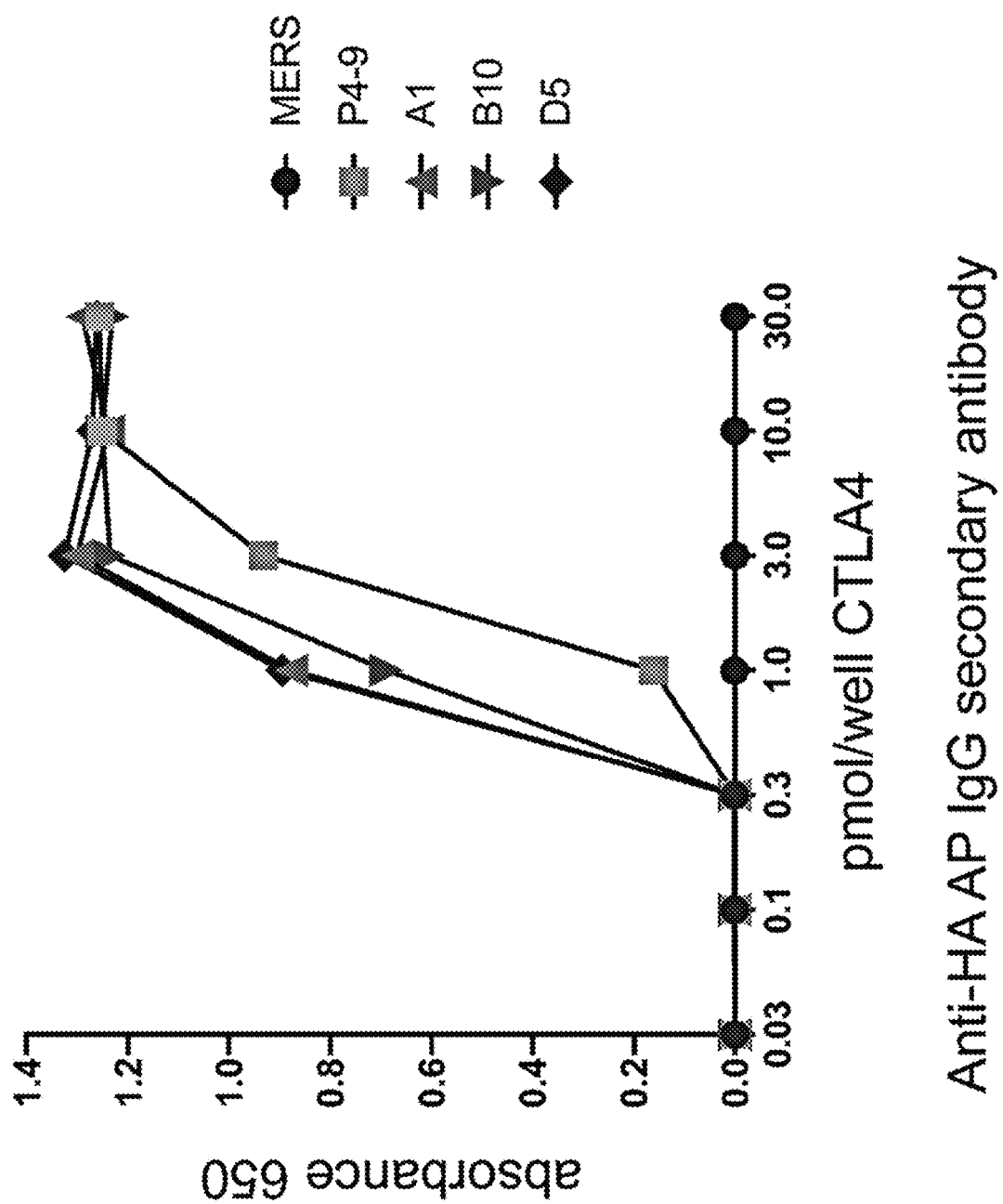

FIG. 7 illustrates an ELISA analysis of full-length canine anti-canine CTLA-4 mAbs.

Figures 8A, 8B:
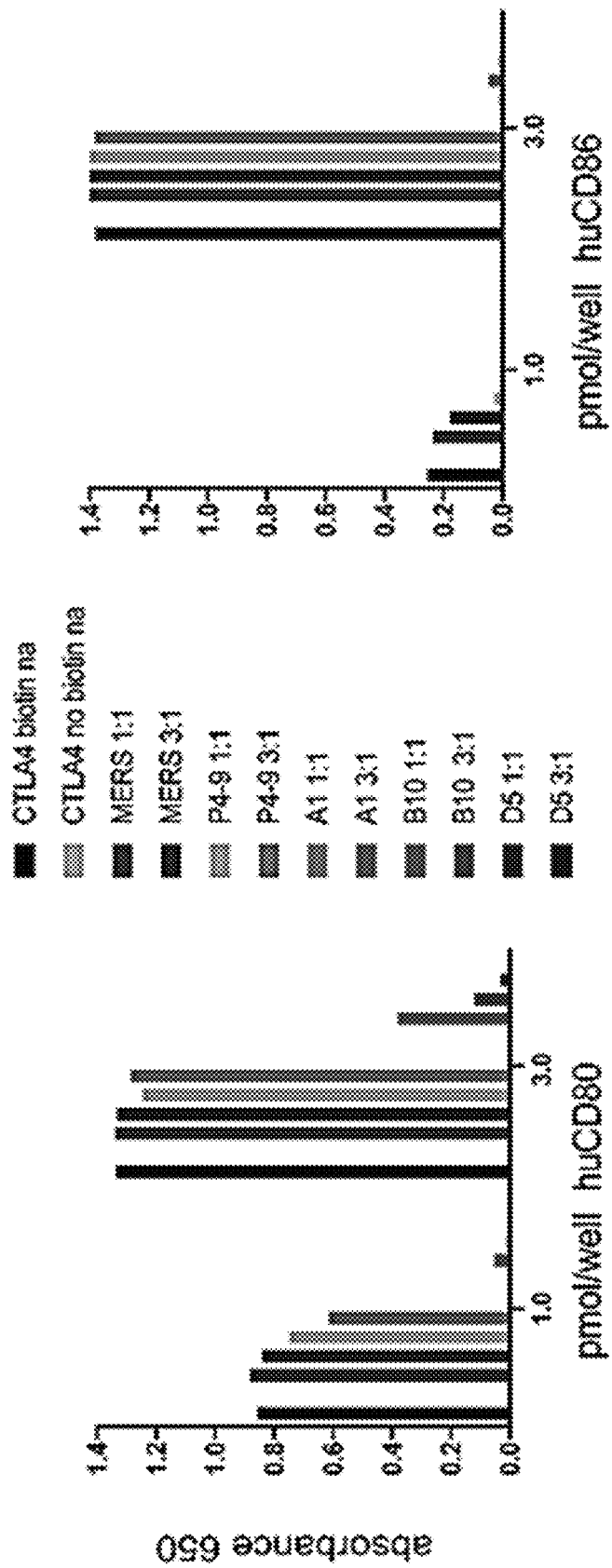

FIGS. 8A-8B illustrate an assay of the inhibition of CTLA-4 binding to its cognate ligands, CD80 (FIG. 8A) and CD86 (FIG. 8B), as purified full-length monoclonal canine IgGs.

FIG. 9 is a table illustrating that substitution of A1 VH framework regions with B10 VH framework regions rescues production of anti-canine CTLA-4 Clone A1 (the modified clone is labeled mut2).

Figure 10:
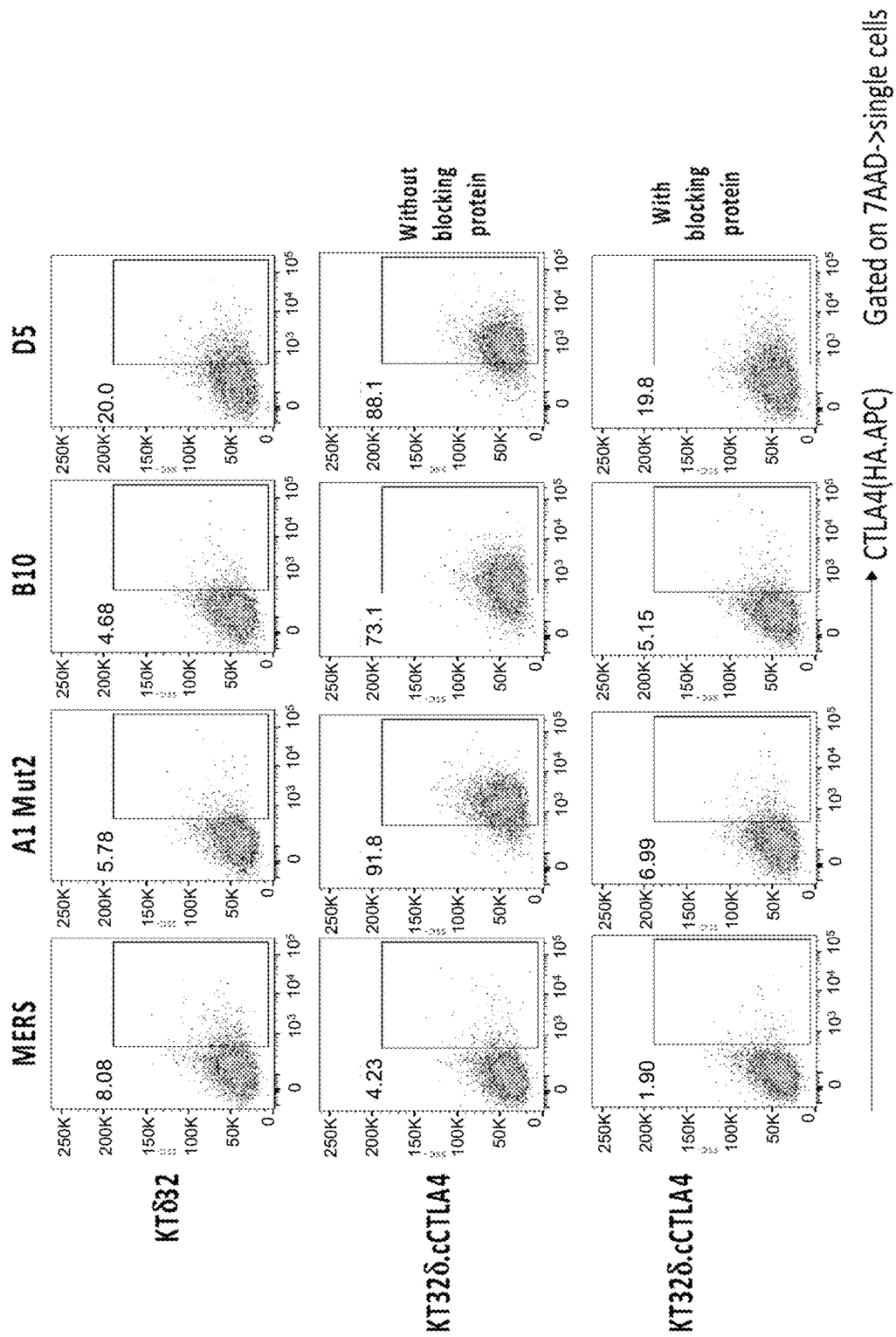

FIG. 10 illustrates the evaluation of anti-CTLA-4 mAb clones binding to membrane-expressed canine CTLA-4. K562 cells lacking the FcγRII (CD32) were genetically engineered to express canine CTLA-4 (KT32δ.cCTLA4). KT32δ cells (top row) and KT32δ.cCTLA4 cells (middle row) were incubated with three anti-CTLA-4 clones reformatted as canine isotype IgG1 and surface labeling was detected using an anti-HA antibody. To confirm antigen-specific binding, anti-CTLA-4 clones were first incubated with soluble cCTLA-4 protein to block antigen binding sites and then used for cell surface labeling (bottom row).

Figure 11A:
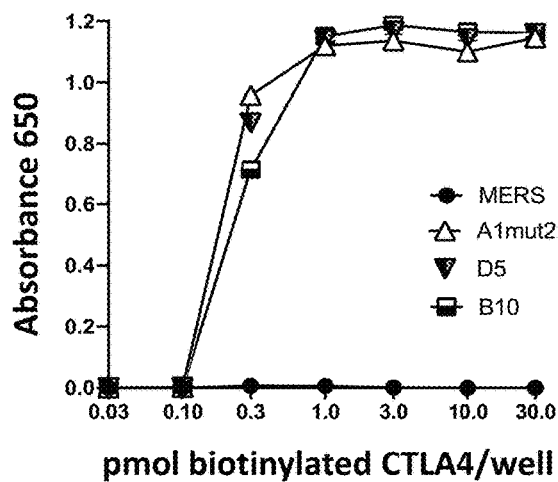
Figure 11B:
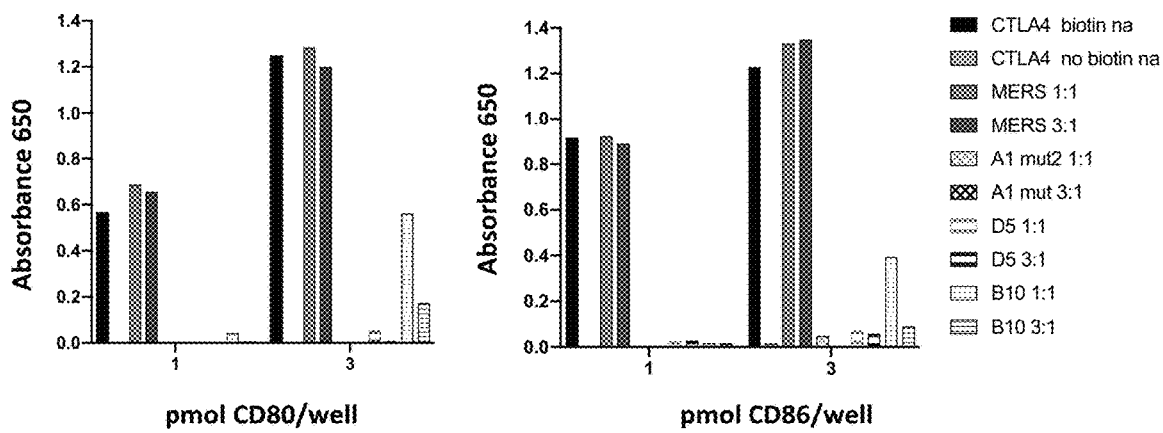
Figure 11C:
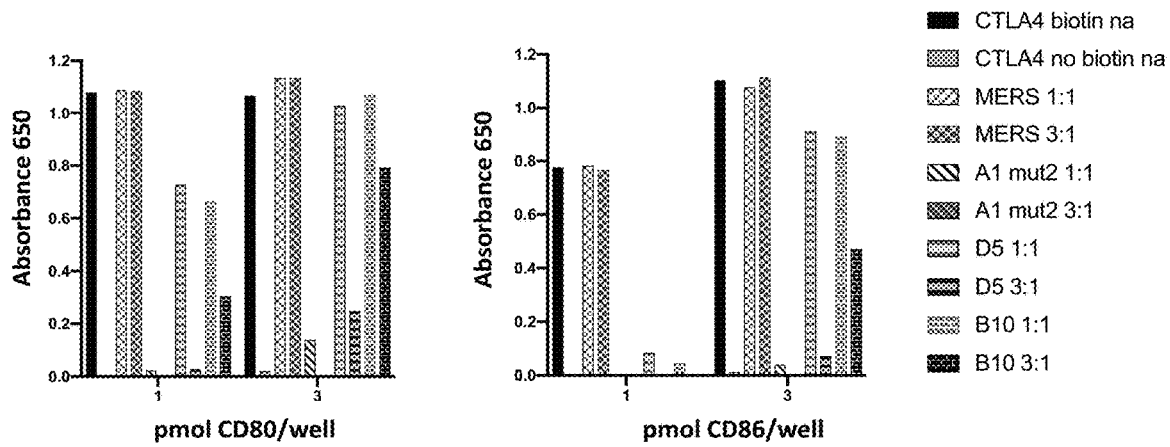

FIGS. 11A-11C illustrate that scFv clones reformatted as fully canine IgG molecules retain their ability to bind cCTLA-4 and inhibit its interaction with recombinant human and canine CD80 and CD86. Full length, bivalent IgG antibodies were generated from isolated scFvs by cloning the VH and VL chains of selected scFvs into separate heavy and light chain expression plasmids. Adherent 293T cells were transiently co-transfected with light and heavy chain plasmids and mAbs were purified from plate supernatants 3 days later using protein A affinity chromatography. FIG. 11A. mAbs were evaluated for binding to increasing concentrations of cCTLA-4 by ELISA. FIG. 11B. mAbs were evaluated for their ability to inhibit the interaction of cCTLA-4 with recombinant human CD80 (left graph) and rhuCD86 (right graph) at the molar ratios shown. Similarly, FIG. 11C shows inhibition of interaction of cCTLA-4 with recombinant canine CD80 (left graph) and CD86 (right graph) at the molar ratios shown.

Figure 12A:
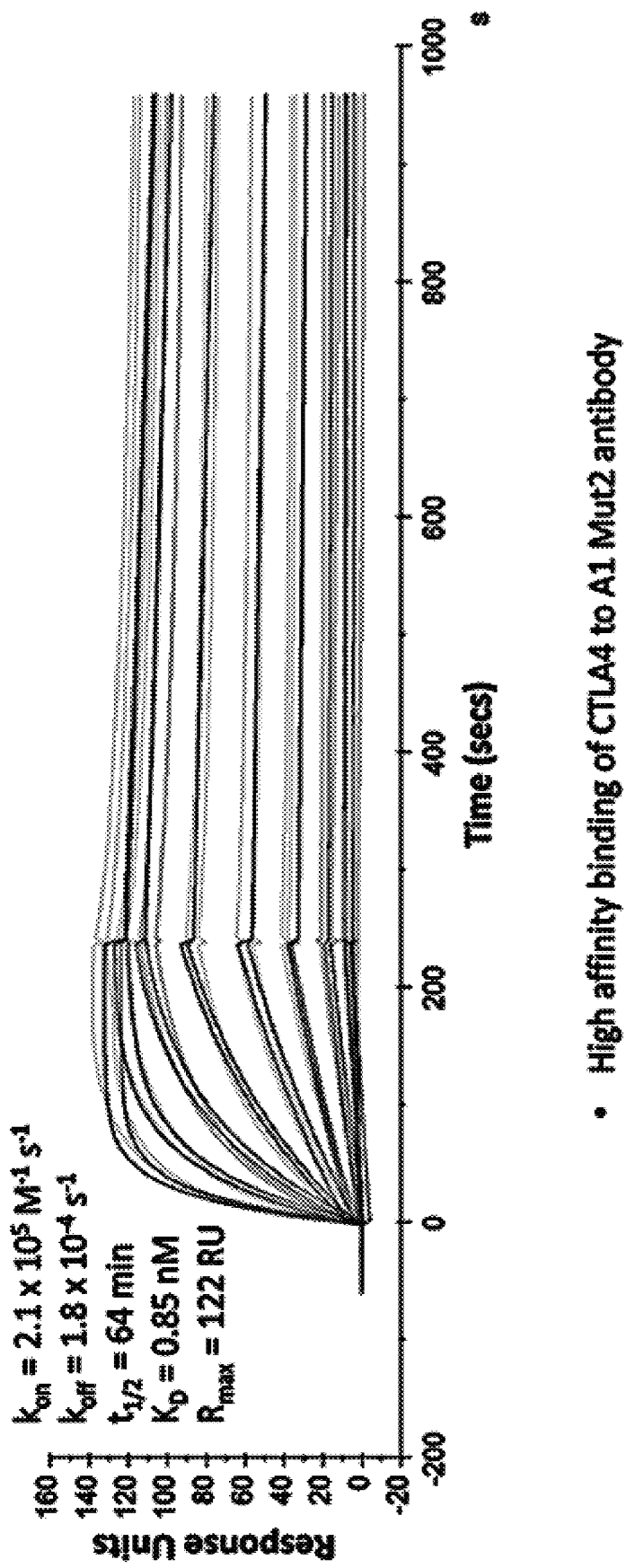
Figure 12B:
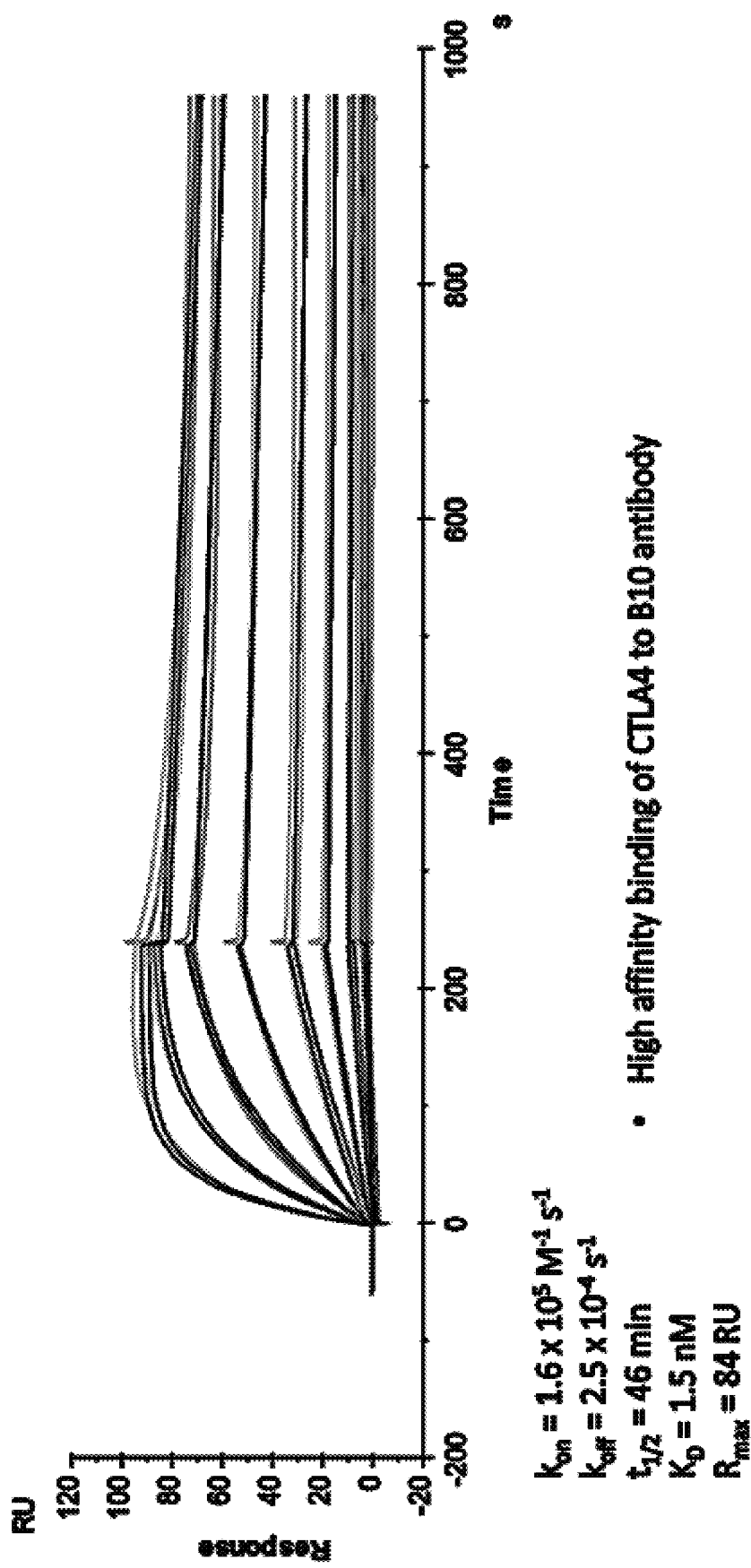
Figure 12C:
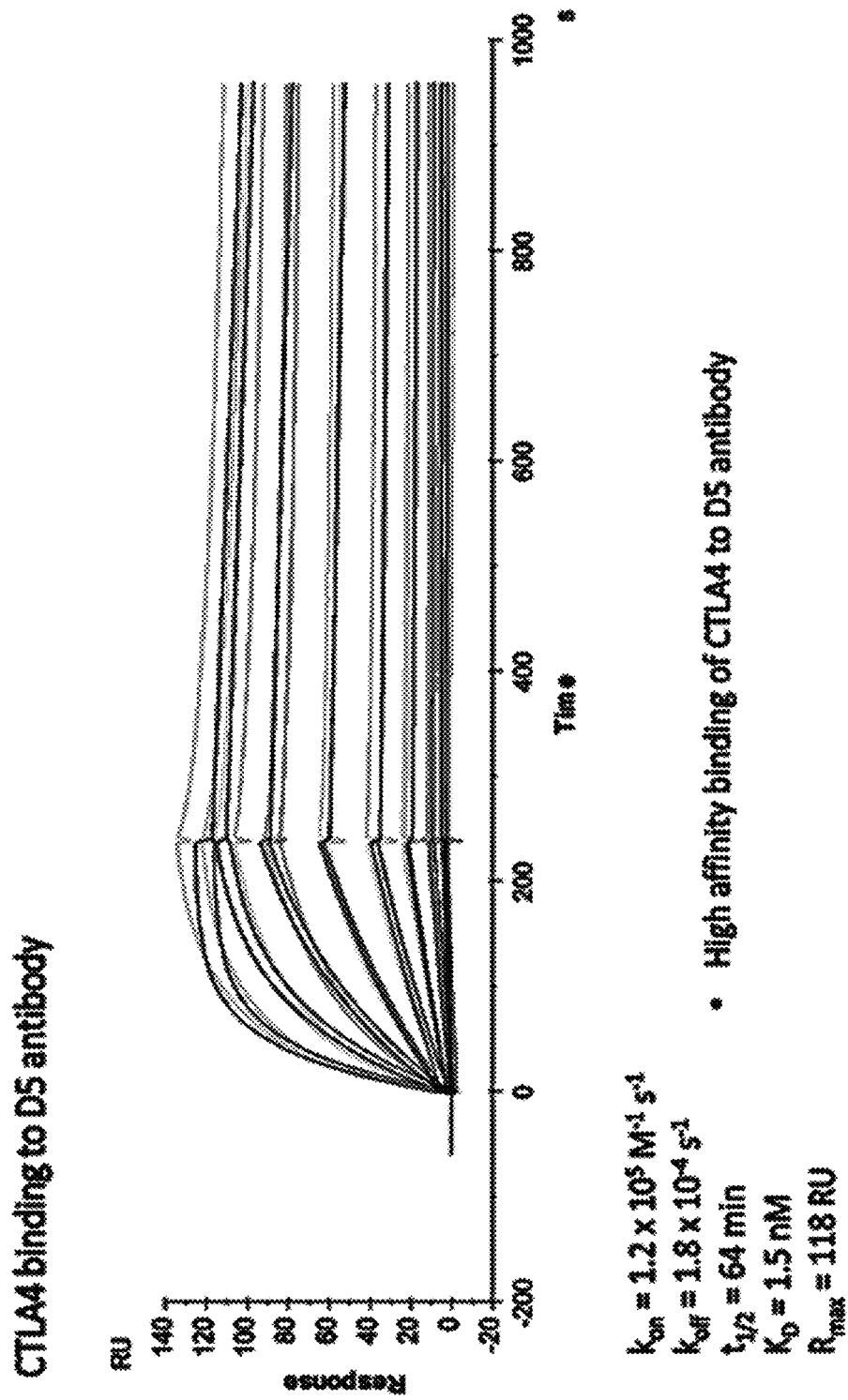

FIGS. 12A-12C illustrate that CTLA-4 specific clones exhibit high binding affinity for canine CTLA-4. FIG. 12A shows CTLA-4 binding to A1mut2 antibody. FIG. 12B shows CTLA-4 binding to B10 antibody. FIG. 12C shows CTLA-4 binding to D5 antibody.

Figure 13:
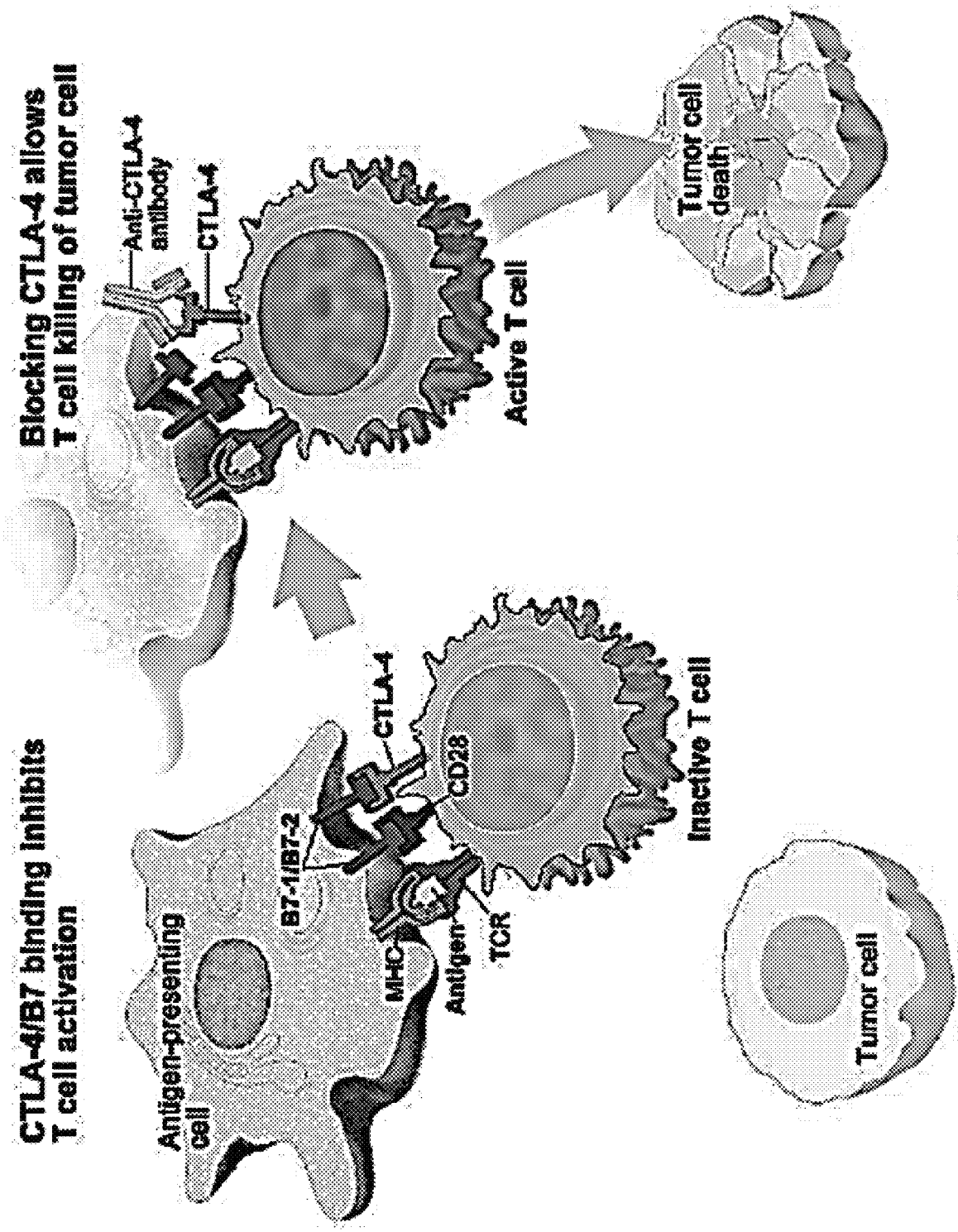

FIG. 13 is a diagram illustrating the normal function of CTLA-4 upon binding its cognate ligands on antigen presenting cells and the strategy of antibody-based blockade of CTLA-4 signaling.

Figure 14:
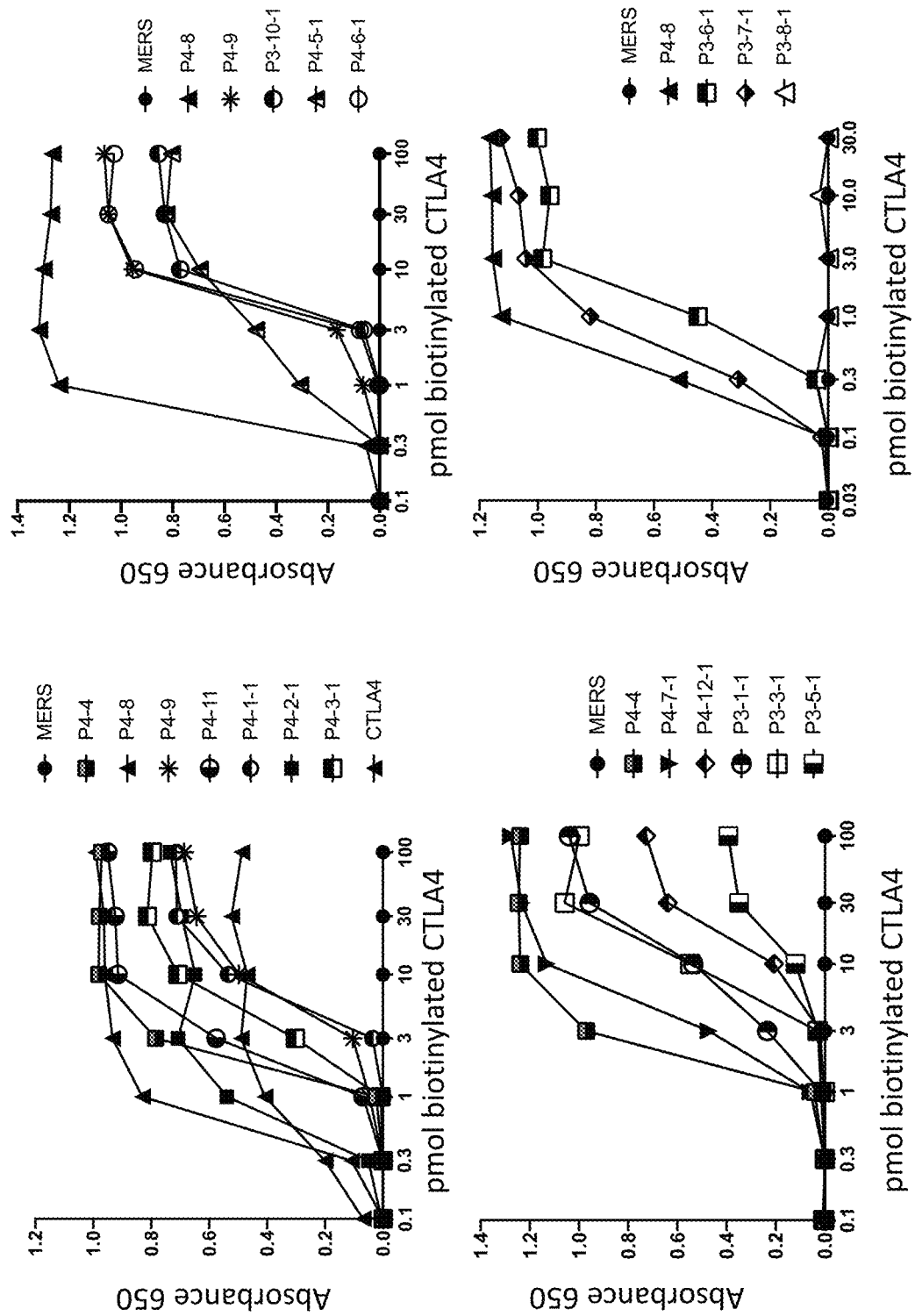

FIG. 14 illustrates the binding of unique soluble CTLA-4 scFv to canine CTLA-4 by ELISA. Unique, soluble, HA-tagged and purified scFvs from panning rounds 3 (P3) and 4 (P4) were tested for their ability to bind to increasing concentrations of cCTLA-4 by ELISA. 0.25 ug/ml of soluble scFvs were added to each well and bound scFvs were detected using an AP-conjugated anti-HA antibody. All clones bound to cCTLA-4 with a range of affinities. A soluble single chain directed against the irrelevant MERS protein was used as a negative control. A commercially available polyclonal anti-CTLA-4 antibody was used as a positive control in one assay (top left graph).

Figure 15:
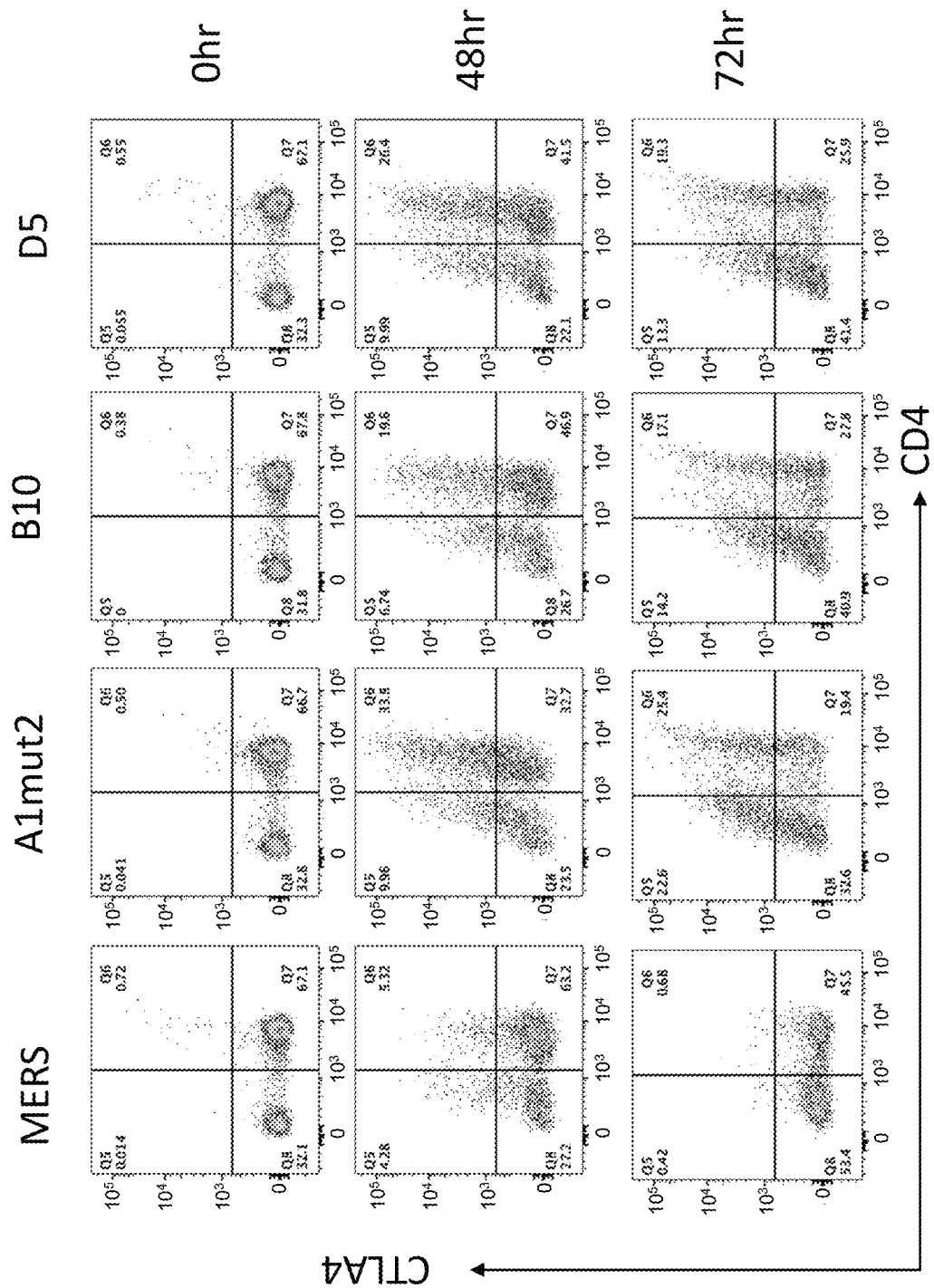

FIG. 15 illustrates the binding of anti-CTLA-4 mAb clones to activated canine T cells. Canine PBMCs were activated with 2.5 ug/ml Concanavalin A, harvested at 48 hr and 72 hr post activation and labeled with each HA-tagged anti-CTLA-4 mAb clone as indicated. Bound anti-CTLA-4 antibody was detected using an anti-HA antibody. Plots are gated on CD5+, 7AAD-cells.

Figure 16:
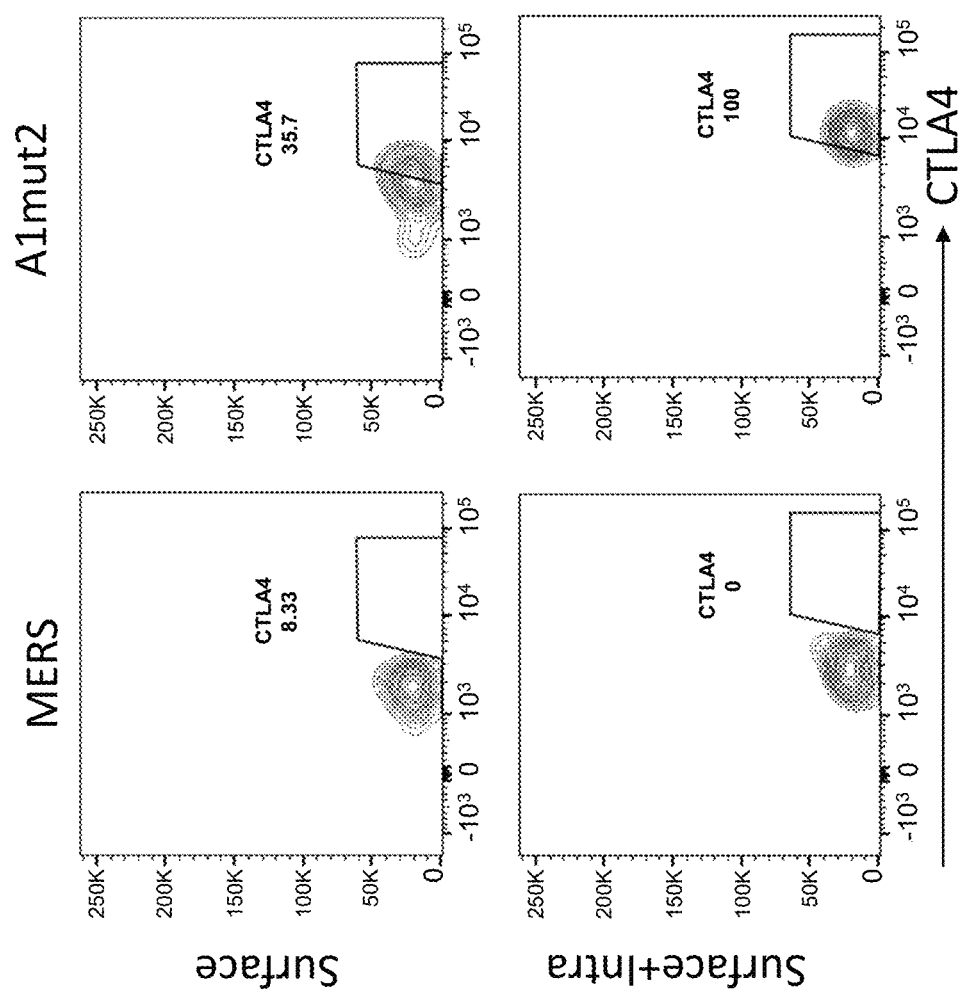

FIG. 16 illustrates the binding of A1mut2 mAb to canine regulatory T cells. Canine PBMCs from a dog with T cell lymphoma were first surface labeled with either A1mut2 or the irrelevant MERS mAb and then permeabilized and labeled with an anti-FOXP3 mAb (top row). In parallel, following permeabilization, cells were labeled again with either anti-MERS antibody or A1mut2 and Foxp3, to detect intracellular storers of CTLA-4 (bottom row). Plots are gated on CD45+, CD5+, CD4+ and FOXP3+ cells.

Figure 17A:
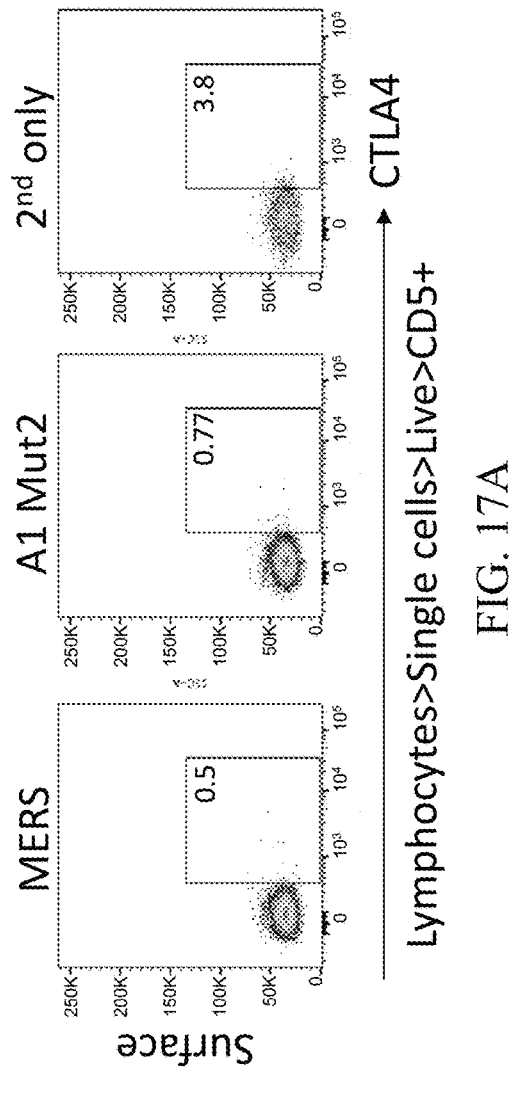
Figure 17B:
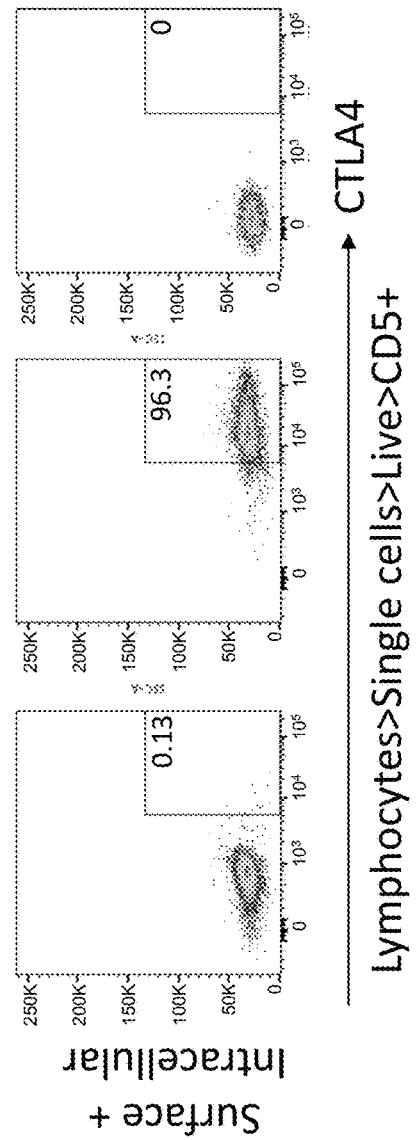

FIGS. 17A-17B illustrate the evaluation of A1mut2 binding to feline CTLA-4. PBMCs from 2 cats with lymphoid malignancies were surface labeled with CD5 and either HA-tagged A1mut2 or the irrelevant MERS mAb (FIG.

17A). Labeled cells were then permeabilized and labeled again with MERS or A1mut2 to detect intracellular stores of CTLA-4 (FIG. 17B). The anti-HA secondary antibody alone is used as an additional negative control. Plots are gated on CD5+ lymphocytes.

Figure 18B:
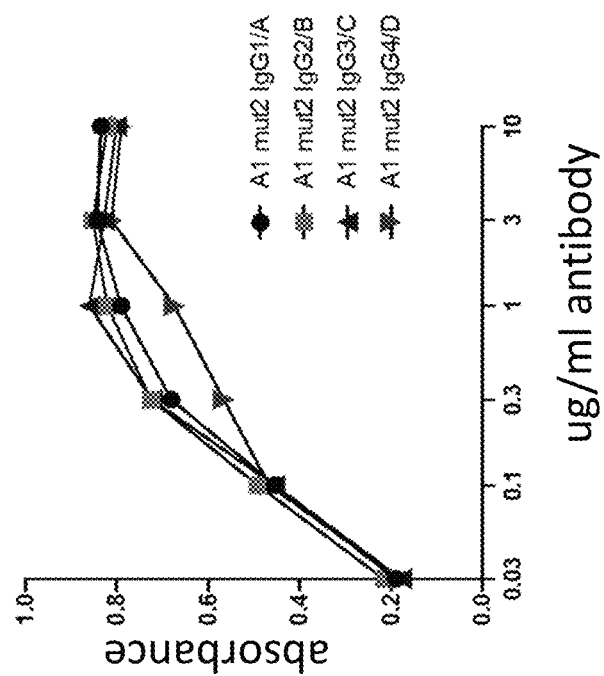
Figure 18A:
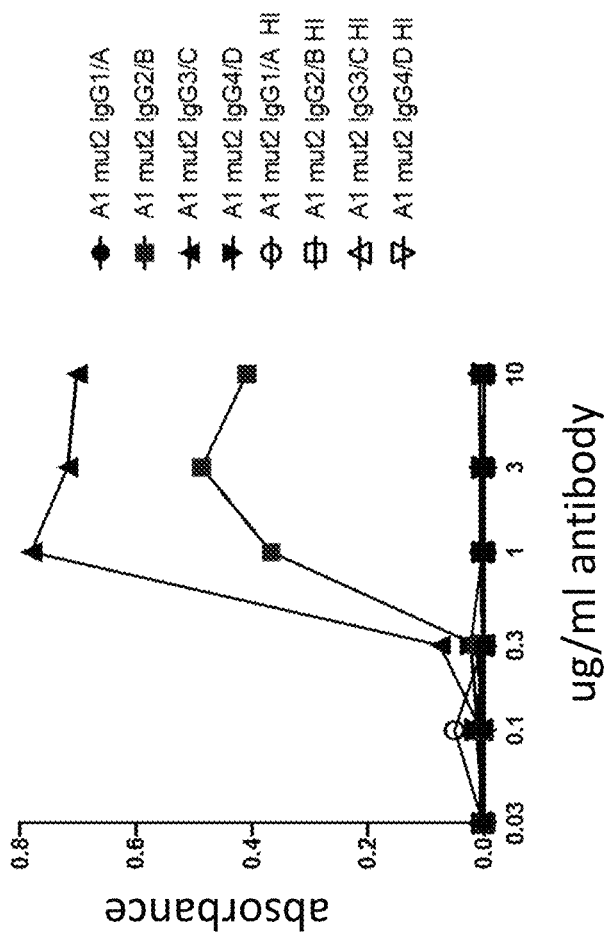

FIGS. 18A-18B illustrate that A1mut2 expressed as canine isotypes IgG$_C$ (canine IgG3), and IgG$_B$ (canine IgG2) fix human complement. FIG. 18A. Serial dilutions of HA-tagged A1mut2 reformatted as each of the four different IgG subclasses were allowed to bind to SA captured biotinylated cCTLA-4. Human serum complement or heat inactivated (HI) human serum complement was added to the plate and subsequently detected with an anti-human C1q IgG HRP conjugate and HRP substrate. FIG. 18B. Confirmation of the presence of A1mut2 IgG subclasses bound to cCTLA-4. Serial dilutions of A1mut2 IgG bound to canine CTLA-4 were detected using an AP-conjugated anti-HA IgG and AP substrate.

Figures 19A, 19B:
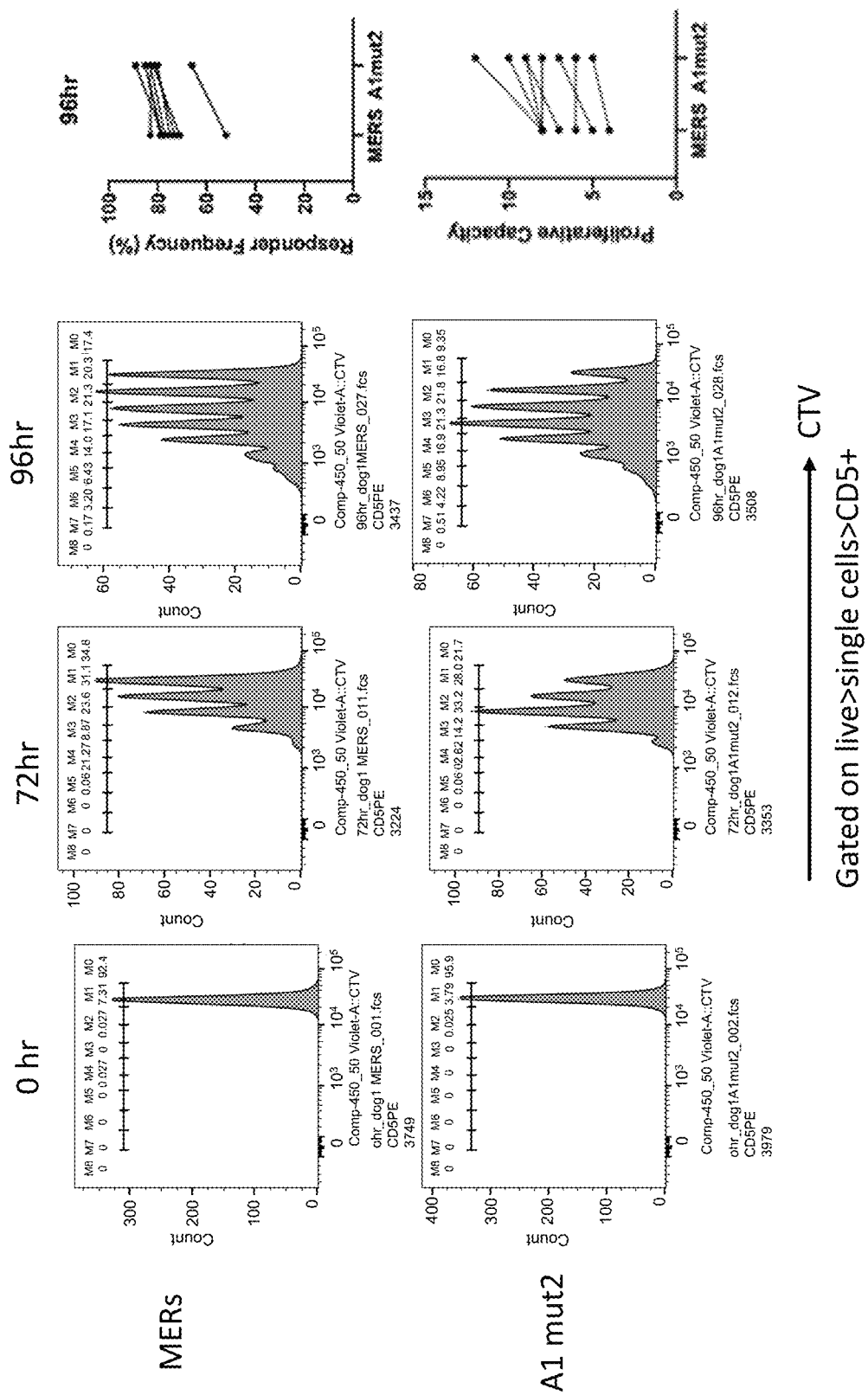

FIGS. 19A-19B illustrate that A1mut2 increases the responder frequency and proliferative capacity of canine T cells. Canine PBMCs were labeled with CellTrace™ Violet (CTV) proliferation dye and stimulated with ConA at 2.5 ug/ml in the presence of 10 ug/ml of either A1mut2 or the irrelevant MERS antibody. Cells were harvested at 72 or 96 hr and labeled with an anti-CD5 mAb and the viability dye 7-AAD. Cells were acquired on a FACSCanto™ II and analyzed by FlowJo software. Responder frequency (number of cells undergoing at least one division) and proliferative capacity (average number of daughter cells produced per cell) were determined. FIG. 19A. Representative histogram from one dog. FIG. 19B. Responder frequency and proliferative capacity of 9 healthy dogs calculated at 96 hours post stimulation.

Figure 20:
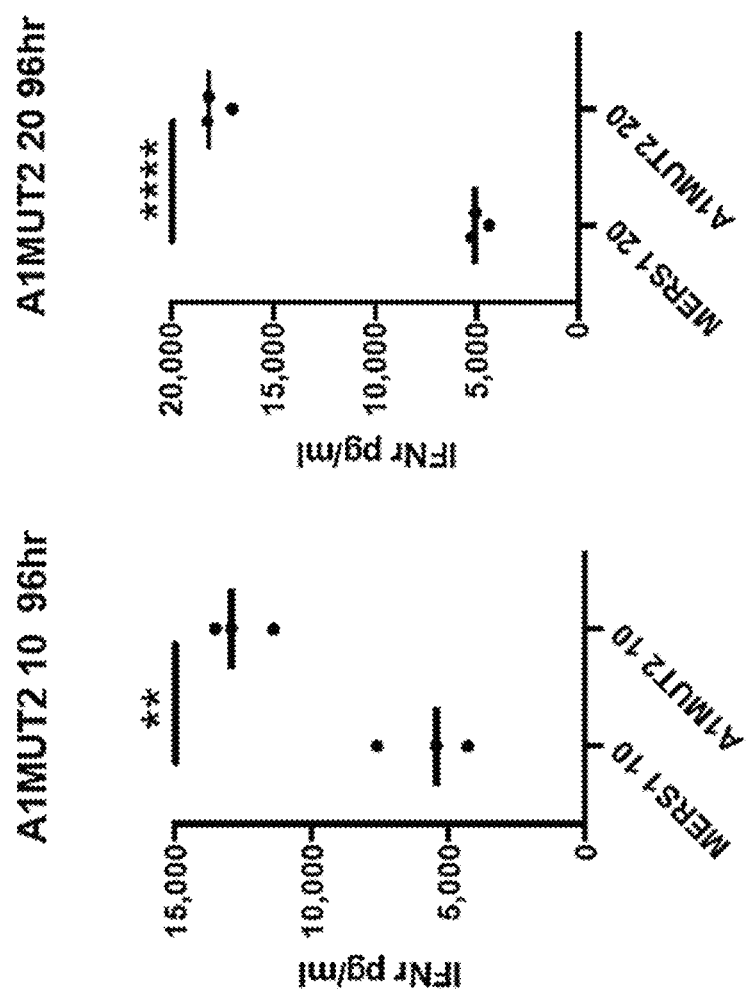

FIG. 20 illustrates that A1mut2 increases the production of IFN-γ from canine T cells. Canine PBMCs were stimulated with ConA at 2.5 ug/ml in the presence of either 10 ug/ml or 20 ug/ml of either A1mut2 or the irrelevant MERS antibody. Supernatants were harvested at 96 hr and IFN-γ present in the supernatants was determined by ELISA. Data from experimental triplicates of one healthy donor dog is shown. Horizontal bars represent the median value.

FIG. 21 is a table displaying kinetic rate constants of canine anti-cCTLA-4 binding, dissociation equilibrium constants, and half-lives of antibody/antigen interactions by selected full-length canine mAbs using surface plasmon resonance (SPR).

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules comprising two heavy chain and two light chain polypeptides. Each polypeptide chain contains three complementarity-determining regions (CDRs), which bind to the antigen and defines the antibody's antigen specificity.

As used herein, the term "antibody" and "antibodies" can also include polypeptides or polypeptide complexes derived from full-length antibodies. These polypeptide complexes may be naturally occurring or constructed from single chain antibodies or antibody fragments and retain an antigen-specific binding ability. The antibodies of the present invention may exist in a variety of forms including, for example, polyclonal antibodies, monoclonal antibodies, Fv, Fab and F(ab')$_2$, as well as single chain antibodies (scFv), caninized antibodies, canine antibodies, humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a polypeptide comprising or derived from a portion of an intact antibody and comprises the antigen-binding determining variable regions of an intact antibody. Examples of antibody fragments include, but are not limited to, Fab, Fab', F(ab')$_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind GFRα4 using the functional assays described herein.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to, an MHC class I molecule, BTLA and a Toll ligand receptor.

The term "dysregulated" when used in the context of the level of expression or activity of CTLA-4 refers to the level of expression or activity that is different from the expression level or activity of CTLA-4 in an otherwise identical healthy animal, organism, tissue, cell or component thereof. The term "dysregulated" also refers to the altered regulation of the level of expression and activity of CTLA-4 compared to the regulation in an otherwise identical healthy animal, organism, tissue, cell or component thereof.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" or "caninized" and "chimeric" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized, caninized, and chimeric antibodies are human or canine immunoglobulins (recipient antibody) in which residues from a complementary-determining region (CDR) of the recipient are replaced by residues from a CDR of a non-human or non-canine species (donor antibody) such as mouse, rat or rabbit having the desired specificity, affinity, and capacity. In some instances, Fv framework region (FR) residues of the human or canine immunoglobulin are replaced by corresponding non-human or non-canine residues. Furthermore, humanized, caninized, and chimeric antibodies can comprise residues which are found neither in the recipient antibody nor in the imported CDR or framework sequences. These modifications are made to further refine and optimize antibody performance. In general, the humanized, caninized, and chimeric antibody will comprise substantially all of at least one, and typically two, variable domains, in which all or substantially all of the CDR regions correspond to those of a non-human immunoglobulin and all or substantially all of the FR regions are those of a human or canine immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GFRα4.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell and/or on a tumor cell.

A "stimulatory ligand," as used herein, means a ligand that when present on an antigen presenting cell (e.g., an aAPC, a dendritic cell, a B-cell, and the like) or a tumor cell, can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based on the discovery that canine antibody phage display libraries can be used to identify antigen-specific single-chain variable fragment (scFv) fusion proteins that specifically bind cytotoxic T lymphocyte protein 4 (CTLA-4) of canine origin. These canine CTLA-4 specific scFv can then be converted into full-length antibodies possessing canine constant regions, making them suitable for in vivo use in canine subjects. Also provided are methods and compositions comprising the canine CTLA-4 specific scFv, antibodies, or antigen-binding fragments of the invention for the treatment of cancers.

Cytotoxic T lymphocyte associated protein 4 (CTLA-4) or CD152 is a member of the immunoglobulin superfamily of transmembrane receptors that is highly homologous with the T cell co-stimulatory molecule CD28. CTLA-4 is up-regulated on the surface of $CD4^+$ and $CD8^+$ T cells following their activation and serves as a negative regulator of effector T cell responses. CTLA-4 is also over-expressed on the surface of exhausted $CD8^+$ T cells. CTLA-4 binds CD80 and CD86 with high affinity, out-competing CD28 for interaction with these receptor ligands and inhibiting T cell activation. Inhibition of lymphocyte activation by CTLA-4 is achieved not only by out-competing CD28, but also via recruitment of the tyrosine phosphatase SHP2 and the serine threonine phosphatase PP2A which dephosphorylate the TCRζ chain and target downstream effectors of PI3K respectively. CTLA-4 can further inhibit effector T cell responses indirectly via its effects on antigen-presenting cells (APC). The high binding affinity of CTLA-4 for CD80/86 on APCs can lead to the removal of these co-stimulatory ligands via transendocytosis, promoting a tolerogenic APC phenotype. In contrast to effector T cells, regulatory T cells constitutively express CTLA-4 on their surface and this is essential for their suppressor activity, particularly their ability to inhibit dendritic cell maturation. Monoclonal antibodies that bind to CTLA-4 and inhibit its interaction with CD80/86 enhance endogenous T cell responses, inhibit Treg function and promote anti-tumor immunity by lowering the T cell activation threshold and promoting proliferation of highly activated, tumor-specific T cells.

Ipilimumab, aka Yervoy, was the first anti-CTLA-4 monoclonal antibody approved by the FDA in 2011 for the treatment of melanoma in human patients and has become a frontline therapy in the clinic. Given the similarity between the human and canine immune systems, the present invention provides a fully canine anti-CTLA-4 that can be used as an anti-tumor therapy in dogs. Utilizing a recently developed canine scFv phage display library, three CTLA-4-specific soluble scFvs were identified and reformatted into fully canine IgG monoclonal antibodies, which can be used as immunotherapies for veterinary cancers.

Immunotherapy for Canine Cancers

Dogs are closely related phylogenetically to humans and spontaneously develop cancer that shares similar biological, behavioral and genetic features with human counterparts. As such, the canine cancer patient can serve as a relevant parallel patient population to assist in unravelling the mechanisms of action of anti-CTLA-4 mAbs, identifying correlative biomarkers of response and understanding mechanisms of resistance to checkpoint inhibitors. Further, they may also play an important translational role in informing human clinical trial design regarding the safety and efficacy of combination therapies. Canine CTLA-4 (NP_001003106.1) shares 88% identity with human CTLA-4 (NP_005205.2) and was shown to induce tolerance in dogs following the administration of sheep red blood cells suggesting a conserved mechanism of action of CTLA-4 between human and dog. In addition, a higher percentage of canine peripheral blood CD4$^+$ and CD8$^+$ T cells expressed CTLA-4 in canine patients with histiocytic sarcoma and B cell lymphoma compared to control dogs suggesting the presence of an exhausted phenotype in these dogs which adversely affects anti-tumor immunity. Furthermore, recent reports using RNAseq have confirmed that canine CD4$^+$ CD25$^+$ T cells express a regulatory phenotype that includes expression of high levels of CTLA-4 transcripts. Together, these findings provide the rationale for development of a therapeutic canine anti-CTLA-4 antibody that could promote anti-tumor immunity in these aggressive tumor types and provide a valuable comparable reagent to investigate correlative biomarkers of clinical response and optimal combination therapies to inform human clinical trials.

Binding Polypeptides, Antibodies, and scFvs

The binding polypeptides and antibodies of the invention are characterized by particular functional features or properties of the antibodies. For example, the binding polypeptides and antibodies specifically bind to canine cytotoxic T lymphocyte associated protein 4 (CTLA-4). Preferably, the binding polypeptides and antibodies of the invention bind to canine CTLA-4 with high affinity. Preferably, the binding polypeptides and antibodies of the invention specifically recognize naturally expressed canine CTLA-4 protein on a cell and do not cross-react to other surface molecules on that cell.

In certain aspect, the invention provides an isolated binding polypeptide comprising an antigen-binding domain that specifically binds to an epitope of canine cytotoxic T lymphocyte associated protein 4 (CTLA-4). In certain embodiments, the antigen-binding domain comprises a heavy chain variable region that comprises three heavy chain complementarity determining regions (HCDRs) and a light chain variable region that comprises three light chain complementarity determining regions (LCDRs).

In certain aspects, the invention provides an isolated binding polypeptide comprising an HCDR1 comprising the amino acid sequences (SEQ ID NOs: 1, 21, or 37). Also provided is an isolated binding polypeptide comprising an HCDR2 comprising the amino acid sequences (SEQ ID NOs: 2, 22, or 38). Also provided is an isolated binding polypeptide comprising an HCDR3 comprising the amino acid sequences (SEQ ID NOs: 3, 23, or 39). Also provided is an isolated binding polypeptide comprising a light chain variable region that comprises an LCDR1 comprising the amino acid sequences (SEQ ID NO: 4, 24, or 40). Also provided is an isolated binding polypeptide comprising an LCDR2 comprising the amino acid sequences (SEQ ID NOs: 5, 25, or 41). Also provided is an isolated binding polypeptide comprising an LCDR3 comprising the amino acid sequences (SEQ ID NO: 6, 26, or 42).

In certain aspects, the invention provides an isolated binding polypeptide comprising an HCDR1 comprising the amino acid sequence (SEQ ID NO: 1), an HCDR2 comprising the amino acid sequence (SEQ ID NO: 2), an HCDR3 comprising the amino acid sequence (SEQ ID NO: 3), an LCDR1 comprising the amino acid sequence (SEQ ID NO: 4), an LCDR2 comprising the amino acid sequence (SEQ ID NO: 5), and an LCDR3 comprising the amino acid sequence (SEQ ID NO: 6).

Tolerable variations of the complementarity determining regions (CDR) sequences will be known to those of skill in the art. For example, in some embodiments the polypeptide comprises a complementarity determining region (HCDR or LCDR) that comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs: 1, 2, 3, 4, 5, 6, 21, 22, 23, 24, 25, 26, 37, 38, 39, 40, 41, or 42.

In some embodiments, the binding polypeptide binds a cytotoxic T lymphocyte associated protein 4 (CTLA-4). In some embodiments the CTLA-4 protein comprises the amino acid set forth in SEQ ID NO: 53. In some embodiments, the binding polypeptide comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a canine antibody or an antigen-binding fragment thereof. In some embodiments, the antibody or antigen-binding fragment is a caninized antibody or an antigen-binding fragment thereof.

In certain embodiments, the binding polypeptide comprises a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NOs: 6, 25, 40, or 74. In certain embodiments, the binding polypeptide comprises a heavy chain variable region comprising an amino acid sequence set forth in SEQ ID NOs: 6, 25, 40, or 74. In certain embodiments, the binding polypeptide consists of a heavy chain variable region consisting of an amino acid sequences set forth in SEQ ID NO: 6, 25, 40, or 74.

In certain embodiments, the binding polypeptide comprises a light chain variable region comprising an amino acid sequence having at least 80%, 85%, 90%, 95%, 96%, 97%, 98%, 99% identity to the amino acid sequence set forth in SEQ ID NOs: 8, 27, or 42. In certain embodiments, the binding polypeptide comprises a light chain variable region comprising an amino acid sequence set forth in SEQ ID NOs: 8, 27, or 42. In certain embodiments, the binding polypeptide consists of a light chain variable region comprising an amino acid sequence set forth in SEQ ID NOs: 8, 27, or 42.

Also provided is an isolated binding polypeptide comprising a heavy chain variable region comprising the amino acid sequence set forth in SEQ ID NO: 6 and a light chain variable region comprising the amino acid sequence set forth in SEQ ID NO: 8.

In certain embodiments, the invention includes an antibody that binds to the same epitope on canine CTLA-4 as an antibody of the invention (i.e., antibodies that have the ability to cross-compete for binding to canine CTLA-4 with any of the antibodies of the invention). In a preferred embodiment, the reference antibody for cross-competition studies can be one of the antibodies described herein (e.g., A1mut2). For example, Biacore analysis, ELISA assays or flow cytometry may be used to demonstrate cross-competition with the antibodies of the current invention. The ability of a test antibody to inhibit the binding of, for example, A1mut2, to canine CTLA-4 demonstrates that the test antibody can compete with A1mut2 for binding to canine CTLA-4 and thus is considered to bind to the same epitope of CTLA-4 as A1mut2.

An antibody of the invention can be prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

Also provided is a single-chain variable fragment (scFv) comprising an antigen-binding domain that specifically binds to an epitope of canine cytotoxic T lymphocyte associated protein 4 (CTLA-4).

As used herein, the term "single-chain variable fragment" or "scFv" is a fusion protein of the variable regions of the heavy (VH) and light chains (VL) of an immunoglobulin (e.g., mouse or human) covalently linked to form a VH:VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., CTLA-4 binding domain) comprises an scFv having the configuration from N-terminus to C-terminus, VH-linker-VL. In some embodiments, the antigen binding domain comprises an scFv having the configuration from N-terminus to C-terminus, VL-linker VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6): 1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO: 58), $(GGGS)_n$ (SEQ ID NO: 59), and $(GGGGS)_n$ (SEQ ID NO: 60), where n represents an integer of at least 1. Exemplary linker sequences can comprise amino acid sequences including, without limitation, GGSG (SEQ ID NO: 61), GGSGG (SEQ ID NO: 62), GSGSG (SEQ ID NO:63), GSGGG (SEQ ID NO: 64), GGGSG (SEQ ID NO: 65), GSSSG (SEQ ID NO:66), GGGGS (SEQ ID NO: 67), GGGGSGGGGSGGGGS (SEQ ID NO: 68), GGGSSRSSSSGGGGSGGGG (SEQ ID NO: 69) and the like. Those of skill in the art would be able to select the appropriate linker sequence for use in the present invention. In one embodiment, an scFv of the present invention comprises a heavy chain variable region (VH) and a light chain variable region (VL), wherein the VH and VL is separated by the linker sequence having the amino acid sequence GGGSSRSSSSGGGGSGGGG (SEQ ID NO: 69), which may be encoded by the nucleic acid sequence GGCGGTGGTTCCTCTAGATCTTCCTCCTCTGGTGG CGGTGGCTCGGGCGGTGGTGGG (SEQ ID NO: 70).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

In certain embodiments, the antigen-binding domain of the scFv comprises a heavy chain variable region that comprises three heavy chain complementarity determining regions (HCDRs) and a light chain variable region that comprises three light chain complementarity determining regions (LCDRs). HCDR1 comprises the amino acid sequence (SEQ ID NOs: 1, 17, or 33), and/or HCDR2 comprises the amino acid sequence (SEQ ID NOs: 2, 18, or 34), and/or HCDR3 comprises the amino acid sequence (SEQ ID NO: 3, 19, or 35) and/or LCDR1 comprises the amino acid sequence (SEQ ID NOs: 4, 20, or 36), and/or LCDR2 comprises the amino acid sequence (SEQ ID NO: 5, 21, or 37), and/or LCDR3 comprises the amino acid sequence (SEQ ID NO: 6, 22, or 38). The heavy chain variable region and the light chain variable region are separated by a linker.

Also provided is a single-chain variable fragment (scFv) comprising a heavy chain variable region comprising the amino acid sequence set forth in SEQ ID NOs: 6, 25, 40, or 74 and a light chain variable region comprising the amino acid sequence set forth in SEQ ID NO: 8, 27, or 42. The heavy chain variable region and the light chain variable region are separated by a linker.

In another aspect, a single chain variable fragment (scFv) comprising an amino acid sequence set forth in SEQ ID NOs: 29, 44, or 76, is provided. In another aspect, a single chain variable fragment (scFv) consisting of an amino acid sequence set forth in SEQ ID NOs: 29, 44, or 76, is provided.

Tolerable variations of the scFv sequences will be known to those of skill in the art. For example, in some embodiments the scFv comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs: 29, 44, or 76.

In another aspect, a full-length antibody comprising a heavy chain comprising an amino acid sequence set forth in SEQ ID NOs: 10, 12, 14, 16, 31, 46, 71, 72, or 73 and a light chain comprising an amino acid sequence set forth in SEQ ID NOs: 18, 33, or 48 is provided. In another aspect, a full-length antibody consisting of a heavy chain comprising an amino acid sequence set forth in SEQ ID NOs: 10, 12, 14, 16, 31, 46, 71, 72, or 73 and a light chain comprising an amino acid sequence set forth in SEQ ID NOs: 18, 33, or 48 is provided. Tolerable variations of the full-length antibody sequences will be known to those of skill in the art. For example, in some embodiments the antibody comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs: 11, 13, 15, 17, 19, 33, 35, 49, and 51.

TABLE 1

Sequences used in the invention

| SEQ ID NO: | Name | Type | Sequence |
|---|---|---|---|
| 1 | A1 HCDR1 | Protein | GFSFSSYA |
| 2 | A1 HCDR2 | Protein | INSGGSST |
| 3 | A1 HCDR3 | Protein | AISNWAY |
| 4 | A1 LCDR1 | Protein | SSDIGKSY |
|  | A1 LCDR2 | Protein | VDG |
| 5 | A1 LCDR3 | Protein | SSWDWSLHTYV |
| 6 | A1mut2 VH | Protein | EVQLVETGGDLVKPGGSLRLSCVASGFSFSSYAMNWVRQ APEKGLQLVGGINSGGSSTYYTDAVKGRFTISRDNAKNTV YLQMNSLRAEDTAVYYCAISNWAYWGQGTLVTVSS |
| 7 | A1mut2 VH | DNA | GAGGTGCAGCTGGTGGAGACCGGGGGAGACCTGGTGA AGCCTGGCGGGTCCCTGAGATTGTCCTGTGTGGCCTCTG GATTCTCCTTCAGCAGTTATGCCATGAACTGGGTCCGCC AGGCTCCTGAGAAGGGGCTGCAGCTGGTGGGCGGTATT AATAGCGGTGGAAGTAGTACATATTACACCGACGCTGT GAAGGGCCGCTTCACCATCTCCAGAGACAACGCCAAGA ACACAGTGTATTTACAGATGAATAGCCTGAGAGCCGAG GACACGGCCGTGTATTACTGTGCGATTAGTAATTGGGCC TACTGGGGCCAGGGAACCCTGGTCACCGTCTCCTCA |
| 8 | A1 VL | Protein | QAVLNQPASVSGSLGQRVTISCTGSSSDIGKSYVAWYQQL PGTGPRTLINVDGNRASGVPDRFSVSRSGNTATLTISGLQA EDEADYHCSSWDWSLHTYVFGSGTQLTIL |
| 9 | A1 VL | DNA | CAGGCTGTGCTGAATCAGCCGGCCTCAGTGTCCGGGTC CCTGGGCCAGAGGGTCACCATCTCCTGCACTGGAAGCA GCTCCGACATCGGTAAAAGTTATGTGGCCTGGTACCAG CAGCTCCCGGGAACAGGCCCCAGAACCCTCATCAATGT TGATGGTAACCGAGCCTCAGGGGTCCCCGATCGATTCTC TGTCTCCAGGTCAGGCAACACAGCCACCCTGACCATCTC CGGGCTCCAGGCTGAGGATGAGGCTGATTATCACTGCT CATCCTGGGACTGGAGTCTCCATACTTACGTGTTCGGCT CAGGGACCCAGCTGACCATCCTC |
| 10 | A1mut2 heavy chain full-length cIgG1 | Protein | MYRMQLLSCIALSLALVINSEVQLVETGGDLVKPGGSLRL SCVASGFSFSSYAMNWVRQAPEKGLQLVGGINSGGSSTYY TDAVKGRFTISRDNAKNTVYLQMNSLRAEDTAVYYCAIS NWAYWGQGTLVTVSSASTTAPSVFPLAPSCGSTSGSTVAL ACLVSGYFPEPVTVSWNSGSLTSGVHTFPSVLQSSGLYSLS SMVTVPSSRWPSETFTCNVVHPASNTKVDKPVFNECRCTD TPPCPVPEPLGGPSVLIFPPKPKDILRITRTPEVTCVVLDLGR EDPEVQISWFVDGKEVHTAKTQSREQQFNGTYRVVSVLPI EHQDWLTGKEFKCRVNHIDLPSPIERTISKARGRAHKPSVY VLPPSPKELSSSDTVSVTCLIKDFYPPDIDVEWQSNGQQEP ERKHRMTPPQLDEDGSYFLYSKLSVDKSRWQQGDPFTCA VMHETLQNHYTDLSLSHSPGK |
| 11 | A1mut2 heavy chain full-length cIgG1 | DNA | ATGTACAGGATGCAACTCCTGTCTTGCATTGCACTAAGT CTTGCACTTGTCACGAATTCGGAGGTGCAGCTGGTGGA GACCGGGGGAGACCTGGTGAAGCCTGGCGGGTCCCTGA GATTGTCCTGTGTGGCCTCTGGATTCTCCTTCAGCAGTT ATGCCATGAACTGGGTCCGCCAGGCTCCTGAGAAGGGG CTGCAGCTGGTGGGCGGTATTAATAGCGGTGGAAGTAG TACATATTACACCGACGCTGTGAAGGGCCGCTTCACCAT CTCCAGAGACAACGCCAAGAACACAGTGTATTTACAGA TGAATAGCCTGAGAGCCGAGGACACGGCCGTGTATTAC TGTGCGATTAGTAATTGGGCCTACTGGGGCCAGGGAAC CCTGGTCACCGTCTCCTCAGCTAGCACCACGGCCCCCTC GGTTTTCCCACTGGCCCCAGCTGCGGGTCCACTTCCGG CTCCACGGTGGCCCTGGCCTGCCTGGTGTCAGGCTACTT CCCCGAGCCTGTAACTGTGTCCTGGAACTCCGGCTCCTT GACCAGCGGTGTGCACACCTTCCCGTCCGTCCTGCAGTC CTCAGGGCTCTACTCCCTCAGCAGCATGGTGACAGTGCC CTCCAGCAGATGGCCCAGTGAGACCTTCACCTGCAACG TGGTCCACCCGGCCAGCAACACTAAAGTAGACAAGCCA GTGTTCAATGAATGCAGATGCACTGATACACCCCCATG CCCAGTCCCTGAACCTCTGGGAGGGCCTTCGGTCCTCAT CTTTCCCCCGAAACCCAAGGACATCCTCAGGATTACCCG AACACCCGAGGTCACCTGTGTGGTGTTAGATCTGGGCC GTGAGGACCCTGAGGTGCAGATCAGCTGGTTCGTGGAT |

TABLE 1-continued

Sequences used in the invention

| SEQ ID NO: | Name | Type | Sequence |
|---|---|---|---|
|  |  |  | GGTAAGGAGGTGCACACAGCCAAGACGCAGTCTCGTGA<br>GCAGCAGTTCAACGGCACCTACCGTGTGGTCAGCGTCC<br>TCCCCATTGAGCACCAGGACTGGCTCACAGGGAAGGAG<br>TTCAAGTGCAGAGTCAACCACATAGACCTCCCATCTCCC<br>ATCGAGAGGACCATCTCTAAGGCCAGAGGGAGGGCCCA<br>TAAGCCCAGTGTGTATGTCCTGCCACCATCCCCAAAGG<br>AGTTGTCATCCAGTGACACAGTCAGCGTCACCTGCCTGA<br>TAAAAGACTTCTACCCACCTGACATTGATGTGGAGTGG<br>CAGAGCAATGGACAGCAGGAGCCTGAGAGGAAGCACC<br>GCATGACCCCGCCCCAGCTGGACGAGGACGGGTCCTAC<br>TTCCTGTACAGCAAGCTCTCTGTGGACAAGAGCCGCTG<br>GCAGCAGGGAGACCCCTTCACATGTGCGGTGATGCATG<br>AAACTCTACAGAACCACTACACAGATCTATCCCTCTCCC<br>ATTCTCCGGGTAAA |
| 12 | A1mut2 heavy chain full-length cIgG2 | Protein | MYRMQLLSCIALSLALVTNSEVQLVETGGDLVKPGGSLRL<br>SCVASGFSFSSYAMNWVRQAPEKGLQLVGGINSGGSSTYY<br>TDAVKGRFTISRDNAKNTVYLQMNSLRAEDTAVYYCAIS<br>NWAYWGQGTLVTVSSASTTAPSVFPLAPSCGSTSGSTVAL<br>ACLVSGYFPEPVTVSWNSGSLTSGVHTFPSVLQSSGLYSLS<br>SMVTVPSSRWPSETFTCNVAHPASKTKVDKPVPKRENGR<br>VPRPPDCPKCPAPEMLGGPSVFIFPPKPKDTLLIARTPEVTC<br>VVVDLDPEDPEVQISWFVDGKQMQTAKTQPREEQFNGTY<br>RVVSVLPIGHQDWLKGKQFTCKVNNKALPSPIERTISKAR<br>GQAHQPSVYVLPPSREELSKNTVSLTCLIKDFFPPDIDVEW<br>QSNGQQEPESKYRTTPPQLDEDGSYFLYSKLSVDKSRWQR<br>GDTFICAVMHEALHNHYTQESLSHSPGK |
| 13 | A1mut2 heavy chain full-length cIgG2 | DNA | ATGTACAGGATGCAACTCCTGTCTTGCATTGCACTAAGT<br>CTTGCACTTGTCACGAATTCGGAGGTGCAGCTGGTGGA<br>GACCGGGGGAGACCTGGTGAAGCCTGGCGGGTCCCTGA<br>GATTGTCCTGTGTGGCCTCTGGATTCTCCTTCAGCAGTT<br>ATGCCATGAACTGGGTCCGCCAGGCTCCTGAGAAGGGG<br>CTGCAGCTGGTGGGCGGTATTAATAGCGGTGGAAGTAG<br>TACATATTACACCGACGCTGTGAAGGGCCGCTTCACCAT<br>CTCCAGAGACAACGCCAAGAACACAGTGTATTTACAGA<br>TGAATAGCCTGAGAGCCGAGGACACGGCCGTGTATTAC<br>TGTGCGATTAGTAATTGGGCCTACTGGGGCCAGGGAAC<br>CCTGGTCACCGTCTCCTCAGCTAGCACCACGGCCCCCTC<br>GGTTTTCCCACTGGCCCCCAGCTGCGGGTCCACTTCCGG<br>CTCCACGGTGGCCCTGGCCTGCCTGGTGTCAGGCTACTT<br>CCCCGAGCCTGTAACTGTGTCCTGGAACTCCGGCTCCTT<br>GACCAGCGGTGTGCACACCTTCCCGTCCGTCCTGCAGTC<br>CTCAGGGCTCTACTCCCTCAGCAGCATGGTGACAGTGCC<br>CTCCAGCAGGTGGCCCAGCGAGACCTTCACCTGCAACG<br>TGGCCCACCCGGCCAGCAAAACTAAAGTAGACAAGCCA<br>GTGCCCAAAAGAGAAAATGGAAGAGTTCCTCGCCCACC<br>TGATTGTCCCAAATGCCCAGCCCCTGAAATGCTGGGAG<br>GGCCTTCGGTCTTCATCTTTCCCCCGAAACCCAAGGACA<br>CCCTCTTGATTGCCCGAACACCTGAGGTCACATGTGTGG<br>TGGTGGATCTGGACCCAGAAGACCCTGAGGTGCAGATC<br>AGCTGGTTCGTGGACGGTAAGCAGATGCAAACAGCCAA<br>GACTCAGCCTCGTGAGGAGCAGTTCAATGGCACCTACC<br>GTGTGGTCAGTGTCCTCCCCATTGGGCACCAGGACTGGC<br>TCAAGGGGAAGCAGTTCACGTGCAAAGTCAACAACAAA<br>GCCCTCCCATCCCCGATCGAGAGGACCATCTCCAAGGC<br>CAGAGGGCAGGCCCATCAGCCCAGTGTGTATGTCCTGC<br>CGCCATCCCGGGAGGAGTTGAGCAAGAACACAGTCAGC<br>TTGACATGCCTGATCAAAGACTTCTTCCCACCTGACATT<br>GATGTGGAGTGGCAGAGCAATGGACAGCAGGAGCCTG<br>AGAGCAAGTACCGCACGACCCCGCCCAGCTGGACGAG<br>GACGGGTCCTACTTCCTGTACAGCAAGCTCTCTGTGGAC<br>AAGAGCCGCTGGCAGCGGGGAGACACCTTCATATGTGC<br>GGTGATGCATGAAGCTCTACACAACCACTACACACAGG<br>AATCCCTCTCCCATTCTCCGGGTAAA |
| 14 | A1mut2 heavy chain full-length cIgG3 | Protein | MYRMQLLSCIALSLALVINSEVQLVETGGDLVKPGGSLRL<br>SCVASGFSFSSYAMNWVRQAPEKGLQLVGGINSGGSSTYY<br>TDAVKGRFTISRDNAKNTVYLQMNSLRAEDTAVYYCAIS<br>NWAYWGQGTLVTVSSASTTAPSVFPLAPSCGSQSGSTVAL<br>ACLVSGYIPEPVTVSWNSGSLTSGVHTFPSILQSSGLYSLSS<br>MVTVPSSRWPSETFTCNVAHPATNTKVDKPVVKECECKC<br>NCNNCPCPGCGLLGGPSVFIFPPKPKDILVTARTPTVTCVV<br>VDLDPENPEVQISWFVDSKQVQTANTQPREEQSNGTYRV<br>VSVLPIGHQDWLSGKQFKCKVNNKALPSPIEEIISKTPGQA<br>HQPNVYVLPPSRDEMSKNTVTLTCLVKDFFPPEIDVEWQS |

TABLE 1-continued

Sequences used in the invention

| SEQ ID NO: | Name | Type | Sequence |
|---|---|---|---|
| | | | NGQQEPESKYRMTPPQLDEDGSYFLYSKLSVDKSRWQRG<br>DTFICAVMHEALHNHYTQKSLSHSPGK |
| 15 | A1mut2 heavy chain full-length cIgG3 | DNA | ATGTACAGGATGCAACTCCTGTCTTGCATTGCACTAAGT<br>CTTGCACTTGTCACGAATTCGGAGGTGCAGCTGGTGGA<br>GACCGGGGGAGACCTGGTGAAGCCTGGCGGGTCCCTGA<br>GATTGTCCTGTGTGGCCTCTGGATTCTCCTTCAGCAGTT<br>ATGCCATGAACTGGGTCCGCCAGGCTCCTGAGAAGGGG<br>CTGCAGCTGGTGGGCGGTATTAATAGCGGTGGAAGTAG<br>TACATATTACACCGACGCTGTGAAGGGCCGCTTCACCAT<br>CTCCAGAGACAACGCCAAGAACACAGTGTATTTACAGA<br>TGAATAGCCTGAGAGCCGAGGACACGGCCGTGTATTAC<br>TGTGCGATTAGTAATTGGGCCTACTGGGGCCAGGGAAC<br>CCTGGTCACCGTCTCCTCAGCTAGCACCACGGCCCCCTC<br>GGTTTTCCCACTGGCCCCAGCTGTGGGTCCCAATCCGG<br>CTCCACGGTGGCCCTGGCCTGCCTGGTGTCAGGCTACAT<br>CCCCGAGCCTGTAACTGTGTCCTGGAACTCCGGCTCCTT<br>GACCAGCGGTGTGCACACCTTCCCGTCCATCCTGCAGTC<br>CTCAGGGCTCTACTCCCTCAGCAGCATGGTGACAGTGCC<br>CTCCAGCAGGTGGCCCAGCGAGACCTTCACCTGCAATG<br>TGGCCCACCCGGCCACCAACACTAAAGTAGACAAGCCA<br>GTGGTCAAAGAATGCGAGTGCAAGTGTAACTGTAACAA<br>CTGCCCATGCCCAGGTTGTGGCCTGCTGGGAGGGCCTTC<br>GGTCTTCATCTTTCCCCCAAAACCCAAGGACATCCTCGT<br>GACTGCCCGGACACCCACAGTCACTTGTGTGGTGGTGG<br>ATCTGGACCCAGAAAACCCTGAGGTGCAGATCAGCTGG<br>TTCGTGGATAGTAAGCAGGTGCAAACAGCCAACACGCA<br>GCCTCGTGAGGAGCAGTCCAATGGCACCTACCGTGTGG<br>TCAGTGTCCTCCCCATTGGGCACCAGGACTGGCTTTCAG<br>GGAAGCAGTTCAAGTGCAAAGTCAACAACAAAGCCCTC<br>CCATCCCCCATTGAGGAGATCATCTCCAAGACCCCAGG<br>GCAGGCCCATCAGCCTAATGTGTATGTCCTGCCGCCATC<br>GCGGGATGAGATGAGCAAGAATACGGTCACCCTGACCT<br>GTCTGGTCAAAGACTTCTTCCCACCTGAGATTGATGTGG<br>AGTGGCAGAGCAATGGACAGCAGGAGCCTGAGAGCAA<br>GTACCGCATGACCCCGCCCCAGCTGGATGAGGATGGGT<br>CCTACTTCCTATACAGCAAGCTCTCTGTGGACAAGAGCC<br>GCTGGCAGCGGGGAGACACCTTCATATGTGCGGTGATG<br>CATGAAGCTCTACACAACCACTACACACAGAAATCCCT<br>CTCCCATTCTCCGGGTAAA |
| 16 | A1mut2 heavy chain full-length cIgG4 | Protein | MYRMQLLSCIALSLALVTNSEVQLVETGGDLVKPGGSLRL<br>SCVASGFSFSSYAMNWVRQAPEKGLQLVGGINSGGSSTYY<br>TDAVKGRFTISRDNAKNTVYLQMNSLRAEDTAVYYCAIS<br>NWAYWGQGTLVTVSSASTTAPSVFPLAPSCGSTSGSTVAL<br>ACLVSGYFPEPVTVSWNSGSLTSGVHTFPSVLQSSGLYSLS<br>SMVTVPSSRWPSETFTCNVVHPASNTKVDKPVPKESTCKC<br>ISPCPVPESLGGPSVFIFPPKPKDILRITRTPEITCVVLDLGRE<br>DPEVQISWFVDGKEVHTAKTQPREQQFNSTYRVVSVLPIE<br>HQDWLTGKEFKCRVNHIGLPSPIERTISKARGQAHQPSVY<br>VLPPSPKELSSSDTVTLTCLIKDFFPPEIDVEWQSNGQPEPE<br>SKYHTTAPQLDEDGSYFLYSKLSVDKSRWQQGDPFTCAV<br>MHEALQNHYTDLSLSHSPGK |
| 17 | A1mut2 heavy chain full-length cIgG4 | DNA | ATGTACAGGATGCAACTCCTGTCTTGCATTGCACTAAGT<br>CTTGCACTTGTCACGAATTCGGAGGTGCAGCTGGTGGA<br>GACCGGGGGAGACCTGGTGAAGCCTGGCGGGTCCCTGA<br>GATTGTCCTGTGTGGCCTCTGGATTCTCCTTCAGCAGTT<br>ATGCCATGAACTGGGTCCGCCAGGCTCCTGAGAAGGGG<br>CTGCAGCTGGTGGGCGGTATTAATAGCGGTGGAAGTAG<br>TACATATTACACCGACGCTGTGAAGGGCCGCTTCACCAT<br>CTCCAGAGACAACGCCAAGAACACAGTGTATTTACAGA<br>TGAATAGCCTGAGAGCCGAGGACACGGCCGTGTATTAC<br>TGTGCGATTAGTAATTGGGCCTACTGGGGCCAGGGAAC<br>CCTGGTCACCGTCTCCTCAGCTAGCACCACGGCCCCCTC<br>GGTTTTCCCACTGGCCCCAGCTGCGGGTCCACTTCCGG<br>CTCCACGGTGGCCCTAGCCTGCCTGGTGTCAGGCTACTT<br>CCCCGAGCCTGTAACTGTGTCCTGGAACTCCGGCTCCTT<br>GACCAGCGGTGTGCACACCTTCCCGTCCGTCCTGCAGTC<br>CTCAGGGCTCTACTCCCTCAGCAGCATGGTGACAGTGCC<br>CTCCAGCAGGTGGCCCAGCGAGACCTTCACCTGCAACG<br>TGGTCCACCCGGCCAGCAACACTAAAGTAGACAAGCCA<br>GTGCCCAAAGAGTCCACCTGCAAGTGTATATCCCCATG<br>CCCAGTCCCTGAATCACTGGGAGGGCCTTCGGTCTTCAT<br>CTTTCCCCCGAAACCCAAGGACATCCTCAGGATTACCCG<br>AACACCCGAGATCACCTGTGTGGTGTTAGATCTGGGCC |

TABLE 1-continued

Sequences used in the invention

| SEQ ID NO: | Name | Type | Sequence |
|---|---|---|---|
| | | | GTGAGGACCCTGAGGTGCAGATCAGCTGGTTCGTGGAT
GGTAAGGAGGTGCACACAGCCAAGACGCAGCCTCGTGA
GCAGCAGTTCAACAGCACCTACCGTGTGGTCAGCGTCC
TCCCCATTGAGCACCAGGACTGGCTCACCGGAAAGGAG
TTCAAGTGCAGAGTCAACCACATAGGCCTCCCGTCCCCC
ATCGAGAGGACCATCTCCAAAGCCAGAGGGCAAGCCCA
TCAGCCCAGTGTGTATGTCCTGCCACCATCCCCAAAGGA
GTTGTCATCCAGTGACACGGTCACCCTGACCTGCCTGAT
CAAAGACTTCTTCCCACCTGAGATTGATGTGGAGTGGC
AGAGCAATGGACAGCCAGAGCCTGAGAGCAAGTACCA
CACGACTGCACCCCAGCTGGACGAGGACGGGTCCTACT
TCCTGTACAGCAAGCTCTCTGTGGACAAGAGCCGCTGG
CAGCAGGGAGACCCCTTCACATGTGCGGTGATGCATGA
AGCTCTACAGAACCACTACACAGATCTATCCCTCTCCCA
TTCTCCGGGTAAA |
| 18 | A1mut2 lambda light chain full-length | Protein | MYRMQLLSCIALSLALVTNSQAVLNQPASVSGSLGQRVTI
SCTGSSSDIGKSYVAWYQQLPGTGPRTLINVDGNRASGVP
DRFSVSRSGNTATLTISGLQAEDEADYHCSSWDWSLHTYV
FGSGTQLTILGQPKASPSVTLFPPSSEELGANKATLVCLISD
FYPSGVTVAWKADGSPITQGVETTKPSKQSNNKYAASSYL
SLTPDKWKSHSSFSCLVTHEGSTVEKKVAPAECS |
| 19 | A1mut2 lambda light chain full-length | DNA | ATGTACAGGATGCAACTCCTGTCTTGCATTGCACTAAGT
CTTGCACTTGTCACGAATTCGCAGGCTGTGCTGAATCAG
CCGGCCTCAGTGTCCGGGTCCCTGGGCCAGAGGGTCAC
CATCTCCTGCACTGGAAGCAGCTCCGACATCGGTAAAA
GTTATGTGGCCTGGTACCAGCAGCTCCCGGGAACAGGC
CCCAGAACCCTCATCAATGTTGATGGTAACCGAGCCTC
AGGGGTCCCCGATCGATTCTCTGTCTCCAGGTCAGGCAA
CACAGCCACCCTGACCATCTCCGGGCTCCAGGCTGAGG
ATGAGGCTGATTATCACTGCTCATCCTGGGACTGGAGTC
TCCATACTTACGTGTTCGGCTCAGGGACCCAGCTGACCA
TCCTAGGTCAGCCCAAGGCCTCCCCCTCGGTCACACTCT
TCCCGCCCTCCTCTGAGGAGCTCGGCGCCAACAAGGCC
ACCCTGGTGTGCCTCATCAGCGACTTCTACCCCAGCGGC
GTGACGGTGGCCTGGAAGGCAGACGGCAGCCCCATCAC
CCAGGGCGTGGAGACCACCAAGCCCTCCAAGCAGAGCA
ACAACAAGTACGCGGCCAGCAGCTACCTGAGCCTGACG
CCTGACAAGTGGAAATCTCACAGCAGCTTCAGCTGCCTT
GGTCACGCACGAGGGGAGCACCGTGGAGAAGAAGGTG
GCCCCCGCAGAGTGCTCTT |
| 20 | D5 HCDR1 | Protein | GFTFSSYS |
| 21 | D5 HCDR2 | Protein | INSGGSST |
| 22 | D5 HCDR3 | Protein | VISNWSY |
| 23 | D5 LCDR1 | Protein | ATNVGGGYD |
| | D5 LCDR2 | Protein | GNY |
| 24 | D5 LCDR3 | Protein | SSWDNSLTAYV |
| 25 | D5 VH | Protein | EVQLVETGGDLMKPGGSLRLSCVASGFTFSSYSMSWVRQ
APEKGLQLVAGINSGGSSTYYTDAVKGRFTISRDNAKNTL
YLQMNSLRDEDTAVYYCVISNWSYWGQGTLVTVSS |
| 26 | D5 VH | DNA | GAGGTGCAGCTGGTGGAGACTGGGGGAGACCTGATGAA
GCCTGGGGGGTCCCTGAGACTGTCCTGTGTGGCCTCTGG
ATTCACCTTCAGTAGCTACAGTATGAGTTGGGTCCGCCA
GGCTCCTGAGAAGGGGCTGCAGTTGGTCGCAGGTATTA
ACAGCGGTGGAAGTAGCACATACTACACAGACGCTGTG
AAGGGCCGATTCACCATCTCCAGAGACAACGCCAAGAA
CACGCTGTATCTGCAGATGAACAGTCTGAGAGATGAAG
ACACGGCAGTCTATTATTGTGTGATCAGTAATTGGTCCT
ACTGGGGCCAGGGAACCCTGGTCACCGTCTCCTCA |
| 27 | D5 VL | Protein | QPVLTQPPSVSAALGQRVTISCTGTATNVGGGYDVQWYQ
QFPGRPPKTIIYGNYNRPSGVPDRFSASTSGTTATLTISGLQ
AEDEANYYCSSWDNSLTAYVFGSGTQLTIL |
| 28 | D5 VL | DNA | CAGCCTGTGCTCACTCAGCCGCCCTCTGTGTCTGCGGCC
CTGGGACAGAGGGTCACCATCTCCTGCACTGGAACTGC
GACCAACGTCGGCGGCGGTTATGATGTACAATGGTACC |

TABLE 1-continued

Sequences used in the invention

| SEQ ID NO: | Name | Type | Sequence |
|---|---|---|---|
| | | | AGCAGTTTCCAGGAAGACCCCCTAAAACTATCATTTAC
GGTAATTACAATCGCCCCTCGGGGGTCCCAGATCGATTC
TCTGCCTCCACGTCAGGCACCACAGCCACCCTGACCATC
TCTGGGCTCCAGGCTGAGGATGAGGCTAATTATTACTGC
TCATCGTGGGACAACAGTCTCACTGCTTACGTTTTCGGC
TCAGGGACCCAGCTGACCATCCTC |
| 29 | D5 scFv | Protein | QPVLTQPPSVSAALGQRVTISCTGTATNVGGGYDVQWYQ
QFPGRPPKTIIYGNYNRPSGVPDRFSASTSGTTATLTISGLQ
AEDEANYYCSSWDNSLTAYVFGSGTQLTILGGGSSRSSSS
GGGGSGGGGEVQLVETGGDLMKPGGSLRLSCVASGFTFS
SYSMSWVRQAPEKGLQLVAGINSGGSSTYYTDAVKGRFTI
SRDNAKNTLYLQMNSLRDEDTAVYYCVISNWSYWGQGT
LVTVSSESPSPPNLTSGQAGQHHHHHHGAYPYDVPDYAS |
| 30 | D5 scFv | DNA | CAGCCTGTGCTCACTCAGCCGCCCTCTGTGTCTGCGGCC
CTGGGACAGAGGGTCACCATCTCCTGCACTGGAACTGC
GACCAACGTCGGCGGCGGTTATGATGTACAATGGTACC
AGCAGTTTCCAGGAAGACCCCCTAAAACTATCATTTAC
GGTAATTACAATCGCCCCTCGGGGGTCCCAGATCGATTC
TCTGCCTCCACGTCAGGCACCACAGCCACCCTGACCATC
TCTGGGCTCCAGGCTGAGGATGAGGCTAATTATTACTGC
TCATCGTGGGACAACAGTCTCACTGCTTACGTTTTCGGC
TCAGGGACCCAGCTGACCATCCTCGGCGGTGGTTCCTCT
AGATCTTCCTCCTCTGGTGGCGGTGGCTCGGGCGGTGGT
GGGGAGGTGCAGCTGGTGGAGACTGGGGGAGACCTGAT
GAAGCCTGGGGGGTCCCTGAGACTGTCCTGTGTGGCCT
CTGGATTCACCTTCAGTAGCTACAGTATGAGTTGGGTCC
GCCAGGCTCCTGAGAAGGGGCTGCAGTTGGTCGCAGGT
ATTAACAGCGGTGGAAGTAGCACATACTACACAGACGC
TGTGAAGGGCCGATTCACCATCTCCAGAGACAACGCCA
AGAACACGCTGTATCTGCAGATGAACAGTCTGAGAGAT
GAAGACACGGCAGTCTATTATTGTGTGATCAGTAATTG
GTCCTACTGGGGCCAGGGAACCCTGGTCACCGTCTCCTC
AGAGAGTCCATCCCCTCCAAACCTCACTAGTGGCCAGG
CCGGCCAGCACCATCACCATCACCATGGCGCATACCCG
TACGACGTTCCGGACTACGCTTCT |
| 31 | D5 heavy chain full-length cIgG1 | Protein | MYRMQLLSCIALSLALVTNSEVQLVETGGDLMKPGGSLR
LSCVASGFTFSSYSMSWVRQAPEKGLQLVAGINSGGSSTY
YTDAVKGRFTISRDNAKNTLYLQMNSLRDEDTAVYYCVIS
NWSYWGQGTLVTVSSASTTAPSVFPLAPSCGSTSGSTVAL
ACLVSGYFPEPVTVSWNSGSLTSGVHTFPSVLQSSGLYSLS
SMVTVPSSRWPSETFTCNVVHPASNTKVDKPVFNECRCTD
TPPCPVPEPLGGPSVLIFPPKPKDILRITRTPEVTCVVLDLGR
EDPEVQISWFVDGKEVHTAKTQSREQQFNGTYRVVSVLPI
EHQDWLTGKEFKCRVNHIDLPSPIERTISKARGRAHKPSVY
VLPPSPKELSSSDTVSVTCLIKDFYPPDIDVEWQSNGQQEP
ERKHRMTPPQLDEDGSYFLYSKLSVDKSRWQQGDPFTCA
VMHETLQNHYTDLSLSHSPGK |
| 32 | D5 heavy chain full-length cIgG1 | DNA | ATGTACAGGATGCAACTCCTGTCTTGCATTGCACTAAGT
CTTGCACTTGTCACGAATTCGGAGGTGCAGCTGGTGGA
GACTGGGGGAGACCTGATGAAGCCTGGGGGGTCCCTGA
GACTGTCCTGTGTGGCCTCTGGATTCACCTTCAGTAGCT
ACAGTATGAGTTGGGTCCGCCAGGCTCCTGAGAAGGGG
CTGCAGTTGGTCGCAGGTATTAACAGCGGTGGAAGTAG
CACATACTACACAGACGCTGTGAAGGGCCGATTCACCA
TCTCCAGAGACAACGCCAAGAACACGCTGTATCTGCAG
ATGAACAGTCTGAGAGATGAAGACACGGCAGTCTATTA
TTGTGTGATCAGTAATTGGTCCTACTGGGGCCAGGGAA
CCCTGGTCACCGTCTCCTCAGCTAGCACCACGGCCCCT
CGGTTTTCCCACTGGCCCCCAGCTGCGGGTCCACTTCCG
GCTCCACGTGGCCCTGGCCTGCTGGTGTCAGGCTACT
TCCCCGAGCCTGTAACTGTGTCCTGGAACTCCGGCTCCT
TGACCAGCGGTGTGCACACCTTCCCGTCCGTCCTGCAGT
CCTCAGGGCTCTACTCCCTCAGCAGCATGGTGACAGTGC
CCTCCAGCAGATGGCCCAGTGAGACCTTCACCTGCAAC
GTGGTCCACCCGGCCAGCAACACTAAAGTAGACAAGCC
AGTGTTCAATGAATGCAGATGCACTGATACACCCCCAT
GCCCAGTCCCTGAACCTCTGGGAGGGCCTTCGGTCCTCA
TCTTTCCCCCGAAACCCAAGGACATCCTCAGGATTACCC
GAACACCCGAGGTCACCTGTGTGGTGTTAGATCTGGGC
CGTGAGGACCCTGAGGTGCAGATCAGCTGGTTCGTGGA
TGGTAAGGAGGTGCACACAGCCAAGACGCAGTCTCGTG
AGCAGCAGTTCAACGGCACCTACCGTGTGGTCAGCGTC |

TABLE 1-continued

Sequences used in the invention

| SEQ ID NO: | Name | Type | Sequence |
|---|---|---|---|
| | | | CTCCCCATTGAGCACCAGGACTGGCTCACAGGGAAGGA GTTCAAGTGCAGAGTCAACCACATAGACCTCCCATCTCC CATCGAGAGGACCATCTCTAAGGCCAGAGGGAGGGCCC ATAAGCCCAGTGTGTATGTCCTGCCACCATCCCCAAAG GAGTTGTCATCCAGTGACACAGTCAGCGTCACCTGCCTG ATAAAAGACTTCTACCCACCTGACATTGATGTGGAGTG GCAGAGCAATGGACAGCAGGAGCCTGAGAGGAAGCAC CGCATGACCCCGCCCCAGCTGGACGAGGACGGGTCCTA CTTCCTGTACAGCAAGCTCTCTGTGGACAAGAGCCGCTG GCAGCAGGGAGACCCCTTCACATGTGCGGTGATGCATG AAACTCTACAGAACCACTACACAGATCTATCCCTCTCCC ATTCTCCGGGTAAA |
| 33 | D5 lambda light chain full-length | Protein | MYRMQLLSCIALSLALVTNSQPVLTQPPSVSAALGQRVTIS CTGTATNVGGGYDVQWYQQFPGRPPKTIIYGNYNRPSGV PDRFSASTSGTTATLTISGLQAEDEANYYCSSWDNSLTAY VFGSGTQLTILGQPKASPSVTLFPPSSEELGANKATLVCLIS DFYPSGVTVAWKADGSPITQGVETTKPSKQSNNKYAASSY LSLTPDKWKSHSSFSCLVTHEGSTVEKKVAPAECS |
| 34 | D5 lambda light chain full-length | DNA | ATGTACAGGATGCAACTCCTGTCTTGCATTGCACTAAGT CTTGCACTTGTCACGAATTCGCAGCCTGTGCTCACTCAG CCGCCCTCTGTGTCTGCGGCCCTGGGACAGAGGGTCAC CATCTCCTGCACTGGAACTGCGACCAACGTCGGCGGCG GTTATGATGTACAATGGTACCAGCAGTTTCCAGGAAGA CCCCCTAAAACTATCATTTACGGTAATTACAATCGCCCC TCGGGGGTCCCAGATCGATTCTCTGCCTCCACGTCAGGC ACCACAGCCACCCTGACCATCTCTGGGCTCCAGGCTGA GGATGAGGCTAATTATTACTGCTCATCGTGGGACAACA GTCTCACTGCTTACGTTTTCGGCTCAGGGACCCAGCTGA CCATCCTCGGTCAGCCCAAGGCCTCCCCCTCGGTCACAC TCTTCCCGCCCTCCTCTGAGGAGCTCGGCGCCAACAAGG CCACCCTGGTGTGCCTCATCAGCGACTTCTACCCCAGCG GCGTGACGGTGGCCTGGAAGGCAGACGGCAGCCCCATC ACCCAGGGCGTGGAGACCACCAAGCCCTCCAAGCAGAG CAACAACAAGTACGCGGCCAGCAGCTACCTGAGCCTGA CGCCTGACAAGTGGAAATCTCACAGCAGCTTCAGCTGC CTGGTCACGCACGAGGGGAGCACCGTGGAGAAGAAGG TGGCCCCCGCAGAGTGCTCTT |
| 35 | B10 HCDR1 | Protein | GFTFSDYP |
| 36 | B10 HCDR2 | Protein | INSGGSAT |
| 37 | B10 HCDR3 | Protein | ATSNFQY |
| 38 | B10 LCDR1 | Protein | NTNIGSPYD |
| | B10 LCDR2 | Protein | GNS |
| 39 | B10 LCDR3 | Protein | QSYDDNVDGYV |
| 40 | B10 VH | Protein | EVQLVETGGDLVKPGGSLRLSCVASGFTFSDYPMNWVRQ APEKGLQLVGGINSGGSATYYTDAVKGRFTISRDNAKNTV YLQMNSLRAEDTAMYYCATSNFQYWGQGTLVTVSS |
| 41 | B10 VH | DNA | GAGGTGCAGCTGGTGGAGACTGGGGGAGATCTGGTGAA GCCTGGGGGATCCCTGAGACTCTCTTGTGTGGCCTCTGG ATTCACCTTCAGTGACTACCCCATGAACTGGGTCCGCCA GGCTCCTGAGAAGGGGCTGCAGTTGGTCGGTGGTATTA ACAGCGGTGGAAGTGCTACATACTACACAGACGCTGTG AAGGGCCGATTCACCATCTCCAGAGACAACGCCAAGAA CACAGTGTATCTGCAGATGAACAGCCTGAGAGCCGAGG ACACGGCCATGTATTACTGTGCAACGTCTAATTTTCAGT ACTGGGGCCAGGGAACCCTGGTCACCGTCTCCTCA |
| 42 | B10 VL | Protein | QAVLNQPASVSAALGQRVTISCNTNIGSPYDVQWYQQLPG KSPKTIIYGNSNRPSGVPVRFSGSKSGSTATLTIAGIQAEDE ADYYCQSYDDNVDGYVFGSGTQLTVL |
| 43 | B10 VL | DNA | CAGGCTGTGCTGAATCAGCCGGCCTCTGTGTCTGCAGCC CTGGGGCAGAGGGTCACCATCTCCTGTAACACCAACAT CGGCAGTCCTTATGATGTACAATGGTACCAGCAGCTCCC AGGAAAGTCCCCTAAAACTATCATTTATGGTAATAGCA ATCGACCCTCGGGGGTCCCGGTTCGATTCTCTGGCTCCA AGTCAGGCAGCACAGCCACCCTGACCATCGCTGGGATC |

TABLE 1-continued

Sequences used in the invention

| SEQ ID NO: | Name | Type | Sequence |
|---|---|---|---|
| | | | CAGGCTGAGGATGAGGCTGATTATTACTGCCAGTCCTAT<br>GATGACAACGTCGATGGTTACGTGTTCGGCTCAGGGAC<br>CCAACTGACCGTCCTT |
| 44 | B10 scFv | Protein | QAVLNQPASVSAALGQRVTISCNTNIGSPYDVQWYQQLPG<br>KSPKTIIYGNSNRPSGVPVRFSGSKSGSTATLTIAGIQAEDE<br>ADYYCQSYDDNVDGYVFGSGTQLTVLGGGSSRSSSSGGG<br>GSGGGGEVQLVETGGDLVKPGGSLRLSCVASGFTFSDYP<br>MNWVRQAPEKGLQLVGGINSGGSATYYTDAVKGRFTISR<br>DNAKNTVYLQMNSLRAEDTAMYYCATSNFQYWGQGTLV<br>TVSSESPSPPNLTSGQAGQHHHHHHGAYPYDVPDYAS |
| 45 | B10 scFv | DNA | CAGGCTGTGCTGAATCAGCCGGCCTCTGTGTCTGCAGCC<br>CTGGGGCAGAGGGTCACCATCTCCTGTAACACCAACAT<br>CGGCAGTCCTTATGATGTACAATGGTACCAGCAGCTCCC<br>AGGAAAGTCCCCTAAAACTATCATTTATGGTAATAGCA<br>ATCGACCCTCGGGGGTCCCGGTTCGATTCTCTGGCTCCA<br>AGTCAGGCAGCACAGCCACCCTGACCATCGCTGGGATC<br>CAGGCTGAGGATGAGGCTGATTATTACTGCCAGTCCTAT<br>GATGACAACGTCGATGGTTACGTGTTCGGCTCAGGGAC<br>CCAACTGACCGTCCTTGGCGGTGGTTCCTCTAGATCTTC<br>CTCCTCTGGTGGCGGTGGCTCGGGCGGTGGTGGGGAGG<br>TGCAGCTGGTGGAGACTGGGGGAGATCTGGTGAAGCCT<br>GGGGGGATCCCTGAGACTCTCTTGTGTGGCCTCTGGATTC<br>ACCTTCAGTGACTACCCCATGAACTGGGTCCGCCAGGCT<br>CCTGAGAAGGGGCTGCAGTTGGTCGGTGGTATTAACAG<br>CGGTGGAAGTGCTACATACTACACAGACGCTGTGAAGG<br>GCCGATTCACCATCTCCAGAGACAACGCCAAGAACACA<br>GTGTATCTGCAGATGAACAGCCTGAGAGCCGAGGACAC<br>GGCCATGTATTACTGTGCAACGTCTAATTTTCAGTACTG<br>GGGCCAGGGAACCCTGGTCACCGTCTCCTCAGAGAGTC<br>CATCCCCTCCAAACCTCACTAGTGGCCAGGCCGGCCAG<br>CACCATCACCATCACCATGGCGCATACCCGTACGACGTT<br>CCGGACTACGCTTCT |
| 46 | B10 heavy<br>chain full-<br>length cIgG1 | Protein | MYRMQLLSCIALSLALVTNSEVQLVETGGDLVKPGGSLRL<br>SCVASGFTFSDYPMNWVRQAPEKGLQLVGGINSGGSATY<br>YTDAVKGRFTISRDNAKNTVYLQMNSLRAEDTAMYYCAT<br>SNFQYWGQGTLVTVSSASTTAPSVFPLAPSCGSTSGSTVAL<br>ACLVSGYFPEPVTVSWNSGSLTSGVHTFPSVLQSSGLYSLS<br>SMVTVPSSRWPSETFTCNVVHPASNTKVDKPVFNECRCTD<br>TPPCPVPEPLGGPSVLIFPPKPKDILRITRTPEVTCVVLDLGR<br>EDPEVQISWFVDGKEVHTAKTQSREQQFNGTYRVVSVLPI<br>EHQDWLTGKEFKCRVNHIDLPSPIERTISKARGRAHKPSVY<br>VLPPSPKELSSSDTVSVTCLIKDFYPPDIDVEWQSNGQQEP<br>ERKHRMTPPQLDEDGSYFLYSKLSVDKSRWQQGDPFTCA<br>VMHETLQNHYTDLSLSHSPGK |
| 47 | B10 heavy<br>chain full-<br>length cIgG1 | DNA | ATGTACAGGATGCAACTCCTGTCTTGCATTGCACTAAGT<br>CTTTGCACTTGTCACGAATTCGGAGGTGCAGCTGGTGGA<br>GACTGGGGGAGATCTGGTGAAGCCTGGGGGATCCCTGA<br>GACTCTCTTGTGTGGCCTCTGGATTCACCTTCAGTGACT<br>ACCCCATGAACTGGGTCCGCCAGGCTCCTGAGAAGGGG<br>CTGCAGTTGGTCGGTGGTATTAACAGCGGTGGAAGTGC<br>TACATACTACACAGACGCTGTGAAGGGCCGATTCACCA<br>TCTCCAGAGACAACGCCAAGAACACAGTGTATCTGCAG<br>ATGAACAGCCTGAGAGCCGAGGACACGGCCATGTATTA<br>CTGTGCAACGTCTAATTTTCAGTACTGGGGCCAGGGAA<br>CCCTGGTCACCGTCTCCTCAGCTAGCACCACGGCCCCCT<br>CGGTTTTCCCACTGGCCCCAGCTGCGGGTCCACTTCCG<br>GCTCCACGGTGGCCCTGGCCTGCCTGGTGTCAGGCTACT<br>TCCCCGAGCCTGTAACTGTGTCCTGGAACTCCGGCTCCT<br>TGACCAGCGGTGTGCACACCTTCCCGTCCGTCCTGCAGT<br>CCTCAGGGCTCTACTCCCTCAGCAGCATGGTGACAGTGC<br>CCTCCAGCAGATGGCCCAGTGAGACCTTCACCTGCAAC<br>GTGGTCCACCCGGCCAGCAACACTAAAGTAGACAAGCC<br>AGTGTTCAATGAATGCAGATGCACTGATACACCCCCAT<br>GCCCAGTCCCTGAACCTCTGGGAGGGCCTTCGGTCCTCA<br>TCTTTCCCCCGAAACCCAAGGACATCCTCAGGATTACCC<br>GAACACCCGAGGTCACCTGTGTGGTGTTAGATCTGGGC<br>CGTGAGGACCCTGAGGTGCAGATCAGCTGGTTCGTGGA<br>TGGTAAGGAGGTGCACACAGCCAAGACGCAGTCTCGTG<br>AGCAGCAGTTCAACGGCACCTACCGTGTGGTCAGCGTC<br>CTCCCCATTGAGCACCAGGACTGGCTCACAGGGAAGGA<br>GTTCAAGTGCAGAGTCAACCACATAGACCTCCCATCTCC<br>CATCGAGAGGACCATCTCTAAGGCCAGAGGGAGGGCCC |

TABLE 1-continued

Sequences used in the invention

| SEQ ID NO: | Name | Type | Sequence |
|---|---|---|---|
| | | | ATAAGCCCAGTGTGTATGTCCTGCCACCATCCCCAAAG<br>GAGTTGTCATCCAGTGACACAGTCAGCGTCACCTGCCTG<br>ATAAAAGACTTCTACCCACCTGACATTGATGTGGAGTG<br>GCAGAGCAATGGACAGCAGGAGCCTGAGAGGAAGCAC<br>CGCATGACCCCGCCCCAGCTGGACGAGGACGGGTCCTA<br>CTTCCTGTACAGCAAGCTCTCTGTGGACAAGAGCCGCTG<br>GCAGCAGGGAGACCCCTTCACATGTGCGGTGATGCATG<br>AAACTCTACAGAACCACTACACAGATCTATCCCTCTCCC<br>ATTCTCCGGGTAAA |
| 48 | B10 lambda light chain full-length | Protein | MYRMQLLSCIALSLALVTNSQAVLNQPASVSAALGQRVTI<br>SCNTNIGSPYDVQWYQQLPGKSPKTIIYGNSNRPSGVPVRF<br>SGSKSGSTATLTIAGIQAEDEADYYCQSYDDNVDGYVFGS<br>GTQLTVLGQPKASPSVTLFPPSSEELGANKATLVCLISDFY<br>PSGVTVAWKADGSPITQGVETTKPSKQSNNKYAASSYLSL<br>TPDKWKSHSSFSCLVTHEGSTVEKKVAPAECS |
| 49 | B10 lambda light chain full-length | DNA | ATGTACAGGATGCAACTCCTGTCTTGCATTGCACTAAGT<br>CTTGCACTTGTCACGAATTCGCAGGCTGTGCTGAATCAG<br>CCGGGCCTCTGTGTCTGCAGCCCTGGGGCAGAGGGTCAC<br>CATCTCCTGTAACACCAACATCGGCAGTCCTTATGATGT<br>ACAATGGTACCAGCAGCTCCCAGGAAAGTCCCCTAAAA<br>CTATCATTTATGGTAATAGCAATCGACCCTCGGGGGTCC<br>CGGTTCGATTCTCTGGCTCCAAGTCAGGCAGCACAGCC<br>ACCCTGACCATCGCTGGGATCCAGGCTGAGGATGAGGC<br>TGATTATTACTGCCAGTCCTATGATGACAACGTCGATGG<br>TTACGTGTTCGGCTCAGGGACCCAACTGACCGTCCTTGG<br>TCAGCCCAAGGCCTCCCCCTCGGTCACACTCTTCCCGCC<br>CTCCTCTGAGGAGCTCGGCGCCAACAAGGCCACCCTGG<br>TGTGCCTCATCAGCGACTTCTACCCCAGCGGCGTGACGG<br>TGGCCTGGAAGGCAGACGGCAGCCCCATCACCCAGGGC<br>GTGGAGACCACCAAGCCCTCCAAGCAGAGCAACAACAA<br>GTACGCGGCCAGCAGCTACCTGAGCCTGACGCCTGACA<br>AGTGGAAATCTCACAGCAGCTTCAGCTGCCTGGTCACG<br>CACGAGGGGAGCACCGTGGAGAAGAAGGTGGCCCCCG<br>CAGAGTGCTCTT |
| 50 | Full Length Canine CTLA-4 | Protein | MAGFGFRRHGAQPDLASRTWPCTALFSLLFIPVFSKGMHV<br>AQPAVVLASSRGVASFVCEYGSSGNAAEVRVTVLRQAGS<br>QMTEVCAATYTVEDELAFLDDSTCTGTSSGNKVNLTIQGL<br>RAMDTGLYICKVELMYPPPYYVGMGNGTQIYVIDPEPCPD<br>SDFLLWILAAVSSGLFFYSFLITAVSLSKMLKKRSPLTTGV<br>YVKMPPTEPECEKQFQPYFIPIN |
| 51 | IL2 signal sequence | Protein | MYRMQLLSCIALSLALVINS |
| 52 | Canine lambda-1 light chain | Protein | GQPKASPSVTLFPPSSEELGANKATLVCLISDFYPSGVTVA<br>WKADGSPITQGVETTKPSKQSNNKYAASSYLSLTPDKWKS<br>HSSFSCLVTHEGSTVEKKVAPAECS |
| 53 | Canine cIgG1 heavy chain | Protein | ASTTAPSVFPLAPSCGSTSGSTVALACLVSGYFPEPVTVSW<br>NSGSLTSGVHTFPSVLQSSGLYSLSSMVTVPSSRWPSETFT<br>CNVVHPASNTKVDKPVFNECRCTDTPPCPVPEPLGGPSVLI<br>FPPKPKDILRITRTPEVTCVVLDLGREDPEVQISWFVDGKE<br>VHTAKTQSREQQFNGTYRVVSVLPIEHQDWLTGKEFKCR<br>VNHIDLPSPIERTISKARGRAHKPSVYVLPPSPKELSSSDTV<br>SVTCLIKDFYPPDIDVEWQSNGQQEPERKHRMTPPQLDED<br>GSYFLYSKLSVDKSRWQQGDPFTCAVMHETLQNHYTDLS<br>LSHSPGK |
| 71 | Canine cIgG2 heavy chain | Protein | ASTTAPSVFPLAPSCGSTSGSTVALACLVSGYFPEPVTVSW<br>NSGSLTSGVHTFPSVLQSSGLYSLSSMVTVPSSRWPSETFT<br>CNVAHPASKTKVDKPVPKRENGRVPRPPDCPKCPAPEML<br>GGPSVFIFPPKPKDTLLIARTPEVTCVVVDLDPEDPEVQISW<br>FVDGKQMQTAKTQPREEQFNGTYRVVSVLPIGHQDWLKG<br>KQFTCKVNNKALPSPIERTISKARGQAHQPSVYVLPPSREE<br>LSKNTVSLTCLIKDFFPPDIDVEWQSNGQQEPESKYRTTPP<br>QLDEDGSYFLYSKLSVDKSRWQRGDTFICAVMHEALHNH<br>YTQESLSHSPGK |
| 72 | Canine cIgG3 heavy chain | Protein | ASTTAPSVFPLAPSCGSQSGSTVALACLVSGYIPEPVTVSW<br>NSGSLTSGVHTFPSILQSSGLYSLSSMVTVPSSRWPSETFTC<br>NVAHPATNTKVDKPVVKECECKCNCNNCPCPGCGLLGGP<br>SVFIFPPKPKDILVTARTPTVTCVVVDLDPENPEVQISWFV<br>DSKQVQTANTQPREESNGTYRVVSVLPIGHQDWLSGKQ |

TABLE 1-continued

Sequences used in the invention

| SEQ ID NO: | Name | Type | Sequence |
|---|---|---|---|
| | | | FKCKVNNKALPSPIEEIISKTPGQAHQPNVYVLPPSRDEMS<br>KNTVTLTCLVKDFFPPEIDVEWQSNGQQEPESKYRMTPPQ<br>LDEDGSYFLYSKLSVDKSRWQRGDTFICAVMHEALHNHY<br>TQKSLSHSPGK |
| 73 | Canine cIgG4 heavy chain | Protein | ASTTAPSVFPLAPSCGSTSGSTVALACLVSGYFPEPVTVSW<br>NSGSLTSGVHTFPSVLQSSGLYSLSSMVTVPSSRWPSETFT<br>CNVVHPASNTKVDKPVPKESTCKCISPCPVPESLGGPSVFIF<br>PPKPKDILRITRTPEITCVVLDLGREDPEVQISWFVDGKEVH<br>TAKTQPREQQFNSTYRVVSVLPIEHQDWLTGKEFKCRVNH<br>IGLPSPIERTISKARGQAHQPSVYVLPPSPKELSSSDTVTLTC<br>LIKDFFPPEIDVEWQSNGQPEPESKYHTTAPQLDEDGSYFL<br>YSKLSVDKSRWQQGDPFTCAVMHEALQNHYTDLSLSHSP<br>GK |
| 74 | A1 VH Protein | Protein | EVQLVESGGDLVKPAGSLRLSCVASGFSFSSYAMNWVRQ<br>APGKGLQWIAGINSGGSSTSHIDAIKGRFTISRDNAKNTLY<br>LQMNSLRAEDTAVYYCAISNWAYWGQGTLVTVSS |
| 75 | A1 VH DNA | DNA | GAGGTGCAGCTGGTGGAGTCTGGGGGAGACCTGGTGAA<br>GCCTGCAGGGTCCCTGAGATTGTCCTGTGTGGCCTCTGG<br>ATTCTCCTTCAGCAGTTATGCCATGAACTGGGTCCGCCA<br>GGCTCCTGGGAAGGGGCTGCAGTGGATCGCAGGTATTA<br>ATAGCGGTGGAAGTAGTACAAGTCATATAGACGCTATA<br>AAGGGCCGCTTCACCATCTCCAGAGACAACGCCAAGAA<br>CACACTGTATTTACAGATGAATAGCCTGAGAGCCGAGG<br>ACACGGCCGTGTATTACTGTGCGATTAGTAATTGGGCCT<br>ACTGGGGCCAGGGAACCCTGGTCACCGTCTCCTCA |
| 76 | A1 scFv Protein | Protein | QAVLNQPASVSGSLGQRVTISCTGSSSDIGKSYVAWYQQL<br>PGTGPRTLINVDGNRASGVPDRFSVSRSGNTATLTISGLQA<br>EDEADYHCSSWDWSLHTYVFGSGTQLTILGGGSSRSSSSG<br>GGGSGGGGEVQLVESGGDLVKPAGSLRLSCVASGFSFSSY<br>AMNWVRQAPGKGLQWIAGINSGGSSTSHIDAIKGRFTISR<br>DNAKNTLYLQMNSLRAEDTAVYYCAISNWAYWGQGTLV<br>TVSSESPSPPNLTSGQAGQHHHHHGAYPYDVPDYAS |
| 77 | A1 scFv DNA | DNA | CAGGCTGTGCTGAATCAGCCGGCCTCAGTGTCCGGGTC<br>CCTGGGCCAGAGGGTCACCATCTCCTGCACTGGAAGCA<br>GCTCCGACATCGGTAAAAGTTATGTGGCCTGGTACCAG<br>CAGCTCCCGGGAACAGGCCCCAGAACCCTCATCAATGT<br>TGATGGTAACCGAGCCTCAGGGGTCCCCGATCGATTCTC<br>TGTCTCCAGGTCAGGCAACACAGCCACCCTGACCATCTC<br>CGGGCTCCAGGCTGAGGATGAGGCTGATTATCACTGCT<br>CATCCTGGGACTGGAGTCTCCATACTTACGTGTTCGGCT<br>CAGGGACCCAGCTGACCATCCTCGGTGGTGGTTCCTCTA<br>GATCTTCCTCCTCTGGTGGCGGTGGCTCGGGCGGTGGTG<br>GGGAGGTGCAGCTGGTGGAGTCTGGGGGAGACCTGGTG<br>AAGCCTGCAGGGTCCCTGAGATTGTCCTGTGTGGCCTCT<br>GGATTCTCCTTCAGCAGTTATGCCATGAACTGGGTCCGC<br>CAGGCTCCTGGGAAGGGGCTGCAGTGGATCGCAGGTAT<br>TAATAGCGGTGGAAGTAGTACAAGTCATATAGACGCTA<br>TAAAGGGCCGCTTCACCATCTCCAGAGACAACGCCAAG<br>AACACACTGTATTTACAGATGAATAGCCTGAGAGCCGA<br>GGACACGGCCGTGTATTACTGTGCGATTAGTAATTGGG<br>CCTACTGGGGCCAGGGAACCCTGGTCACCGTCTCCTCA<br>GAGAGTCCATCCCCTCCCAACCTCACTAGTGGCCAGGC<br>CGGCCAGCACCATCACCATCACCATGGCGCATACCCGT<br>ACGACGTTCCGGACTACGCTTCTTAGGAGGGTGGTGGC<br>TCTGAGGGTGGCGGTTCTGAGGGTGGCGGCTCTGAGGG<br>AGGCGGTTCCGGTGGTGGCTCTGGTTCCGGTGATTTTGA<br>TTATGAAAAGATGGCAAACGCTAATAAGGGGCTATGAC<br>CGAAAATGCCGATGAAAACGTGCTACAGTCTGACGC |

Nucleic Acids and Expression Vectors

The present disclosure provides an isolated nucleic acid encoding a polypeptide. The nucleic acid of the present disclosure may comprise a polynucleotide sequence encoding any one of the binding polypeptides, scFv, or antibodies disclosed herein.

One aspect of the invention includes an isolated nucleic acid encoding a binding polypeptide comprising an antigen-binding domain that specifically binds an epitope of canine cytotoxic T lymphocyte associated protein 4 (CTLA-4).

In certain embodiments, the nucleic acid comprises an antigen binding domain comprising a heavy chain variable region that comprises three heavy chain complementarity determining regions (HCDRs) and a light chain variable region that comprises three light chain complementarity determining regions (LCDRs). HCDR1 comprises the amino acid sequences (SEQ ID NOs: 1, 21, or 37), and/or HCDR2 comprises the amino acid sequences (SEQ ID NOs: 2, 22, or 38), and/or HCDR3 comprises the amino acid sequences (SEQ ID NO: 3, 23, or 39) and/or LCDR1 comprises the amino acid sequences (SEQ ID NOs: 4, 24, or 40), and/or LCDR2 comprises the amino acid sequences (SEQ ID NO: 5, 25, or 41), and/or LCDR3 comprises the amino acid sequences (SEQ ID NO: 6, 26, or 42).

In certain embodiments, the binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or a fragment thereof.

In certain embodiments, the heavy chain variable region is encoded by a nucleic acid comprising a polynucleotide sequence having at least 80%, 85%, 90%, 95%, 96%, 96%, 97%, 98%, 99% identity to SEQ ID NOs: 8, 28, and 44. In certain embodiments, the heavy chain variable region is encoded by a nucleic acid comprising the polynucleotide sequence set forth in SEQ ID NOs: 8, 28, and 44. In certain embodiments, the heavy chain variable region is encoded by a nucleic acid consisting of the polynucleotide sequence set forth in SEQ ID NO: 8, 28, and 44.

In certain embodiments, the light chain variable region is encoded by a nucleic acid comprising a polynucleotide sequence having at least 80%, 85%, 90%, 95%, 96%, 96%, 97%, 98%, 99% identity to the amino acid sequence of the light chain variable region set forth in SEQ ID NOs: 10, 30, and 46. In certain embodiments, the light chain variable region is encoded by a nucleic acid comprising the polynucleotide sequence set forth in SEQ ID NOs: 10, 30, and 46. In certain embodiments, the light chain variable region is encoded by a nucleic acid consisting of a polynucleotide sequence set forth in SEQ ID NOs: 10, 30, and 46.

Also provided is an isolated nucleic acid encoding a binding polypeptide comprising a heavy chain variable region encoded by a nucleic acid sequence comprising the polynucleotide sequence set forth in SEQ ID NO: 8, and a light chain variable region encoded by a nucleic acid sequence comprising the polynucleotide sequence set forth in SEQ ID NO: 10.

Also provided is an isolated nucleic acid encoding a single-chain variable fragment (scFv) comprising a heavy chain variable region that comprises three heavy chain complementarity determining regions (HCDRs) and a light chain variable region that comprises three light chain complementarity determining regions (LCDRs). HCDR1 comprises the amino acid sequence (SEQ ID NOs: 1, 20, and 35), and/or HCDR2 comprises the amino acid sequence (SEQ ID NO: 2, 22, or 38), and/or HCDR3 comprises the amino acid sequence (SEQ ID NO: 3, 22, and 37), and/or LCDR1 comprises the amino acid sequence (SEQ ID NO: 4, 24, or 40, and/or LCDR2 comprises the amino acid sequence (SEQ ID NO: 5, 25, or 41), and/or LCDR3 comprises the amino acid sequence (SEQ ID NO: 6, 26, or 42).

Also provided is an isolated nucleic acid encoding a single-chain variable fragment (scFv) comprising a heavy chain variable region comprising a nucleotide sequence set forth in SEQ ID NO: 8; and/or a light chain variable region comprising a nucleotide sequence set forth in SEQ ID NO: 10. The heavy chain variable region and the light chain variable region are separated by a linker. In certain embodiments, the linker comprises the amino acid sequence set forth in SEQ ID NO: 72.

Also provided is an isolated nucleic acid encoding a single-chain variable fragment (scFv) comprising a polynucleotide sequence set forth in SEQ ID NOs: 30, 45, or 77. Also provided is an isolated nucleic acid encoding a single-chain variable fragment (scFv) consisting of a polynucleotide sequence set forth in SEQ ID NOs: 30, 45, or 77.

Also provided is an isolated nucleic acid encoding a full-length antibody comprising a heavy chain polynucleotide sequence set forth in SEQ ID NOs: 12, 14, 16, 18, 34, and 50 and a light chain polynucleotide sequence set forth in SEQ ID NOs: 20, 36, and 52. Also provided is an isolated nucleic acid encoding a full-length antibody consisting of a heavy chain polynucleotide sequence set forth in SEQ ID NOs: 12, 14, 16, 18, 34, and 50 and a light chain polynucleotide sequence set forth in SEQ ID NOs: 20, 36, and 52.

Tolerable variations of the nucleic acid sequences will be known to those of skill in the art. For example, in some embodiments the nucleic acid comprises a nucleotide sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the nucleotide sequences set forth in SEQ ID NO: 8, 10, 12, 14, 16, 18, 20, 28, 30, 32, 34, 36, 44, 46, 48, 50, and 52.

In certain embodiments, a nucleic acid of the present disclosure comprises a first polynucleotide sequence and a second polynucleotide sequence. The first and second polynucleotide sequence may be separated by a linker. For example, in certain embodiments the heavy chain variable region and the light chain variable region of an scFv are separated by a linker. In certain embodiments, the linker comprises the amino acid sequence set forth in SEQ ID NO: 72. In certain embodiments, the nucleic acid comprises from 5' to 3' the first polynucleotide sequence, the linker, and the second polynucleotide sequence. In certain embodiments, the nucleic acid comprises from 5' to 3' the second polynucleotide sequence, the linker, and the first polynucleotide sequence.

Another aspect of the invention provides a vector comprising any one of the isolated nucleic acids disclosed herein. In certain embodiments, the vector is selected from the group consisting of a DNA vector, an RNA vector, a plasmid, a lentiviral vector, an adenoviral vector, an adeno-associated viral vector, and a retroviral vector. In certain embodiments, the vector is an expression vector.

Also provided is a host cell comprising any of the vectors or nucleic acids disclosed herein. The host cell may be of eukaryotic, prokaryotic, mammalian, or bacterial origin. A method of producing a binding polypeptide or scFv that binds to CTLA-4 is also provided herein, wherein the method comprises culturing the host cell.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid is in operable linkage with a promoter. In certain embodiments, the promoter is a phosphoglycerate kinase-1 (PGK) promoter.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank® genetic sequence database Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the nucleic acid into a host cell. Accordingly, an expression vector (e.g., a lentiviral vector) of the present invention may comprise a nucleic acid encoding a polypeptide. In some embodiments, the expression vector (e.g., lentiviral vector) will comprise additional elements that will aid in the functional expression of the polypeptide encoded therein. In some embodiments, an expression vector comprising a nucleic acid encoding for a polypeptide further comprises a mammalian promoter. In one embodiment, the vector further comprises an elongation-factor-1-alpha promoter (EF-1α promoter). Use of an EF-1α promoter may increase the efficiency in expression of downstream transgenes. Physiologic promoters (e.g., an EF-1α promoter) may be less likely to induce integration mediated genotoxicity and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a polypeptide of the present disclosure. Methods for introducing RNA into a host cell are known in the art. See, e.g., Zhao et al. Cancer Res. (2010) 15: 9053. Introducing RNA comprising a nucleotide sequence encoding a polypeptide of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a polypeptide of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In some embodiments, a nucleic acid of the present disclosure is provided for the production of a polypeptide as described herein, e.g., in a host cell. In some embodiments, a nucleic acid of the present disclosure provides for amplification of the polypeptide-encoding nucleic acid.

Methods of Treatment

The antibodies, binding polypeptides, and scFvs described herein may be included in a composition for treating a disease or condition in a subject in need thereof. The composition may include a pharmaceutical composition and further include a pharmaceutically acceptable carrier. A therapeutically effective amount of the pharmaceutical composition may be administered to the subject.

In one aspect, the invention provides a method for treating a cancer in a subject in need thereof. The method comprises administering to the subject an isolated binding polypeptide comprising a heavy chain variable region comprising an amino acid sequence at least 80%, 85%, 90%, 95%, 96%, 97%, 98%, 99%, or 100% identical to SEQ ID NOs: 6, 25, 40, or 74 and a light chain variable region comprising an amino acid sequence at least 80%, 85%, 90%, 95%, 96%, 97%, 98%, 99%, or 100% identical to SEQ ID NOs: 8, 27, or 42.

In certain embodiments, the cancer is associated with cytotoxic T lymphocyte associated protein 4 (CTLA-4)-expressing cells. In certain embodiments, the CTLA-4-expressing cell is a cancer-associated cell. In certain embodiments, the cancer-associated cell is a T lymphocyte. In certain embodiments, the CTLA-4-expressing cancer-associated cell is a CTLA-4-expressing T lymphocyte.

In certain embodiments, the binding polypeptide specifically binds to cytotoxic T lymphocyte associated protein 4 (CTLA-4). In certain embodiments, the binding polypeptide comprises an antibody or an antigen-binding fragment thereof. In certain embodiments, the antigen-binding fragment is selected from the group consisting of a Fab, a single-chain variable fragment (scFv), or a single-domain antibody. In certain embodiments, the antibody is a full-length antibody. In certain embodiments, the antibody or antigen-binding fragment is a humanized antibody or an antigen-binding fragment thereof.

Compositions of the invention can be administered in dosages and routes and at times to be determined in appropriate pre-clinical and clinical experimentation and trials. Compositions may be administered multiple times at dosages within these ranges. Administration of the compositions may be combined with other methods useful to treat the desired disease or condition as determined by those of skill in the art.

Pharmaceutical Compositions and Formulations

Also provided are pharmaceutical composition comprising any one of the binding polypeptides, scFvs, antibodies, or the antigen-binding fragments disclosed herein. Among the compositions are pharmaceutical compositions and formulations for administration, such as for treatment of a disease or disorder. Also provided are therapeutic methods for administering the pharmaceutical compositions to subjects, e.g., patients.

The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects the choice of carrier is determined in part by the particular composition and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone;

amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the composition, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the composition in an amount effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the composition, by multiple bolus administrations of the composition, or by continuous infusion administration of the composition.

Formulations include those for oral, intravenous, intraperitoneal, subcutaneous, pulmonary, transdermal, intramuscular, intranasal, buccal, sublingual, or suppository administration. In some embodiments, the composition is administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made, and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples, therefore, specifically point out the preferred embodiments of the present invention and are not to be construed as limiting in any way the remainder of the disclosure.

The materials and methods used in the experimental examples are now described.

Cells and Cell Lines. Peripheral blood mononuclear cells (PBMCs) were obtained from heparinized healthy donor dog blood or blood from a dog with T cell lymphoma (Treg staining), by discontinuous density centrifugation over Ficoll-Paque® PLUS (GE Healthcare, Chicago, IL). For feline cells, residual heparinized blood left over from clinical hematological assessment of 2 cats with hematological malignancies was first subject to ACK lysis (ThermoFisher Scientific, Waltham, MA) to remove red blood cells. Cells were washed twice in complete (c)RPMI media (RPMI 1640 containing 2 mM L-Glutamine (Mediatech, Manassas, VA), 10% heat-inactivated fetal bovine serum (Atlanta Biologicals, Flowery Branch, Georgia), 10 mM HEPES (Gibco, Grand Island, NY), and 100 U/ml penicillin and 100 µg/ml streptomycin (Gibco) prior to use. Where indicated negatively selected canine T cells were used. PBMCs were washed in (c)RPMI, labeled with mouse anti-dog CD11b (Clone CA16.3E10), CD11c (Clone CA11.6A1), mouse anti-human CD14 (Clone TuK4), and mouse anti-Dog CD21 (Clone CA2.1D6) all from ABD Serotec/Biorad followed by goat anti-mouse IgG Microbeads (Miltenyi Biotec, Bergisch Gladbach, Germany). T cells were negatively selected using MACS® LS separation columns (Miltenyi) as described by the manufacturer. T cell purity was determined by CD5 labeling and flow cytometric analysis. The human tumor cell lines (K562 and 293T cells) were grown in RPMI-1640 supplemented with HEPES, 1 mM sodium pyruvate (Mediatech), glutamine and penicillin and streptomycin (Thermo Fisher Scientific) supplemented with 10% fetal bovine serum (cRPMI).

Recombinant protein production. Total RNA was extracted from canine PBMCs cells using the RNeasy® Plus Mini Kit (Qiagen, Valencia, CA). Reverse transcription was performed using random hexamers and Superscript™ III reverse transcriptase as per the manufacturer's instructions (Life Technologies) followed by a RNAse H digestion to remove any remaining RNA. Primers to amplify the extracellular, N-terminal domain of canine CTLA-4 (NCBI Reference Sequence: NM_001003106.1) were designed using Primer3 software (primer3.org). Primer sequences were as follows:

```
cCTLA-4 Forward:
                                        (SEQ ID NO: 54)
5'-CACGAACTCGAGACCATGGCTGGCTTTGGATTCCGGAG-3', cCTLA-4 Reverse:
                                        (SEQ ID NO: 55)
5'-ATGCATTCACTCGTGCCACTCGATCTTCTGGGCCTCGAAGATGT

CGTTCAGGCCGTGATGGTGATGGTGATGGCTTCCGCCGCTTCCGCCG

AAGTCAGAATCT-3'
```

The 3' primer was designed to include a flexible linker, a histidine tag and an Avi (biotinylation) tag. Primers were synthesized by Sigma-Aldrich (St. Louis, MO). A conventional PCR using Q5 Hot Start High Fidelity Polymerase with the following thermal cycling program was used: 98° C. for 3 min; 30 cycles of 98° C. for 15 s, 65° C. for 30 s, and 72° C. for 1 min; 72° C. for 2 min and cooling to 4° C.

The expected band size for the amplified extracellular domain (ECD) of cCTLA-4 is 590 bp. The cCTLA-4 ECD amplicon was cloned into the expression plasmid pFUSE (Invivogen, San Diego, CA) containing an HA tag. cCTLA-4 ECD nucleotide sequence was verified by DNA sequence analysis. pFUSE expression plasmid containing cCTLA-4 ECD was transfected into 293T cells using Lipofectamine™ 2000 (Thermo Fisher Scientific) according to the manufacturer's directions with the amount of Lipofectamine™ used and the time of harvest investigated for maximal protein expression. CTLA-4 polypeptides were harvested from cell culture media by binding to Ni-NTA resin (Qiagen, Hilden, Germany) on a rotator for 2 h. Centrifuged resin pellets were extensively washed in high salt buffer containing 50 mM Tris-HCl, 300 mM NaCl, 10 mM imidazole, pH 8.0, and low salt buffer containing 50 mM Tris-HCl, 150 mM NaCl, 10 mM imidazole, pH 8.0. cCTLA-4 ECD protein was eluted from the Ni-NTA resin with elution buffer containing 50 mM Tris-HCl, 150 mM NaCl, 300 mM imidazole, pH 8.0. The buffer was exchanged with 1×PBS and cCTLA-4 ECD protein was concentrated in Amicon ultrafiltration units (MilliporeSigma, Burlington, MA). Protein production was evaluated using SDS-PAGE and Coomassie Blue staining of the gels and quantified by Image Lab 6.0 software (Bio-Rad, Hercules, CA) using a BSA standard.

Biotinylation of cCTLA-4 protein and validation of reaction product. Approximately 0.8 mg of recombinant cCTLA-4 ECD protein (referred to as cCTLA-4 from here on) was biotinylated in preparation for binding to a streptavidin (SA)-coated plate and subsequent scFv library panning. The Avi tag serves as the biotinylation recognition site for BirA biotin-protein ligase. cCTLA-4 was biotinylated using the BirA biotin-protein ligase standard reaction kit (Avidity, Aurora, CO) according to manufacturer's instructions. To confirm a high degree of cCTLA-4 biotinylation, 0, 2, 4 and 8 ug SA were added and samples were evaluated by SDS-PAGE. Migration of biotinylated cCTLA-4 plus SA was retarded compared to unbiotinylated cCTLA-4 indicating that the biotinylation reaction was successful and essentially stoichiometric. To confirm that biotinylated cCTLA-4 protein was immunoreactive in a 96-well plate format, capture assay followed by ELISA was performed. Briefly, varying concentrations of streptavidin in PBS were coated into wells of a micro assay plate. After O/N incubation at 4° C., 5% milk PBS-Tween® was added for 1 h at RT. PBS-Tween® washes were subsequently performed and titrations of biotinylated cCTLA-4 protein were added to wells for 1 h. Following PBS-Tween® washes, anti-canine CTLA-4 rabbit polyclonal antibody (Sino Biologicals, Chesterbrook, PA) was added at two different dilutions for 2 h at RT. Detection was with anti-canine (H and L) chain AP conjugated IgG secondary antibody (Jackson Immunoresearch, West Grove, PA) at 1/5000 dilution for 1 h at RT. Following TBS-Tween® washes, colorimetric AP substrate was added and the plate was read at 1h at an of absorbance 650. The result indicated that an absence of signal was seen in wells with no added streptavidin and that the presence of signal required increasing amounts of plated streptavidin capture protein (data not shown). 30 ug/ml streptavidin was used for immobilization of biotinylated cCTLA-4 protein for phage library screening and ELISA analysis.

Generation of a canine (TLA-4 expressing target cell line. To generate a cCTLA-4 expressing target cell line for antibody validation, the full length cCTLA-4 (NCBI Reference Sequence: NM_001003106.1) was amplified from cDNA derived from canine PBMCs by RT-PCR as described above using the following primers (cCTLA-4 Forward: 5'-acgctGAATTCatggctggctttggattccggaggcat-3'(SEQ ID NO: 56), cCTLA-4 Reverse: 5'-acagtGTCGACtcaattgatgggaataaaataa-3' (SEQ ID NO: 57)). The resulting 1856 bp amplicon was cloned into the pMX-puromycin retroviral expression vector (Cell Biolabs, Inc. San Diego CA). Retrovirus was generated and used to stably transduce the human erythroleukemic K562 cell line, previously edited using CRISPR/Cas9 to remove FcγRII (KTδ32) to reduce non-specific binding of mAb in flow cytometric assays. Transduced cells were selected in 2.5 ug/ml of puromycin dihydrochloride (Sigma, St. Louis, MO) to yield KTδ32.cCTLA-4. Expression of the cCTLA-4 transgene was confirmed in these cells by RT-PCR, using the primers synthesized to amplify cCTLA-4. Untransduced KTδ32 cells were used as negative control target cells.

Canine scFv phage display panning. For each round of panning, wells of a 96-well Costar 3490 ½ area plastic microplate were coated with 50 ul of 20 ug/ml streptavidin (SA) at 4° C. overnight (24 wells in panning 1, 16 wells in panning 2, 8 wells in pannings 3 and 4). Plates were washed in PBS, wells were blocked with 2% milk in PBS (MPBS), and incubated at 37° C. for 1 hr. Biotinylated AviTag™-cCTLA-4 (10 pmoles) was added to each streptavidin-coated well and captured by the plate-bound SA. After a 1-hr incubation at 37° C., plates were washed with PBS to remove free CTLA-4. Equal aliquots of μκ, μλ, γκ, and γλ canine scFv phage display libraries mixed together, blocked for 1 hr at RT in 2% milk/PBS, and 50 ul added to each CTLA-4-coated well. Panning was performed as previously described with other libraries and targets (e.g., in Barbas et al. Phage Display: A Laboratory Manual, Cold Spring Harbor Press, 2001), where after a 2 hour incubation at 37° C., unbound phage was washed away 5 times during the first panning and 10 times during subsequent panning rounds with PBS supplemented with 0.5% Tween® 20 (PBST). Each wash was performed with a 5-min incubation of wash buffer in wells to select for binders with longer off-rates. To avoid capturing scFv-phage specific for SA or the biotinylated AviTag™ on cCTLA-4, prior to each round of positive selection, phage was negatively selected against wells coated with SA and pre-loaded with an irrelevant biotinylated AviTag™ protein (in this case human biotinylated AviTag™-CD3ε protein, AcroBiosystems, Newark, DE). Using this 2-step negative/positive selection approach, the IgM/IgG/κ/λ canine scFv phage display library underwent 4 rounds of selection using acid elution of bound phage as described (Barbas et al., above).

scFv phage ELISA. For ELISAs to detect binding of phage-displayed scFvs, microplates were coated with streptavidin and biotinylated AviTag™ CTLA-4 and control antigens as for the library panning as above. To the antigen-coated plated, samples were added of polyclonal phage from the PEG-precipitated initial library (P0) and libraries obtained after each round of panning (P1 through P4) diluted 1:1000 in MPBS) or monoclonal phage prepared from randomly picked phage clones from output plates of the third round (P3) and fourth round (P4) of panning (non-PEG-precipitated diluted 1:100 in milk/PBS) were added to coated plates and incubated for 1 hour at 37° C. Plates were washed with (PBST) and a 1:5000 dilution of HRP-conjugated anti-M13 mAb (GE Healthcare, Chicago, IL) in MPBS was added. Plates were washed again and bound HRP-conjugated secondary antibody was detected with ABTS. OD was read at 405 nm after 30 min using a Molecular Devices SPECTRAmax™ 340 spectrophotometer. Plates coated with no antigen, canine CD19, streptavidin alone, and streptavidin with irrelevant human AviTag™-CD38ε were used as negative controls.

Flow cytometry. Canine PBMCs or isolated T cells, feline leucocytes and KTδ32.cCTLA-4 and KTδ32(WT) cell lines were washed twice in FACS buffer (1% heat-inactivated FBS in PBS with calcium and magnesium). Cells were blocked with 10 ug of canine IgG for 10 minutes at RT prior to cell surface labeling with 5 ug of canine scFv, or 500 ng canine monoclonal antibody (mAb). Specificity of mAb binding was evaluated in blocking experiments where 250 ng mAb was pre-incubated with 1.25 μg cCTLA-4 ECD protein for 1 hr at RT prior to incubation with target cells. Cells were washed in FACS buffer and incubated with either mAb alone or mAb pre-incubated with soluble cCTLA-4 ECD protein to block antigen-binding sites of the mAb. After washing, an APC labeled anti-HA.11 epitope tag (BioLegend, San Diego, CA) and viability dye 7-AAD (BioLegend) were added and cells were incubated for 30 mins at RT. For experiments using PBMCs, where indicated cells were also labeled with rat anti-canine CD45 (Clone YKIX716.13, BioRad, Hercules, CA), rat anti-canine CD5 mAb (Clone: YKIX 322.3 ThermoFisher Scientific) or mouse anti-feline CD5 mAb (Clone: FE1.1B11, BioRad) and/or rat anti-canine CD4 (Clone YKIX302.9 BioRad). Following cell surface labeling, cells were washed twice in FACS buffer and fixed in 1% paraformaldehyde (Thermo Fisher Scientific, Waltham, MA). Cells were washed again and resuspended in FACS buffer prior to acquisition on a FACSCanto™ II flow cytometer (BD Biosciences). Data was analyzed using FlowJo software version X (Treestar, Ashland, OR). All plots shown are gated on 7AAD negative cells. For intracellular staining of canine PBMCs or regulatory T cells, cells were surface stained where applicable, washed twice in FACS buffer and resuspended in fixation/permeabilization FOXP3/Transcription Factor Staining Buffer Set (ThermoFisher Scientific, Waltham, MA). Cells were incubated on ice for 30 mins in the dark and then washed once with permeabilization buffer. Cells were then incubated with APC-conjugated anti-mouse FoxP3 (clone: FJK-16s, ThermoFisher Scientific) or Rat IgG2a kappa isotype control APC (17-4321-81, ThermoFisher Scientific), anti-CTLA-4 mAbs (0.5 ug) or an anti-MERS antibody (0.5 ug, negative control) on ice for 30 mins. Cells were washed once with permeabilization buffer and twice with 1×FACS buffer prior to acquisition on a FACSCanto™ II flow cytometer.

Generation of soluble scFvs. Phage clones confirmed to bind cCTLA-4 by phage ELISA were used to infect TOP10 F' E. coli (Invitrogen, Carlsbad, CA) at various dilutions and plated out on LB agar plates containing 100 ug/ml carbenicillin and 1% glucose. Single colonies were used to inoculate starter culture flasks containing 20 ml LB with 50 ug/ml carbenicillin and 1% glucose. Cultures were grown shaking at 225 rpm overnight at 37° C. 10 ml saturated starter cultures were used to inoculate expression cultures containing 200 ml SB with 50 ug/ml carbenicillin and 0.1% glucose. Flasks were grown shaking at room temperature for about 5 h to an OD600 of 0.5 and then induced with 0.5 mM IPTG. Growth was O/N at RT for a total of 22-24 h post induction. Cultures were centrifuged and media was decanted from cell pellets. Cell pellets were extracted with two periplasmic extraction buffers in succession. Buffer I contained 100 mM Tris-HCl, 20% sucrose and 1 mM EDTA, pH 8.0, buffer II contained 5 mM MgCl2. Extraction was with pipettes to break up clumps and extracts were held for 20-30' on ice. After each extraction, extracts were centrifuged at 3400×g for 15 min and the two types of extracts were combined and mixed. For immobilized metal affinity chromatography purification, NaCl (300 mM) and imidazole (10 mM) were added and combined extracts were recentrifuged at 3400×g for 15 min. Supernatants were then bound to Ni-NTA agarose and scFvs were purified similarly to CTLA-4 protein as described above.

High throughput expression extracts were generated following a two-step growth protocol analogous to generation of E. coli cells for scFv purification (above). Single TOP10F' colonies resulting from infection with polyclonal phage from cCTLA-4 panning rounds were placed into 96-well round bottom cell culture plates containing LB with 50 ug/ml carbenicillin and 1% glucose. Plates were shaken O/N at 37° C. 5 ul of confluent wells was used to inoculate a second set of 96 well plates containing SB with 50 ug/ml carbenicillin, 0.1% glucose and 0.5 mM IPTG. Colonies were grown O/N at RT in a bacterial shaker. Expression extracts were generated by addition of ¼ volume of BEL buffer to wells of expression plates shaking for 1 hr at RT. BEL buffer consisted of 320 mM NaCl, 400 mM $H_3BO_3$, pH 8.0 with lysozyme added to 2 mg/ml, EDTA to 4 mM and benzonase nuclease to 12.5 units/ml final. Lysozyme and benzonase were from Sigma Aldrich. Extracts were blocked with 2.5% milk/PBS-Tween® and shaken for 30 min. Expression extracts were used directly in an anti-cCTLA-4 ELISA.

Soluble scFv ELISA. 30 ug/ml streptavidin was added to ELISA plates and incubated O/N at 4° C. Plates were subsequently blocked with 5% milk/PBS-Tween®. Titrations of biotinylated CTLA-4 were added and after washing, 0.25 ug/ml of soluble scFvs were added and bound for 2 hr at RT. For expression extract ELISA, 10-100 ul of extracts were added to ELISA plates and incubated for 2 hr at RT. Bound scFvs were detected using anti-HA mouse IgG AP conjugate (or an anti-rabbit AP conjugate for the positive polyclonal rabbit anti-canine CTLA-4 mAb control (Sino Biological) incubated for 1 hr at RT, washed and detected by an AP colorimetric substrate. Plates were read at 650 nm. In some instances, bivalent scFvs were generated from monovalent scFvs for use in ELISA and in inhibition studies. Briefly, 2.5 ug soluble scFvs were incubated with 1 ug/ml (for ELISA) or 5 ug/ml (for blocking studies) anti-HA alkaline phosphatase or anti-HA-FITC antibody (clone: HA-7, Sigma Aldrich) respectively that binds the C terminal HA molecule on each scFv for 2 hr at RT to generate bivalent scFv preparations.

ELISA based interaction assay. 0.3, 1.0 and 3.0 pmol of recombinant human CD86-Fc chimera (carrier free) or human CD80-Fc chimera (carrier free) (BioLegend, San Diego, CA) were bound to ELISA plates overnight. Wells were blocked with 5% milk/PBS 0.05% Tween® 20. Three pmol of biotinylated or unbiotinylated cCTLA-4 ECD protein in PBS/Tween® were added to the wells and shaken for 2 hr at RT. For experiments aimed at evaluating the ability of canine scFvs or canine mAbs to inhibit the interaction of cCTLA-4 ECD with plate bound CD80 and CD86, cCTLA-4 ECD was pre-incubated with scFv or mAbs at the indicated molar ratios for 1 hr at RT prior to being added to the plate and incubated on a shaker for 2 hr at RT. After washing, a streptavidin-AP conjugate (Jackson Immunoresearch, West Grove, PA) was added for 1 hr at RT. Three TBS-Tween® washes were performed and cCTLA-4 bound to CD80 or CD86 was detected using an AP colorimetric substrate (Invitrogen).

Generation of fully canine anti-CTLA-4 mAbs. Full length, bivalent IgG antibodies were generated from isolated scFvs by cloning the VH and VL chains of selected scFvs into separate expression plasmids that contained either the canine constant light kappa (CLκ) or constant light lambda (CLλ) domains or the canine constant IgG1 heavy chain domain ($IgG_A$). Canine CLλ and CLκ were cloned into pFUSE2ss (Invitrogen) to generate pFUSE2ss-CLIg-dλ3, pFUSE2ss-CLIg-dλ5 and pFUSE2ss-CLIg-dκ that can be selected using blasticidin resistance. Similarly, canine VH chains (IgG1-IgG4 also called $IgG_{A-D}$) were cloned into pFUSEss to generate pFUSEss-CHIg-dG1 (Invivogen), which can be selected in zeocin. Plasmids for cloning of the variable regions were selected based on the subtype (λ versus κ) of the isolated VL region. Adherent 293T cells were transiently co-transfected with light and heavy chain plasmids at ratio of 1.5:1, respectively using Lipofectamine™ L2000 reagent (ThermoFisher Scientific). Plate supernatants were harvested 3 days later and mAbs were purified using protein A affinity chromatography.

Complementation fixation assay. 30 ug/ml streptavidin was added to ELISA plates and incubated O/N at 4° C. Plates were subsequently blocked with 5% milk/PBS-Tween®. 200 ul/well of biotinylated cCTLA-4 was added to the plate and after one wash with PBS-T, serial dilutions of the four different subclasses (A, B, C and D) of HA-tagged canine anti-canine CTLA-4 (A1mut2) antibodies ranging from 0.03 to 10 ug/ml were added to the plate and incubated for 1 hr at RT. Plates were washed 3 times in PBS-Tween® before 1:35 dilution of normal human complement serum was added to one set of wells. Plates were incubated for 2 hr at RT. As a negative control, heat inactivated complement (HI) was added to a parallel set of wells. After incubation, wells were washed three times with PBS-Tween® and bound complement was detected with anti-human C1q IgG HRP conjugate antibody (BioRad, Hercules, CA). Plates were incubated for 1 hr at RT, washed three times in PBS-Tween® before an HRP substrate was added (R&D Systems, Minneapolis, MN) and colorimetric analysis was performed. To confirm antibody binding to the plate, the same canine antibody dilutions were used, and bound antibody was detected with an AP-conjugated anti-HA IgG (Sigma), detected using an AP substrate (InvivoGen, San Diego, CA).

In vitro stimulation assays. PBMCs from healthy donor dogs were isolated by density gradient centrifugation using Ficoll-Paque® Plus (Sigma, St. Louis, MO). Cells were washed once with PBS and RBCs were removed by ACK lysing buffer (ThermoFisher Scientific). Cells were washed once in complete IMDM media supplemented with 10% FBS, labeled with CellTrace™ Violet proliferation dye (ThermoFisher Scientific) at 0.5 uM, and incubated for 20 mins at RT. Cells were washed in complete IMDM and resuspended to $1\times10^6$ cells/ml and cultured in triplicate in 96-well, round bottom plates with Concanavalin A (Sigma-Aldrich) at 2.5 mg/ml, in the presence or absence of 10 mg/ml of anti-canine CTLA-4 mAbs or the negative anti-MERS mAb control. On day 3 of culture, supernatants were harvested and the amount of IFN-γ present in the supernatants was measured by canine IFN-γ ELISA (R&D Systems, Minneapolis, MN) according to the manufacturers' instructions. For experiments to detect cell surface expression of CTLA-4 after activation, canine PBMCs were resuspended to $1\times10^6$ cells/ml and cultured in triplicate in 96-well, round bottom plates with Concanavalin A at 2.5 mg/ml for 48 and 72 hours prior to analysis.

Surface Plasmon Resonance Binding Assays. A Biacore T200 with version 2.0 and HC30M (Xantec Bioanalytics, Duesseldorf, Germany) sensor chips were used to determine the binding affinity of anti-canine CTLA-4 antibodies to soluble cCTLA-4 ECD. Anti-CTLA-4 antibodies were immobilized on the surface of a protein A/G coated linear carboxylate SPR sensor chip. Briefly, each monoclonal anti-CTLA-4 antibody was diluted to 2.5 ug/ml in 20 mM acetate at a pH of 5.0 and injected into the experimental flow cell over 60 seconds. For B10, 440-475 RU were captured, for D5, 400-500 RU were captured and for A1mut2, 485-535 RU were captured. 10×1:2 serial dilutions of cCTLA-4 ECD ranging from 200 nM to 0 nM were prepared in duplicate in running buffer (10 mM HEPES, pH 7.4, 150 mM NaCl and 0.05% Tween® 20). The flow rate across the chip was 30 uL/min and the contact time of the cCTLA-4 ECD sample with the chip surface was 240s. Dissociation was monitored for 720s. Report points were recorded before and after each injection and the amount of antigen binding for each analysis cycle was reported in relative response units (RU). Plots of response versus antigen concentration were generated using the BIAcore Wizard program. After each injection of CTLA-4, the chip surface was regenerated with 20 mM glycine at pH 2.0 for 60 seconds after the RU for each concentration of analyte was recorded. All experiments were carried out at 25° C. Assay data was processed using Biacore Evaluation Software, version 2.0 to obtain kinetic values and reported as $k_{on}$, $k_{off}$ and $K_D$.

Example 1: Generation of Recombinant HA-Tagged Canine CTLA-4

The extracellular domain of cCTLA-4 was cloned and biotinylated for plate immobilization via streptavidin (SA) for panning and binding experiments. Successful protein production was confirmed by SDS-PAGE. SDS-PAGE analysis revealed a band of ~23 kDa, which is higher than the 16.4 kDa predicted molecular weight of the ECD alone with the difference likely due to protein glycosylation. Mass spectrometry validated the identity of the recombinant protein (data not shown). To confirm appropriate stoichiometry of biotin bound to cCTLA-4 for SA binding, increasing concentrations of SA were added to biotinylated cCTLA-4 and SDS-PAGE analysis was repeated. Following the addition of SA, biotinylated cCTLA-4 was retarded in the gel and bands were no longer identified at 23 kDa, confirming the ability of the biotinylated protein to bind to SA. To confirm that biotinylated cCTLA-4 ECD protein was immunoreactive in a 96-well plate format, a capture assay followed by ELISA was performed. The result showed that immunoreactivity of biotinylated cCTLA-4 required the presence of plate-bound SA.

Example 2: Isolation of Canine Anti-Canine CTLA-4 scFv

Figure 2:
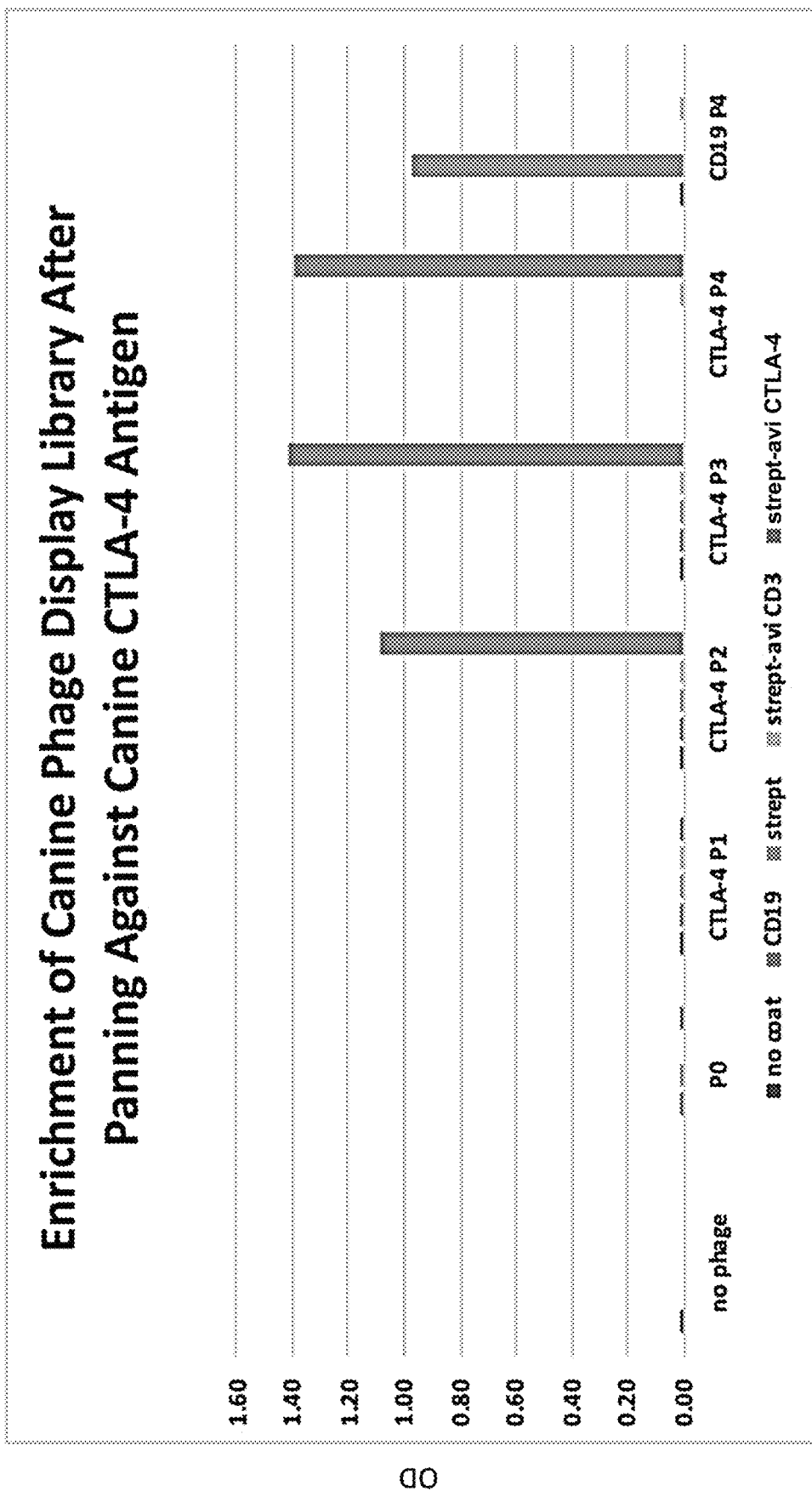
FIG. 2. Illustrates enrichment of canine phage display library after panning against canine CTLA-4 antigen. Biotinylated AviTag™-cCTLA-4 was captured on a streptavidin coated microtiter plate overnight at 4° C. Wells were washed with PBS and blocked with 2% milk in PBS (MPBS) for 1 hour at 37° C. Initial library (P0) and polyclonal libraries obtained after each round of panning (P1 through P4; 1:1000 dilution in MPBS) were added to coated plates and incubated for 1 hour at 37° C. Plates were washed with PBS supplemented with 0.5% Tween® (PBST) and bound phage was detected using a 1:5000 dilution of HRP-conjugated anti-M13 mAb (GE Healthcare) in 2% milk. Plates were washed again and bound phage were detected with ABTS. OD was read at 405 nm after 30 min using a Molecular Devices Spectra Max 340 spectrophotometer. Plates coated with no antigen, canine CD19 and human AviTag™-CD3 were used as negative controls antigens. Polyclonal phage from the 4th round of panning against canine CD19 from a parallel panning campaign was used as a positive control.

A comprehensive canine IgM/IgG/λ/κ scFv phage display library containing an estimated 40 billion independent canine scFv transformants underwent 4 rounds of solid phase selection ("panning") against biotinylated cCTLA-4. Substantial enrichment of phage for cCTLA-4 specific binders began in the second round of panning (P2) and increased through to the fourth round of panning (P4) (FIG. 1). To verify that selection of scFv-phage libraries on cCTLA-4 yielded antigen-specific scFv phage particles, polyclonal scFv phage from each round of panning was evaluated by scFv phage ELISA using cCTLA-4 as the target antigen (FIG. 2). scFv-phage captured through positive selection on cCTLA-4 reacted only with cCTLA-4 loaded wells, and not with wells coated with SA alone or with SA loaded with an irrelevant biotinylated AviTag™-coupled protein. Recombinant canine (rc)CD19 antigen served as negative control target antigen and canine scFv phage selected against CD19 (Pan 4) and rcCD19 served as a positive control. These results demonstrate that phage eluted in the second, third and fourth round of panning contained cCTLA-4 specific scFvs.

In an initial screening, 12 clones from P3 and 12 clones from P4 were randomly selected and tested for their ability to bind to cCTLA-4 by scFv phage ELISA. All 24 clones bound to cCTLA-4 with a range of affinities (FIG. 3). Nucleotide sequencing of these 24 scFv revealed 20 unique antibodies, 17 of which had lambda light chains and 3 had kappa light chains.

To prioritize unique cCTLA-4-specific scFvs for further development, soluble scFvs were first generated, purified and their ability to bind to increasing concentrations of cCTLA-4 was confirmed by ELISA. Sufficient amounts of purified, soluble scFvs were obtained for analysis of 18 out of 20 clones. 17/18 clones were tested for their ability to bind cCTLA-4 (FIG. 14). All clones bound to cCTLA-4 with a wide range of binding affinities with clone P4-8 repeatedly showing superior binding compared to the other scFvs.

Given that 20 unique scFvs were identified amongst 24 randomly selected clones, it was hypothesized that additional unique cCTLA-4 specific scFvs were likely present in P3 and P4. Therefore, a further 88 clones were randomly selected from both P3 and P4 and expression extracts containing soluble scFvs from these additional 176 clones were generated and analyzed by scFv ELISA (data not shown). Forty-one clones gave a signal of greater than 3 times background. Ten clones showing greater than 20-fold increase in binding to cCTLA-4 over background were selected and sequenced. From these, 3 more unique clones were identified from P3 (A1, B10 and C5) and 2 more new clones (D5 and G11) were identified from P4. The binding of soluble scFvs (A1, B10, D5 and G11) to cCTLA-4 was confirmed by ELISA (FIG. 4). Clone C5 could not be produced as a soluble scFv. Thus, a total of 21 unique, fully canine, soluble scFvs that bound to the extracellular domain of cCTLA-4 were available for further analysis.

Next, it was sought to determine whether any of the unique isolated cCTLA-4-specific soluble single chains were able to block the interaction between cCTLA-4 and CD80/86, a property that might bestow therapeutic potential by enhancing T cell responses in tumor-bearing patients. Firstly, an ELISA-based interaction assay centered on the ability of biotinylated cCTLA-4 to bind to commercially available human (hu) CD86-Fc and huCD80-Fc chimeric proteins was developed. Using increasing doses of huCD86-Fc or huCD80-Fc bound to a microtiter plate, cCTLA-4 was shown to bind to both huCD86-Fc and huCD80-Fc in a dose dependent manner (data not shown). Next the ability of the 18 soluble scFvs from the original group of 20 unique clones plus the 4 unique soluble scFvs (A1, B10, D5 and G11) identified from expression extracts, to inhibit cCTLA-4: huCD86 and cCTLA-4:huCD80 interactions was determined (FIGS. 5A-5B). 17/18 and 4/4 clones from the original and additional screening group respectively showed varying degrees of inhibition of cCTLA-4 binding to huCD86. 13 of the original clones that inhibited binding of cCTLA-4 to huCD86, also inhibited the higher affinity binding of cCTLA-4 to huCD80 with clones P4-8 and P3-7 showing greatest inhibition. Clones from the additional screening round that inhibited cCTLA-4 binding to huCD86 also showed comparable or greater inhibition of cCTLA-4 binding to huCD80/86 when compared to P4-8 and P3-7 (FIG. 5). In all cases, use of a higher molar ratio of scFv:cCTLA-4 resulted in greater inhibition (6:1 compared to 2:1). Greater inhibition of binding was seen when bivalent scFvs (generated by cross linking 2 scFv via an anti-HA antibody) were compared to monovalent scFvs.

Example 3: Production of Anti-CTLA-4 mAbs

One of the main characteristics that determines whether an antibody can progress along a pipeline into an effective therapeutic is its "developability." To this end, the feasibility of reformatting cCTLA-4-specific scFvs that inhibit cCTLA-4 binding to CD80/CD86 to be reformatted into full length IgG mAbs was determined. Briefly, full length, bivalent IgG antibodies were generated from isolated scFvs by cloning the VH and VL chains of selected scFvs into separate expression plasmids that contain either canine constant light kappa (CLκ) or constant light lambda (CLλ) domains or the canine constant IgG1 heavy chain domain (IgG$_A$) Canine C1λ and CLκ were cloned into pFUSE2ss (Invitrogen) to generate pFUSE2ss-CLIg-dλ3, pFUSE2ss-CLIg-dλ5 and pFUSE2ss-CLIg-dκ that can be selected for via blasticidin resistance. Similarly, canine VH chains were cloned into pFUSEss-CHIg-dG1 which was purchased from Invivogen to complete the full range of reformatting plasmids. Plasmids for cloning of the VL regions were selected based on the subtype (λ versus κ) of the isolated VL region. Adherent 293T cells were transiently co-transfected with light and heavy chain plasmids at ratio of 1.5:1, respectively using Lipofectamine™ L2000 reagent. Plate supernatants were harvested 3 days later and mAbs were purified using protein A affinity chromatography.

Based on their ability to inhibit cCTLA-4 binding to its ligands CD80 and CD86, clones A1, D5, B10, G11 and P4-8 were chosen to be reformatted into full length IgG mAbs for further functional analysis. B10 and D5 were successfully reformatted as IgG1 (IgG$_A$) however, only low levels of clone A1 could be produced and clones G11 and P4-8 could not be produced as full length canine mAbs (FIG. 6). Given the superior capability of clone A1 to bind cCTLA-4 (FIG. 7) and block cCTLA-4 interaction with CD80/86 (FIG. 8), the ability to improve the production of A1 mAb through CDR grafting experiments was investigated. Using chain swapping experiments, low productivity was localized to the VH chain of A1 (FIG. 9). Since clone B10 was readily produced, the CDR regions of A1 were grafted into the VH backbone of Clone B10. The resulting chimeric A1 VH chain transfected with the original A1 VL chain resulted in high yield production of the fully canine mAb named A1mut2. The ability of fully canine A1mut2, B10 and D5 to bind cCTLA-4 in ELISA (FIG. 11A) and inhibit interaction of cCTLA-4 with CD80/86 was confirmed (FIG. 11B). In parallel, the ability of fully canine mAbs to inhibit the binding of cCTLA-4 to canine CD80/86 was also confirmed (FIG. 11C). For these experiments, a hemagglutinin (HA) tag separated by a glycine-serine rich linker sequence was appended to the carboxyl termini of the full-length IgGs and antibodies were detected with a secondary antibody directed to the tag. This required the addition of the nucleotide sequence 5'-GGCGGAGGCTCCGGAGGCGGATCT-TACCCATACGATGTTCCAGATTACGCT-3' (SEQ ID NO: 81) which encoded the amino acid sequence NH$_3$-GGGSGGGSYPYDVPDYA-COOH (SEQ ID NO: 82). To obtain non-commercially available canine CD80 and CD86 proteins, amino acid sequences with accession numbers NP_001003147 1 and ABH87294.1, respectively, were obtained from the NCBI database. Canine CD80 and CD86 human Fc-tagged constructs were designed using corresponding human CD80-Fc and CD86-Fc constructs as guides (ACROBiosystems, Newark, Delaware; #B71-H5259 and #CD6-H5257, respectively). Canine extracellular domain sequences were fused to a triple alanine sequence followed by a modified human IgG1 Fc bearing a C to S mutation in the hinge region. Native canine CD80 and CD86 signal peptides were replaced with a murine IgG heavy chain signal sequence. gBlocks for construct sequences were ordered from IDT (Coralville, Iowa) and cloned into the pFUSE plasmid. pFUSE cCD80-hFc and cCD86-hFc plasmids were transfected into 293T cells with Lipofectamine™ 2000 and cell media was harvested 3 days later. Purification of ligand Fc fusion proteins from cell culture supernatants was performed using Protein A agarose (MilliporeSigma, Burlington, MA). Sample concentration, buffer exchange into PBS, SDS-PAGE analysis, and quantification were carried out as for the production of recombinant canine CTLA-4 protein.

Example 4: CTLA-4-Specific mAbs Bind Cell Surface Expressed CTLA-4

To determine whether the A1mut2, B10 and D5 mAbs bind to membrane-expressed cCTLA-4, KTδ32 cells were genetically modified to express cCTLA-4 (KTδ32.cCTLA-4) and used as target cells in flow cytometry experiments (FIG. 10). All clones bound to KTδ32.cCTLA-4 but not to the parent KTδ32 cells. Furthermore, pre-incubation of each mAb with soluble cCTLA-4 to block CTLA-4 binding sites abolished mAb binding indicating that membrane binding was antigen-specific. The irrelevant MERS mAb did not bind to KTδ32.cCTLA-4 further suggesting that the selected clones were binding specifically to cCTLA-4. Next, the ability of the 3 selected mAbs to bind to CTLA-4 on the surface of activated canine T cells was assessed (FIG. 15). Negligible amounts of CTLA-4 were detected on the surface of CD5$^+$CD4$^+$ and CD5$^+$CD4$^-$ cells prior to activation, however, both T cell subsets demonstrated a significant increase in CTLA-4 expression at 48 and 72 hours post activation. At each timepoint, a greater percentage of CD4 T cells expressed CTLA-4 compared with CD8 T cells (50.7% vs 29.5% at 48 hrs and 56.6% vs. 40.5% at 72 hrs respectively). Next, the surface and intracellular expression of CTLA-4 on canine CD5$^+$CD4$^+$FoxP3$^+$ regulatory T cells was determined using A1mut2 mAb. A1mut2 labelled both surface-expressed and intracellular CTLA-4 on Tregs isolated from the peripheral blood of a dog with T cell lymphoma, confirming that CTLA-4 is constitutively expressed by canine peripheral blood Tregs (FIG. 16). Finally, given that canine and feline CTLA-4 share 99% identity, feline leucocytes were labeled with A1mut2 mAb to determine antibody cross-reactivity. Feline CD5+ cells showed minimal surface staining with A1mut2 however, the antibody bound strongly to intracellular CTLA-4 (FIG. 17).

Example 5: Fully Canine Anti-CTLA-4 mAbs Demonstrate High Binding Affinity for Soluble cCTLA-4

The affinities of A1mut2, D5 and B10 for cCTLA-4 were evaluated to determine whether they may be suitable for therapeutic use (FIG. 12A-12C). Using surface plasmon resonance (SPR), the on and off rates of these 3 mAb against cCTLA-4 were determined (FIG. 21). The dissociation constant ($K_D$) of A1mut2 was in the sub-nanomolar range and demonstrated the highest binding affinity of the 3 clones. The other 2 clones displayed single digit nanomolar affinities. Thus, all 3 mAbs displayed sufficient binding affinity to cCTLA-4 to serve as candidates to evaluate as therapeutic checkpoint inhibitors. (illustrated in FIG. 13).

Example 6: Fully Canine Anti-CTLA-4 IgG2 (IgG$_B$) and IgG3 (IgG$_C$) Fix Complement Given that an increasingly recognized contribution of CTLA-4 targeted antibodies to anti-tumor immunity is their ability to deplete intratumoral regulatory T cells, the ability of A1mut2 IgG subclasses to fix complement was tested in vitro. As previously demonstrated, IgG$_B$ and IgG$_C$ effectively fixed complement whereas IgG1 (IgG$_A$) and IgG4 (IgG$_D$) did not (FIGS. 18A-18B). This result indicates that these subclasses of A1mut2 Ig have the potential to initiate complement-mediated cytotoxicity of CTLA-4$^+$ cells, an effect that is mostly confined to intratumoral Tregs that express high levels of CTLA-4.

Example 7: Clones A1mut2 Increases T Cell Proliferation and IFN-γ Production

To determine whether A1mut2 which showed the highest affinity for cCTLA-4 and greatest inhibition of cCTLA-4 binding to CD80/86 could increase T cell proliferation through its ability to block checkpoint signaling, canine PBMCs were labeled with CellTrace™ Violet proliferation dye and stimulated with Concanavalin A in the presence of either A1mut2 or the irrelevant MERS-specific mAb. Cells were harvested at 72 or 96 hr, and the responder frequency and proliferative capacity of T cells activated in the presence of A1mut2 versus MERs was determined by flow cytometry (FIG. 19). A1mut2 increased the percentage of T cells responding to the mitogen (responder frequency) and the average number of daughter cells produced per responding cell (proliferative capacity) in 8/9 dogs at 96 hours post stimulation when compared to the irrelevant MERS mAb. IFN-γ production was evaluated in the supernatants of T cells stimulated with ConA in the presence of A1mut2. T cell cultures from X/Y dogs showed an increase in IFN-γ production at 96 hrs when A1mut2 was added to the cultures (FIG. 20). Together, these results suggest that A1mut2-mediated checkpoint inhibition promotes canine T cell proliferation and IFN-γ production and further support its clinical evaluation as a mAb to enhance tumor-specific T cell priming and effector responses within the tumor microenvironment.

Example 8: Discussion

CTLA-4 blockade has proven to be a powerful strategy to promote anti-tumor immunity by inducing the expansion of Th1-like CD4 effector T cells and exhausted CD8+ T cells and eliminating intratumoral regulatory T cells. These effects have led to clinically relevant anti-tumor immunity particular in human patients with malignant melanoma, NSCLC, and renal carcinoma. However, a greater understanding of mechanisms of acquired and/or innate resistance of tumors to anti-CTLA-4 therapy, identification of biomarkers of response, optimized protocols and combination approaches to improve outcome, and understanding and reducing mechanisms related to toxicity is needed to increase overall response rate and reduce toxicity. The studies presented in the present disclosure have employed a powerful scFv phage display approach to identify multiple unique clones of fully canine scFvs that specifically bind with nanomolar and sub-nanomolar affinities to canine CTLA-4. From these clones, fully canine mAb lead candidates have been generated and further selected based on developability and in vitro functional capacity to employ in clinical trials in dogs with spontaneous cancers. The use of a fully canine anti-CTLA-4 mAb in immune competent canine cancer patients with spontaneous tumors that share similar features to their human counterparts will yield informative results for human clinical trial design.

The studies of the present disclosure have confirmed specific binding of A1mut2 to canine CTLA-4 and have demonstrated that CTLA-4 is up-regulated on the surface of CD4+ and CD8+ T cells following mitogen activation, using A1mut2 in flow cytometry. Higher CTLA-4 expression was observed in the CD4 T cell subset compared to CD8 T cells after activation, consistent with findings in human CD4 and CD8 T cells and differential kinetics of CTLA-4 up-regulation on T cell subsets in the dog, with expression on CD4+ T cells peaking earlier (48 hrs) than CD8+ T cells (>=72 hrs). Studies in human T cells demonstrate peak expression of CTLA-4 on mitogen activated total T cells occurs at 72 hrs post stimulation.

In human studies, monotherapy with ipilimumab showed minimal effects on IFN-γ production and T cell proliferation in allogeneic T:DC MLR assays and only modest increases in IL-2 production following mitogen activation of human T cells. Furthermore, response varied between individual samples tested. Although in vitro assay response in human T cells has been modest, clinical responses in a subset of human patients have been dramatic and underscore the multifactorial mechanism of action of CTLA-4 blockade and influence that patient specific factors may have on clinical response. The studies of the present disclosure also observed a significant variability in T cell responses to CTLA-4 blockade amongst mitogen activated T cells from healthy donor dogs, and moderate effects on T cell proliferation and cytokine production. Similar to results from human donors, a low level of CTLA-4 surface expression was observed on resting T cells, that, without wishing to be bound by theory, suggests use of A1mut2 in canine cancer patients will not lead to inappropriate activation of naïve T cells. Furthermore, these studies have confirmed on a protein level that CTLA-4 is present/up-regulated in regulatory T cells and may serve as a target for A1mut2-dependent complement mediated cytotoxicity. Indeed, in human patients, the higher level of CTLA-4 expression on intra-tumoral Tregs enables selective depletion following anti-CTLA-4 treatment compared to Tregs in the general circulation, leading to an increase in CD8: Treg following treatment. A1mut2 has now been engineered as IgG$_B$ which is functionally equivalent to the human IgG1 subtype (Bergeron et al. Vet Immunol Immunopath, 157:31-41, 2014), efficiently binding complement and inducing ADCC. Therefore, it is anticipated that similar effects will occur on intra-tumoral regulatory T cells in canine tumors.

Since clinical responses in canine malignancies mirror those of human patients with melanoma, renal cell carcinoma and urothelial carcinoma, it is anticipated that this therapy will improve the outcome of pet dogs suffering with similar malignancies.

Enumerated Embodiments

The following enumerated embodiments are provided, the numbering of which is not to be construed as designating levels of importance.

Embodiment 1 provides an antibody or antigen-binding fragment thereof comprising an antigen-binding domain that specifically binds to an epitope of canine cytotoxic T lymphocyte-associated protein 4 (CTLA-4), wherein the antigen-binding domain comprises:
  i. a heavy chain variable region comprising an amino acid sequence having at least 80%, 85%, 90%, 95%, 96%, 96%, 97%, 98%, 99% identity to the amino acid sequence of the heavy chain variable region set forth in SEQ ID NOs: 6, 25, 40, or 74; and
  ii. a light chain variable region comprising an amino acid sequence having at least 80%, 85%, 90%, 95%, 96%, 97%, 98%, 99% identity to the amino acid sequence set forth in SEQ ID NOs: 8, 27, or 42;
  wherein the heavy chain variable region comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  wherein the light chain variable region comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

Embodiment 2 provides the antibody or antigen-binding fragment thereof of embodiment 1, wherein the antibody or antigen-binding fragment thereof is selected from the group consisting of a full-length antibody, a Fab, and a single-chain variable fragment (scFv).

Embodiment 3 provides the antibody or antigen-binding fragment thereof of embodiment 2, wherein the antibody or antigen-binding fragment thereof is a full-length antibody.

Embodiment 4 provides the antibody or antigen-binding fragment thereof of embodiment 3, wherein the antibody is a canine antibody.

Embodiment 5 provides the antibody or antigen-binding fragment thereof of any one of embodiment 1, wherein the antigen binding domain comprises a heavy chain variable region comprising an amino acid sequence set forth in SEQ ID NOs: 6, 25, 40, or 74.

Embodiment 6 provides the antibody or antigen-binding fragment thereof of any one of embodiment 1, wherein the antigen binding domain consists of a heavy chain variable region consisting of an amino acid sequence set forth in SEQ ID NOs: 6, 25, 40, or 74.

Embodiment 7 provides the antibody or antigen-binding fragment thereof of any one of embodiments 1-4, wherein the antigen binding domain comprises a light chain variable region comprising an amino acid sequence set forth in SEQ ID NO: 8, 27, or 42.

Embodiment 8 provides the antibody or antigen-binding fragment thereof of any one of embodiments 1-4, wherein the antigen binding domain consists of a light chain variable region comprising an amino acid sequence set forth in SEQ ID NO: 8, 27, or 42.

Embodiment 9 provides an isolated antibody or antigen-binding fragment thereof comprising:
  i. a heavy chain variable region comprising the amino acid sequence set forth in SEQ ID NO: 6; and
  ii. a light chain variable region comprising the amino acid sequence set forth in SEQ ID NO: 8.

Embodiment 10 provides a single-chain variable fragment (scFv) comprising an antigen-binding domain that specifically binds to an epitope of canine cytotoxic T lymphocyte associated protein 4 (CTLA-4) comprising:
  i. a heavy chain variable region that comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  ii. a light chain variable region that comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39),
  wherein the heavy chain variable region and the light chain variable region are separated by a linker.

Embodiment 11 provides a single-chain variable fragment (scFv) comprising:
  i. a heavy chain variable region comprising the amino acid sequence set forth in SEQ ID NOs: 6, 25, 40, or 74; and
  ii. a light chain variable region comprising the amino acid sequence set forth in SEQ ID NO: 8, 27, or 42,
  wherein the heavy chain variable region and the light chain variable region are separated by a linker.

Embodiment 12 provides a single chain variable fragment (scFv) comprising an amino acid sequence set forth in SEQ ID NOs: 29, 44, or 76.

Embodiment 13 provides a single chain variable fragment (scFv) consisting of an amino acid sequence set forth in SEQ ID NOs: 29, 44, or 76.

Embodiment 14 provides a full-length antibody comprising an antigen-binding domain that specifically binds to an epitope of canine cytotoxic T lymphocyte associated protein 4 (CTLA-4), wherein the antigen-binding domain comprises:
  i. a heavy chain variable region that comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  ii. a light chain variable region that comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

Embodiment 15 provides a full-length antibody comprising:
  i. a heavy chain variable region comprising the amino acid sequence set forth in SEQ ID NOs: 6, 25, 40, or 74; and
  ii. a light chain variable region comprising the amino acid sequence set forth in SEQ ID NO: 8, 27, or 42.

Embodiment 16 provides a full-length antibody comprising a heavy chain amino acid sequence set forth in SEQ ID NOs: 10, 12, 14, 16, 31, 46, 71, 72, or 73 and a light chain amino acid sequence set forth in SEQ ID NOs: 18, 33, or 48.

Embodiment 17 provides a full-length antibody consisting of a heavy chain amino acid sequence set forth in SEQ ID NOs: 10, 12, 14, 16, 31, 46, 71, 72, or 73 and a light chain amino acid sequence set forth in SEQ ID NOs: 18, 33, or 48.

Embodiment 18 provides an isolated nucleic acid encoding the scFv or full-length antibody of any preceding embodiment.

Embodiment 19 an isolated nucleic acid encoding an antibody or antigen-binding fragment thereof comprising an antigen-binding domain that specifically binds an epitope of canine cytotoxic T lymphocyte associated protein 4 (CTLA-4), wherein the antigen-binding domain comprises:
  i. a heavy chain variable region encoded by a nucleic acid comprising a polynucleotide sequence having at least 80%, 85%, 90%, 95%, 96%, 96%, 97%, 98%, 99% identity to SEQ ID NOs: 7, 26, 41, or 75; and
  ii. a light chain variable region encoded by a nucleic acid comprising a polynucleotide sequence having at least 80%, 85%, 90%, 95%, 96%, 96%, 97%, 98%, 99% identity to the amino acid sequence of the light chain variable region set forth in SEQ ID NOs: 9, 28, or 43;
  wherein, the heavy chain variable region comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  wherein, the light chain variable region comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

Embodiment 20 provides the nucleic acid of embodiment 19, wherein the antibody or antigen-binding fragment thereof is selected from the group consisting of a full-length antibody, a Fab, and a single-chain variable fragment (scFv).

Embodiment 21 provides the nucleic acid of embodiment 20, wherein the antibody is a full-length antibody.

Embodiment 22 provides the nucleic acid of embodiment 21, wherein the antibody is a canine antibody.

Embodiment 23 provides the nucleic acid of embodiment 19, wherein the heavy chain variable region is encoded by a nucleic acid comprising the polynucleotide sequence set forth in SEQ ID NO: 7, 26, 41, or 75.

Embodiment 24 provides the nucleic acid of embodiment 19, wherein the heavy chain variable region is encoded by a nucleic acid consisting of the polynucleotide sequence set forth in SEQ ID NO: 7, 26, 41, or 75.

Embodiment 25 provides the nucleic acid of embodiment 19, wherein the light chain variable region is encoded by a nucleic acid comprising the polynucleotide sequence set forth in SEQ ID NOs: 9, 28, or 43.

Embodiment 26 provides the nucleic acid of embodiment 19, wherein the light chain variable region is encoded by a nucleic acid consisting of a polynucleotide sequence set forth in SEQ ID NOs: 9, 28, or 43.

Embodiment 27 provides an isolated nucleic acid encoding an antibody or antigen binding fragment thereof comprising:
  i. a heavy chain variable region encoded by a nucleic acid sequence comprising the polynucleotide sequence set forth in SEQ ID NOs: 7, 26, 41, or 75; and
  ii. a light chain variable region encoded by a nucleic acid sequence comprising the polynucleotide sequence set forth in SEQ ID NOs: 9, 28, or 43.

Embodiment 28 provides an isolated nucleic acid encoding a single-chain variable fragment (scFv) comprising:
  i. a heavy chain variable region that comprises three heavy chain complementarity determining regions (HCDRs), wherein HCDR1 comprises an amino acid sequence selected from the group consisting of (SEQ ID NOs: 1, 20, and 35), HCDR2 comprises an amino acid sequence selected from the group consisting of (SEQ ID NOs: 2, 21, and 36), and HCDR3 comprises an amino acid sequence selected from the group consisting of (SEQ ID NOs: 3, 22, and 37); and
  ii. a light chain variable region that comprises three light chain complementarity determining regions (LCDRs), wherein LCDR1 comprises an amino acid sequence selected from the group consisting of (SEQ ID NOs: 4, 23, and 38), a LCDR2 comprises an amino acid sequence selected from the group consisting of (VDG, GNY, and GNS), and LCDR3 comprises an amino acid sequence selected from the group consisting of (SEQ ID NOs: 5, 24, and 39).

Embodiment 29 provides an isolated nucleic acid encoding a single-chain variable fragment (scFv) comprising:
  i. a heavy chain variable region comprising a nucleotide sequence set forth in SEQ ID NOs: 7, 26, 41, or 75; and
  ii. a light chain variable region comprising a nucleotide sequence set forth in SEQ ID NOs: 9, 28, or 43,
  wherein the heavy chain variable region and the light chain variable region are separated by a linker.

Embodiment 30 provides an isolated nucleic acid encoding a single-chain variable fragment (scFv) comprising a polynucleotide sequence set forth in SEQ ID NOs: 30, 45, or 77.

Embodiment 31 provides an isolated nucleic acid encoding a single-chain variable fragment (scFv) consisting of a polynucleotide sequence set forth in SEQ ID NOs: 30, 45, or 77.

Embodiment 32 provides a vector comprising the isolated nucleic acid of any one of embodiments 19-32.

Embodiment 33 provides the vector of embodiment 32, wherein the vector is an expression vector.

Embodiment 34 provides the vector of any one of embodiments 32 and 33, wherein the vector is selected from the group consisting of a DNA vector, an RNA vector, a plasmid, a lentiviral vector, an adenoviral vector, an adeno-associated viral vector, and a retroviral vector.

Embodiment 35 provides a host cell comprising the vector of any one of embodiments 32-34.

Embodiment 36 provides the host cell of embodiment 35, wherein the host cell is of eukaryotic or prokaryotic origin.

Embodiment 37 provides the host cell of any one of embodiments 35 or 36, wherein the host cell is of mammalian origin.

Embodiment 38 provides the host cell of any one of embodiments 35 or 36, wherein the host cell is of bacterial origin.

Embodiment 39 provides a method of producing an antibody or antigen-binding fragment thereof that binds to canine cytotoxic T lymphocyte associated protein 4 (CTLA-4), the method comprising culturing the host cell of any one of embodiments 35-38.

Embodiment 40 provides a pharmaceutical composition comprising the full-length antibody or scFv of any one of embodiments 1-17 and a pharmaceutically acceptable carrier.

Embodiment 41 provides a method for treating a cancer in a subject in need thereof, comprising administering to the subject the antibody or antigen-binding fragment thereof of any one of embodiments 1-17.

Embodiment 42 provides the method of embodiment 41, wherein the cancer is associated with cytotoxic T lymphocyte associated protein 4 (CTLA-4).

Embodiment 43 provides the method of embodiment 42, wherein the CTLA-4 is expressed on a cancer-associated cell.

Embodiment 44 provides the method of embodiment 43, wherein the cancer-associated cell is a T lymphocyte.

Embodiment 45 provides the method of embodiment 41, wherein the antibody or antigen-binding fragment thereof specifically binds to canine CTLA-4.

Embodiment 46 provides the method of embodiment 41, wherein the antibody or antigen-binding fragment thereof is selected from the group consisting of a full-length antibody, a Fab, and a single-chain variable fragment (scFv).

Embodiment 47 provides the method of embodiment 46, wherein the antibody or antigen-binding fragment thereof is a full-length antibody.

Embodiment 48 provides the method of embodiment 47, wherein the antibody is a caninized antibody.

Embodiment 49 provides the method of embodiment 41, wherein the subject is canine.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antibody or antigen-binding fragment thereof comprising an antigen-binding domain that specifically binds to an epitope of canine cytotoxic T lymphocyte-associated protein 4 (CTLA-4), wherein the antigen-binding domain comprises:
    (i) a heavy chain variable region comprising an amino acid sequence having at least 80% identity to the amino acid sequence of the heavy chain variable region set forth in SEQ ID NO: 6; and
    (ii) a light chain variable region comprising an amino acid sequence having at least 80% identity to the amino acid sequence set forth in SEQ ID NO: 8;
    wherein the heavy chain variable region comprises three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in of SEQ ID NO: 3; and
    wherein the light chain variable region comprises three light chain complementarity determining regions (LCDRs), wherein LCDR1 comprises the amino acid sequence set forth in SEQ ID NO: 4, LCDR2 comprises the amino acid sequence of VDG, and LCDR3 comprises the amino acid sequence set forth in SEQ ID NO: 5.

2. The antibody or antigen-binding fragment thereof of claim 1, wherein the antibody or antigen-binding fragment thereof is a full-length antibody.

3. The antibody or antigen-binding fragment thereof of claim 2, wherein the full-length antibody is a canine antibody.

4. The antibody or antigen-binding fragment thereof of claim 1, wherein the antigen binding domain comprises a heavy chain variable region comprising an amino acid sequence having at least 90% identity to the amino acid sequence set forth in SEQ ID NO: 6.

5. The antibody or antigen-binding fragment thereof of claim 1, wherein the antigen binding domain comprises a heavy chain variable region comprising an amino acid sequence having at least 95% identity to the amino acid sequence set forth in SEQ ID NO: 6.

6. The antibody or antigen-binding fragment thereof of claim 1, wherein the antigen binding domain comprises a light chain variable region comprising an amino acid sequence having at least 90% identity to the amino acid sequence set forth in SEQ ID NO: 8.

7. The antibody or antigen-binding fragment thereof of claim 1, wherein the antigen binding domain comprises a light chain variable region comprising an amino acid sequence having at least 95% identity to the amino acid sequence set forth in SEQ ID NO: 8.

8. The antibody or antigen-binding fragment thereof of claim 2, wherein the antigen binding domain comprises (i) a heavy chain variable region comprising an amino acid sequence having at least 95% identity to the amino acid sequence set forth in SEQ ID NO: 6; and (ii) a light chain variable region comprising an amino acid sequence having at least 95% identity to the amino acid sequence set forth in SEQ ID NO: 8.

9. A full-length antibody comprising an antigen-binding domain that specifically binds to an epitope of canine cytotoxic T lymphocyte associated protein 4 (CTLA-4), wherein the antigen-binding domain comprises:
(i) a heavy chain variable region that comprises three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and
(ii) a light chain variable region that comprises three light chain complementarity determining regions (LCDRs), wherein LCDR1 comprises the amino acid sequence set forth in SEQ ID NO: 4, LCDR2 comprises the amino acid sequence of VDG, and LCDR3 comprises the amino acid sequence set forth in SEQ ID NO: 5.

10. The full-length antibody of claim 9, wherein:
(i) the heavy chain variable region comprises an amino acid sequence having at least 90% identity to the amino acid sequence set forth in SEQ ID NO: 6; and
(ii) the light chain variable region comprises an amino acid sequence having at least 90% identity to the amino acid sequence set forth in SEQ ID NO: 8.

11. The full-length antibody of claim 9, comprising a heavy chain amino acid sequence comprising an amino acid sequence having at least 90% identity to an amino acid sequence selected from the group consisting of SEQ ID NOs: 10, 12, 14, and 16 and a light chain comprising an amino acid sequence having at least 90% identity to the amino acid sequence set forth in SEQ ID NO: 18.

12. The full-length antibody of claim 9, wherein the full-length antibody is a canine antibody.

13. An isolated nucleic acid encoding the antibody or antigen-binding fragment thereof of claim 1.

14. A vector comprising the isolated nucleic acid of claim 13.

15. A host cell comprising the vector of claim 14.

16. A method of producing an antibody or antigen-binding fragment thereof that binds to canine cytotoxic T lymphocyte associated protein 4 (CTLA-4), the method comprising culturing the host cell of claim 15.

17. A pharmaceutical composition comprising the antibody or antigen-binding fragment thereof of claim 1, and a pharmaceutically acceptable carrier.

18. A method for treating a cancer in a subject in need thereof, the method comprising administering to the subject a therapeutically effective amount of the antibody or antigen-binding fragment thereof of claim 1, thereby treating the cancer in the subject.

19. The method of claim 18, wherein the cancer is associated with cytotoxic T lymphocyte associated protein 4 (CTLA-4).

20. The method of claim 18, wherein the subject is canine.

* * * * *